US008942817B2

(12) United States Patent
Hyde et al.

(10) Patent No.: US 8,942,817 B2
(45) Date of Patent: Jan. 27, 2015

(54) BROADCASTING A SIGNAL INDICATIVE OF A DISEASE, DISORDER, OR SYMPTOM DETERMINED IN RESPONSE TO CONTACTLESSLY ACQUIRED INFORMATION

(75) Inventors: Roderick A. Hyde, Redmond, WA (US); Muriel Y. Ishikawa, Livermore, CA (US); Eric C. Leuthardt, St. Louis, MO (US); Dennis J. Rivet, Portsmouth, VA (US); Elizabeth A. Sweeney, Seattle, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1222 days.

(21) Appl. No.: 12/462,132

(22) Filed: Jul. 28, 2009

(65) Prior Publication Data
US 2011/0028799 A1  Feb. 3, 2011

(51) Int. Cl.
*A61N 1/37* (2006.01)
*A61B 5/00* (2006.01)
*A61N 1/372* (2006.01)
(Continued)

(52) U.S. Cl.
CPC .............. *A61B 5/002* (2013.01); *A61B 5/0002* (2013.01); *A61B 5/0031* (2013.01); *A61N 1/37252* (2013.01); *A61N 1/36135* (2013.01); *A61N 1/08* (2013.01); *G06F 19/3481* (2013.01); *A61B 5/0022* (2013.01)
USPC ............................................... 607/60; 607/62

(58) Field of Classification Search
CPC . A61N 1/37252; A61N 1/08; A61N 1/36132; A61N 1/36135; A61B 5/0002; A61B 5/0031; A61B 5/002; A61B 5/0022
USPC ...................................................... 607/60, 62
See application file for complete search history.

(56) References Cited

U.S. PATENT DOCUMENTS 5,231,988 A   8/1993  Wernicke et al.
5,330,515 A   7/1994  Rutecki et al.
(Continued)

FOREIGN PATENT DOCUMENTS

WO    WO 03/048789 A2    6/2003
WO    WO 2006/091123 A1  8/2006

OTHER PUBLICATIONS

"About Deep Brain Stimulation"; Deep Brain Stimulation for Movement Disorder from Medtronic; bearing dates of 1995 and 2003; pp. 1-2; Medtronic.com, located at http://professional.medtronic.com/interventions/deep-brain-stimulation; printed on May 4, 2009.

(Continued)

*Primary Examiner* — Tammie K Heller
(74) *Attorney, Agent, or Firm* — Dorsey & Whitney LLP

(57) ABSTRACT

In an embodiment, a system includes a sensor device operable to detect a property of a mammal without a direct physical contact with the mammal. The system also includes a patient assessment device operable to evaluate the detected property of the mammal for an indicator of a disease. The system further includes a patient information device including a computer-readable medium, and configured to maintain and to provide access to information corresponding to the indication of the disease. The system further includes a transmitter device operable to broadcast a signal indicative of the disease.

40 Claims, 31 Drawing Sheets

(51) Int. Cl.
*A61N 1/36* (2006.01)
*G06F 19/00* (2011.01)
*A61N 1/08* (2006.01)

(56) References Cited

U.S. PATENT DOCUMENTS

| | | | |
|---|---|---|---|
| 5,335,657 | A | 8/1994 | Terry, Jr. et al. |
| 5,458,625 | A | 10/1995 | Kendall |
| 6,062,216 | A * | 5/2000 | Corn ............... 128/204.23 |
| 6,173,068 | B1 | 1/2001 | Prokoski |
| 6,405,732 | B1 | 6/2002 | Edwards et al. |
| 6,514,199 | B1 | 2/2003 | Alessandri |
| 6,564,102 | B1 | 5/2003 | Boveja |
| 6,832,114 | B1 | 12/2004 | Whitehurst et al. |
| 7,076,307 | B2 | 7/2006 | Boveja et al. |
| 7,146,217 | B2 | 12/2006 | Firlik et al. |
| 7,155,284 | B1 | 12/2006 | Whitehurst et al. |
| 7,209,787 | B2 | 4/2007 | DiLorenzo |
| 7,242,984 | B2 | 7/2007 | DiLorenzo |
| 7,245,956 | B2 | 7/2007 | Matthews et al. |
| 7,263,405 | B2 | 8/2007 | Boveja et al. |
| 7,269,457 | B2 | 9/2007 | Shafer et al. |
| 7,272,431 | B2 | 9/2007 | McGrath |
| 7,282,030 | B2 | 10/2007 | Frei et al. |
| 7,684,854 | B2 * | 3/2010 | Park et al. ............... 600/509 |
| 2003/0216789 | A1 * | 11/2003 | Deem et al. ............... 607/9 |
| 2004/0123667 | A1 | 7/2004 | McGrath |
| 2004/0172066 | A1 | 9/2004 | Wagner et al. |
| 2005/0021101 | A1 | 1/2005 | Chen et al. |
| 2005/0065815 | A1 * | 3/2005 | Mazar et al. ............... 705/2 |
| 2005/0070974 | A1 | 3/2005 | Knudson et al. |
| 2005/0075701 | A1 | 4/2005 | Shafer |
| 2005/0102167 | A1 | 5/2005 | Kapoor |
| 2005/0187584 | A1 | 8/2005 | Denker et al. |
| 2006/0058694 | A1 | 3/2006 | Clark et al. |
| 2006/0058851 | A1 | 3/2006 | Cigaina |
| 2006/0122675 | A1 | 6/2006 | Libbus et al. |
| 2006/0217781 | A1 | 9/2006 | John |
| 2006/0247719 | A1 | 11/2006 | Maschino et al. |
| 2006/0247721 | A1 | 11/2006 | Maschino et al. |
| 2006/0247722 | A1 | 11/2006 | Maschino et al. |
| 2006/0259077 | A1 | 11/2006 | Pardo et al. |
| 2006/0293721 | A1 | 12/2006 | Tarver et al. |
| 2007/0027484 | A1 | 2/2007 | Guzman et al. |
| 2007/0027496 | A1 | 2/2007 | Parnis et al. |
| 2007/0093870 | A1 | 4/2007 | Maschino |
| 2007/0191906 | A1 | 8/2007 | Iyer et al. |
| 2008/0045832 | A1 | 2/2008 | McGrath |
| 2009/0227925 | A1 | 9/2009 | McBean et al. |
| 2009/0312808 | A1 | 12/2009 | Tyler et al. |
| 2010/0321163 | A1 | 12/2010 | Stevenson |
| 2011/0029044 | A1 | 2/2011 | Hyde et al. |

OTHER PUBLICATIONS

Avagyan, R. et al.; "New Diagnostic Methods in Acupuncture"; Diagnostics; bearing dates of May 21-23, 1999; pp. 7; ICMART '99 International Medical Acupuncture Symposium; located at http://www.acutechinternational.com/html/diagnostics.html; printed on May 12, 2009.

Bertinotti, Luca et al.; "The Use of Pupillometry in Joint and Connective Tissue Diseases"; *Annals of the New York Academy of Sciences*; 2002; pp. 446-455; vol 966, Issue Neuroendocrine Immune Basis of the Rheumatic Diseases II: Proceedings of the Second International Conference; The New York Academy of Sciences (abstract only).

Black, Jed E. et al.; "Narcolepsy and Syndromes of Central Nervous System-Mediated Sleepiness"; Focus; Fall 2005; pp. 585-597; vol. III, No. 4; focus.psychiatryonline.org.

Black, Jed E. et al.; "Narcolepsy and Syndromes of Primary Excessive Daytime Somnolence"; Semin Neurol; Oct. 26, 2004; pp. 271-282; 24(3); located at www.medscape.com.

Buckley, Theresa M. et al.; "Review: On the Interactions of the Hypothalamic-Pituitary-Adrenal (HPA) Axis and Sleep: Normal HPA Axis Activity and Circadian Rhythm, Exemplary Sleep Disorders"; The Journal of Clinical Endocrinology & Metabolism; May 2005; pp. 3106-3114; 90(5); The Endocrine Society.

Burt, Victoria; "Stimulating the brain"; Medical Design; Mar. 1, 2008; pp. 1-13; located at http://medicaldesign.com/electrical-components/stimulating_brain/; printed on May 1, 2009.

Buszewski, Boguslaw et al.; "Human exhaled air analytics: biomarkers of diseases"; *Biomedical Chromatography*; Jun. 2007; pp. 553-566; vol. 21, Issue 6; Biomedical Chromatography (abstract only).

Chu, Jennifer; "A Gentler Way to Jump-Start the Brain"; technologyreview.com; May 19, 2008; pp. 1-4; Technology Review; located at http://www.technologyreview.com/printer_friendly_article.aspx?id=20789&channel=biomedicine&section=; printed on May 11, 2009.

Harland, C.J. et al.; "Electric potential probes-new directions in the remote sensing of the human body"; Measurement Science and Technology; 2002; pp. 163-169; vol. 13; Institute of Physics Publishing.

Harland, C.J. et al.; "High resolution ambulatory electrocardiographic monitoring using wrist-mounted electric potential sensors"; Measurement Science and Technology; 2003; pp. 923-928; vol. 14; Institute of Physics Publishing.

Harland, C.J. et al.; "Remote detection of human electroencephalograms using ultrahigh input impedance electric potential sensors"; Applied Physics Letters; Oct. 21, 2002; pp. 3284-3286; vol. 81, No. 17; American Institute of Physics.

Harle, P. et al.; "Predictive and potentially predictive factors in early arthritis: a multidisciplinary approach"; Rheumatology; Feb. 16, 2005; pp. 426-433; vol. 44, No. 4; British Society for Rheumatology.

Huston, JM et al.; "Transcutaneous vagus nerve stimulation reduces serum high mobility group box 1 levels and improves survival in murine sepsis"; Crit Care Med.; Dec. 2007; pp. 2762-2768; 35(12) (abstract only).

"Inexpensive, passive gamma-ray sensor"; FactSheet; pp. 1; Oak Ridge National Laboratory; Advanced Nuclear Measurements and Control.

Kokoszka, Joseph et al.; "Determination of inflammatory bowel disease activity by breath pentane analysis"; Journal Diseases of the Colon & Rectum; Jun. 1993; pp. 597-601; vol. 36, No. 6; Springer New York (abstract only).

Kuo, Terry B.J. et al.; "Asymmetry in Sympathetic and Vagal Activities During Sleep-Wake Transitions"; SLEEP; 2008; pp. 311-320; vol. 31, No. 3.

Lim, Yong Gyu et al.; "ECG measurement on a chair without conductive contact"; IEEE Transactions on Biomedical Engineering; May 2006; pp. 956-959; vol. 53, Issue 5; IEEE (abstract only).

Marzano, Cristina et al.; "Slow Eye Movements and Subjective Estimates of Sleepiness Predict EEG Power Changes During Sleep Deprivation"; SLEEP; 2007; pp. 610-616; vol. 30, No. 5.

Massimini, Marcello et al.; "Triggering sleep slow waves by transcranial magnetic stimulation"; Proceedings of the National Academy of Sciences; May 15, 2007; pp. 8496-8501; vol. 104, No. 20; The National Academy of Sciences of the USA.

"Northstar Neuroscience Receives FDA Approval for a Clinical Study of its Cortical Stimulation System for the Treatment of Major Depressive Disorder"; Northstar Neuroscience; pp. 1-2; Northstar Neuroscience Inc.; located at http://ir.northstarneuro.com/releasedetail.cfm?ReleaseID=345732; printed on May 1, 2009.

Norton, Stephen J.; "Can ultrasound be used to stimulate nerve tissue?"; BioMedical Engineering OnLine; Mar. 4, 2003; pp. 1-9; 2:6; BioMed Central Ltd.

Pace-Schott, Edward F. et al.; "The Neurobiology of Sleep: Genetics, Cellular Physiology and Subcortical Networks"; Neuroscience; Aug. 2002; pp. 591-605; vol. 3; Nature Publishing Group.

Papadelis, Christos et al.; "Indicators of Sleepiness in an ambulatory EEG study of night driving"; Proceedings of the 28th IEEE EMBS Annual International Conference; bearing dates of Aug. 30-Sep. 3, 2006; pp. 6201-6204; SuA01.5; IEEE.

Papadelis, Christos et al.; "Monitoring sleepiness with on-board electrophysiological recordings for preventing sleep-deprived traffic accidents"; Clinical Neurophysiology; 2007; pp. 1906-1922; vol. 118; International Federation of Clinical Neurophysiology; Elsevier Ireland Ltd.

(56) References Cited

OTHER PUBLICATIONS

Pelli, Maria Antonietta et al.; "Breath alkanes determination in ulcerative colitis and Crohn's disease"; Journal Diseases of the Colon & Rectum; Jan. 1999; pp. 71-76; vol. 42, No. 1; Springer New York (abstract only).

Pongratz, Georg et al.; "Corticotropin-Releasing Factor Modulates Cardiovascular and Pupillary Autonomic Reflexes in Man"; *Annals of the New York Academy of Sciences*; Jan. 24, 2006; pp. 373-383; vol. 966, Issue Neuroendocrine Immune Basis of the Rheumatic Diseases II: Proceedings of the Second International Conference; The New York Academy of Sciences (abstract only).

Prance, R.J. et al.; "Adaptive Electric Potential Sensors for smart signal acquisition and processing"; Journal of Physics: Conference Series; 2007; pp. 1-5; 76; IOP Publishing.

"Recent Publications"; Centre for Physical Electronics and Quantum Technology; pp. 1-3; University of Sussex; located at http://www.sussex.ac.uk/pei/1-2-6.html; printed on May 11, 2009.

Rizzo, Pierpaolo et al.; "Chronic Vagus Nerve Stimulation Improves Alertness and Reduces Rapid Eye Movement Sleep in Patients Affected by Refractory Epilepsy"; SLEEP; 2003; pp. 607-611; vol. 26, No. 5; Sleep.

Sallam H. et al.; "Transcutaneous electrical nerve stimulation (TENS) improves upper GI symptoms and balances the sympathovagal activity in scleroderma patients"; Digestive Diseases and Sciences; May 2007; pp. 1329-1337; 52(5); Epub Mar. 20, 2007 (abstract only).

Singer, Emily; "Tiny Implants for Treating Chronic Pain"; Technology Review; May 15, 2009, pp. 1-3; MIT; located at http://www.technologyreview.com/biomedicine/22657/?nlid=2032; printed on May 18, 2009.

"Swine flu scanner installed at Phuket Airport"; Phuket Gazette; Apr. 28, 2009; pp. 1; located at http://www.thaivisa.com/forum/Swine-Flu-Scanner-Installed-Phuket-t260956.html.

"Therapy"; Northstar Neuroscience; bearing a date of 2009; pp. 1-2; Northstar Neuroscience, Inc.; located at http://www.northstarneuro.com/therapy/index.asp; printed on Apr. 6, 2009.

Troitskii, V.S. et al.; "Intrinsic Microwave Radiation From the Human Body"; Radiofizika; Jan. 1981; pp. 85; vol. 24, No. 1; Plenum Publishing Corporation; located at http://resources.metapress.com/pdf-preview.axd?code=u871r . . . ; printed on May 12, 2009.

Tyler, William J. et al.; "Remote Excitation of Neuronal Circuits Using Low-Intensity, Low-Frequency Ultrasound"; PLoS ONE; Oct. 2008; pp. 1-11; vol. 3, Issue 10; plosone.org.

Ventureyra, E.C.G.; "Transcutaneous vagus nerve stimulation for partial onset seizure therapy"; Journal Child's Nervous System; Feb. 2000; pp. 101-102; vol. 16, No. 2; Springer Berlin/Heidelberg (abstract only).

"Wireless Neurostimulation"; Micro Transponder; pp. 1; located at http://www.microtransponder.com/technology/index.html; printed on May 18, 2009.

\* cited by examiner

An apparatus.

410 Means for sensing a property of a mammal without physically contacting the mammal.

420 Means for generating an electronic signal indicative of the sensed property of the mammal.

430 Means for modulating a nervous system component of the mammal in response to the electronic signal indicative of a property of the mammal.

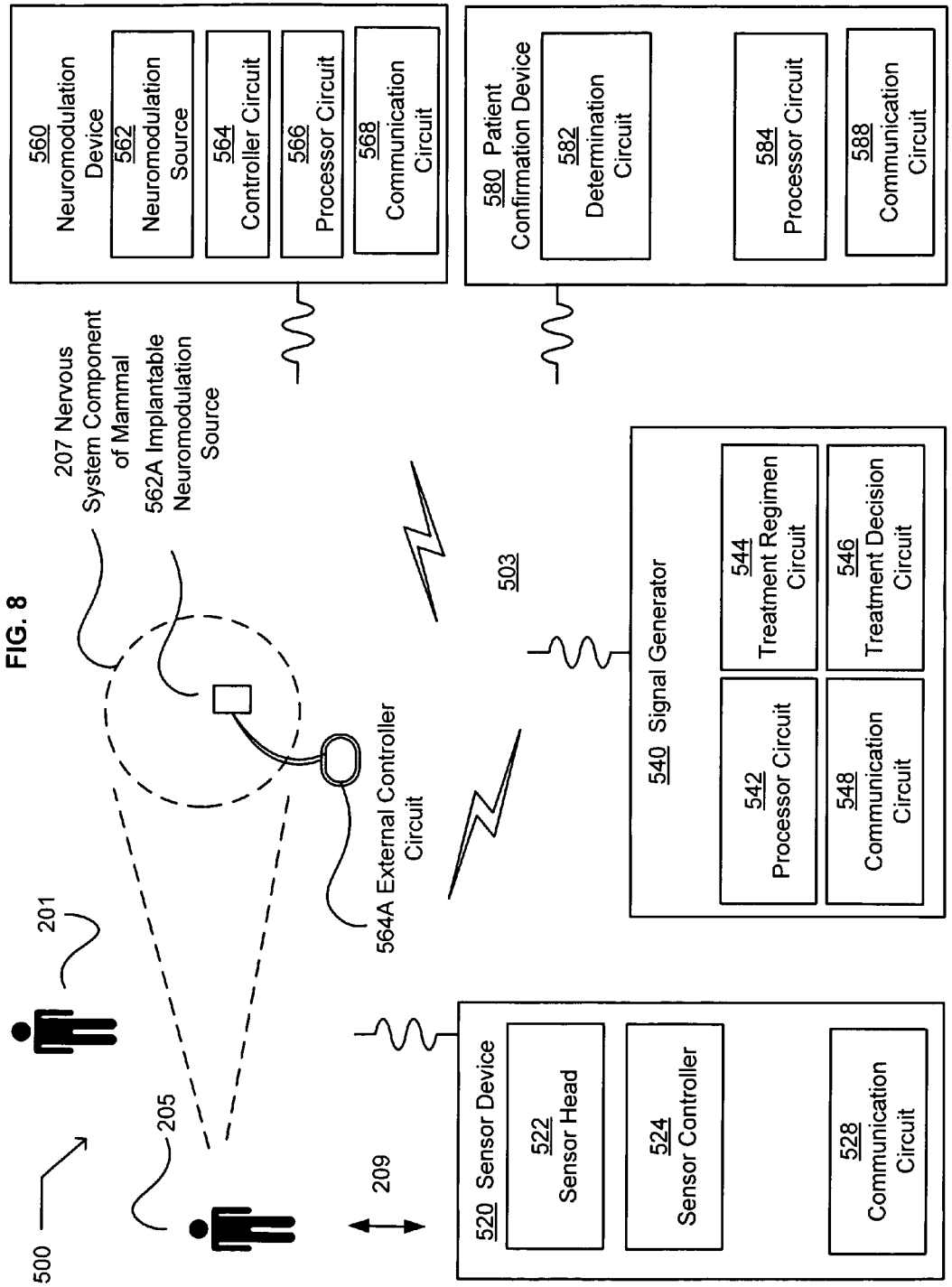

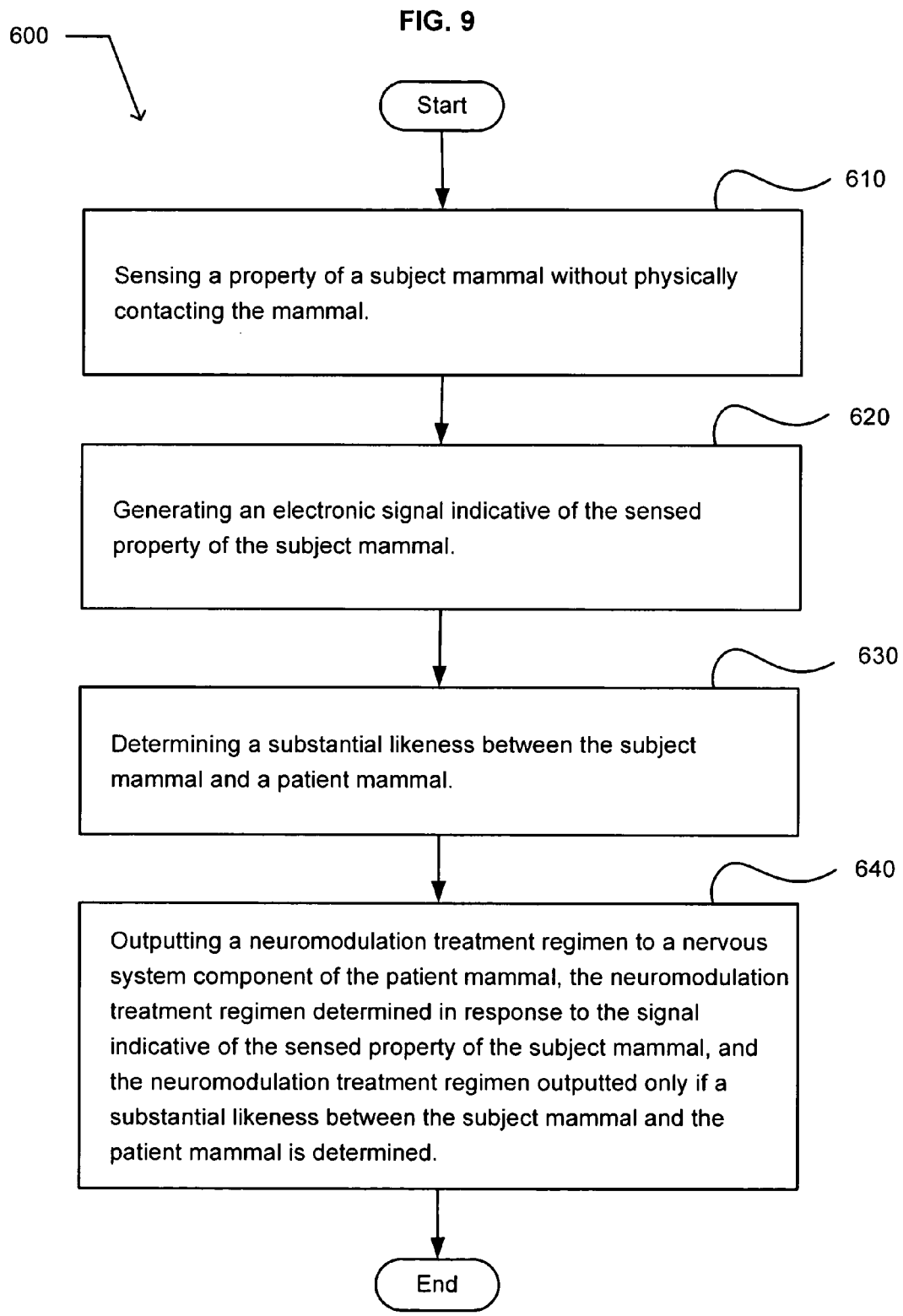

FIG. 10

700 — An apparatus.

710 Means for sensing a property of a mammal without physically contacting the mammal.

720 Means for generating an electronic signal indicative of the sensed property of the mammal.

730 Means for determining a substantial likeness between the subject mammal and a patient mammal.

740 Means for outputting a neuromodulation treatment regimen to a nervous system component of the patient mammal, the neuromodulation treatment regimen determined in response to the signal indicative of the sensed property of the subject mammal, and the neuromodulation treatment regimen outputted only if a substantial likeness between the subject mammal and the patient mammal is determined.

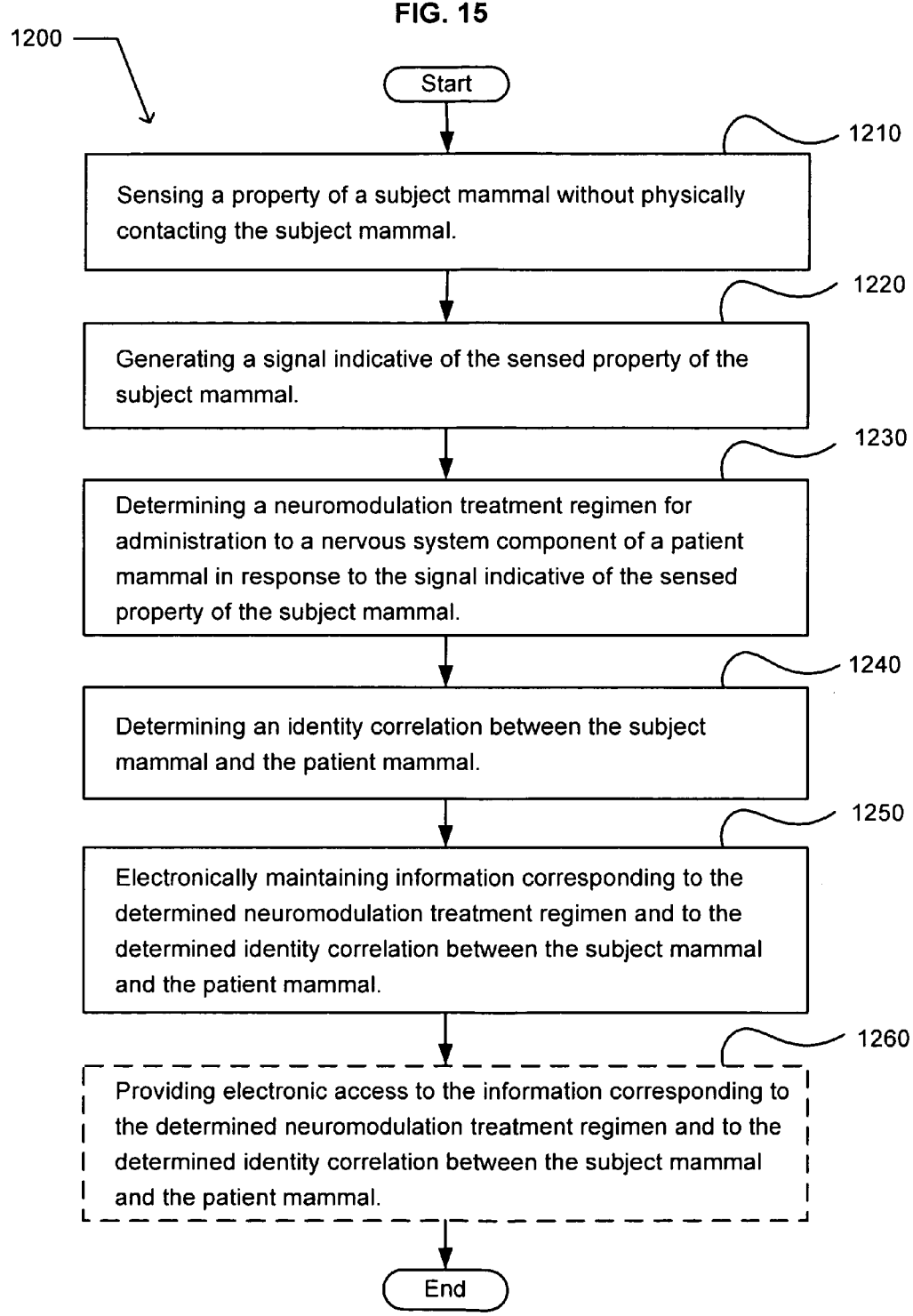

A system.

1310 Means for sensing a property of a subject mammal without physically contacting the subject mammal.

1320 Means for generating a signal indicative of the sensed property of the subject mammal.

1330 Means for determining a neuromodulation treatment regimen for administration to a nervous system component of a patient mammal in response to the signal indicative of the sensed property of the subject mammal.

1340 Means for determining an identity correlation between the subject mammal and the patient mammal.

1350 Means for electronically maintaining information corresponding to the determined neuromodulation treatment regimen and the determined identity correlation between the subject mammal and the patient mammal.

1360 Means for providing electronic access to the information corresponding to the determined neuromodulation treatment regimen and to the determined identity correlation between the subject mammal and the patient mammal.

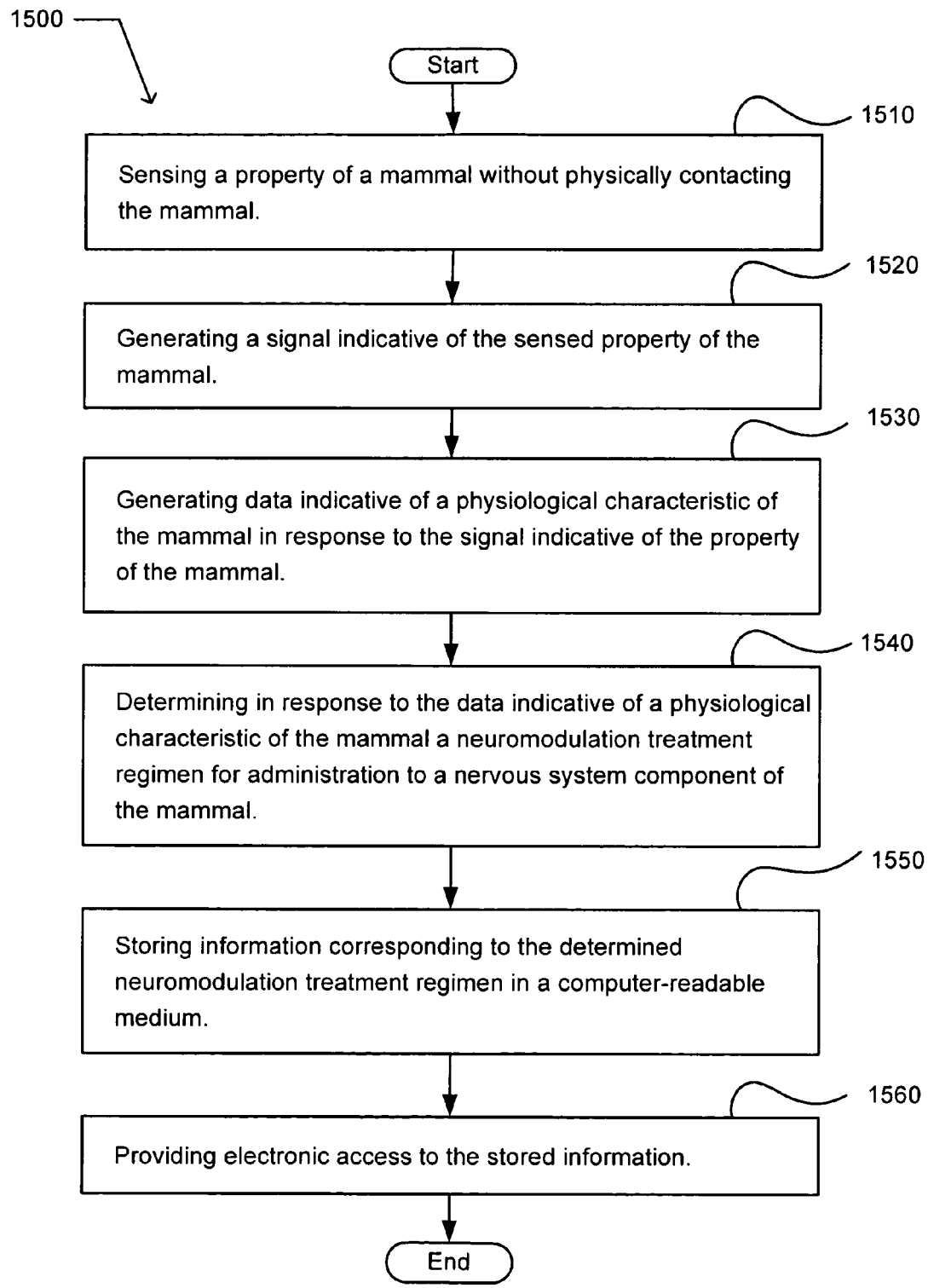

FIG. 19

1600 — A system.

1610 Means for sensing a property of a mammal without physically touching the mammal.

1620 Means for generating a signal indicative of the sensed property of the mammal.

1630 Means for generating data indicative of a physiological characteristic of the mammal in response to the signal indicative of the property of the mammal.

1640 Means for selecting in response to the data indicative of a physiological characteristic of the mammal a neuromodulation treatment regimen for administration to a nervous system component of the mammal.

1650 Means for storing information corresponding to the determined neuromodulation treatment regimen in a computer-readable medium.

1660 Means for providing electronic access to the stored information.

Acquiring electronic data indicative of a property of a mammal without making physical contact with the mammal.

1812 Acquiring electronic data indicative of a property of a mammal present in a space without making physical contact with the mammal.

1822 In an operation performed at a location remote from the space, extracting digital information indicative of a physiological characteristic of the mammal from the electronic data indicative of the state of the mammal.

1812 Acquiring electronic data indicative of a property of a mammal present in a space without making physical contact with the mammal.

1852 In an operation performed at a location remote from the space, choosing from an electronically readable treatment database a neuromodulation treatment regimen for administration to the mammal in response to the information indicative of a physiological characteristic of the mammal.

1812 Acquiring electronic data indicative of a property of a mammal present in a space without making physical contact with the mammal.

1822 In an operation performed at a location remote from the space, extracting digital information indicative of a physiological characteristic of the mammal from the electronic data indicative of the state of the mammal.

1854 In an operation performed at a location remote from the space, choosing from an electronically readable treatment database a neuromodulation treatment regimen for administration to the mammal in response to the information indicative of a physiological characteristic of the mammal.

Extracting digital information indicative of a physiological characteristic of the mammal from the electronic data indicative of the property of the mammal.

1826 Distilling digital information indicative of a physiological characteristic of the mammal from the electronic data indicative of the property of the mammal.

1828 Inferring digital information indicative of a physiological characteristic of the mammal from the electronic data indicative of the property of the mammal.

1832 Deriving digital information indicative of a physiological characteristic of the mammal from the electronic data indicative of the property of the mammal.

1834 Extracting using an artificial intelligence tool digital information indicative of a physiological characteristic of the mammal from the electronic data indicative of the property of the mammal.

1836 Employing an artificial intelligence technique to extract digital information indicative of a physiological characteristic of the mammal from the electronic data indicative of the property of the mammal.

1838 In an operation performed in a space, extracting digital information indicative of a physiological characteristic of the mammal from the electronic data indicative of the property of the mammal.

1856 In another operation performed at a location remote from the space, choosing from an electronically readable treatment database a neuromodulation treatment regimen for administration to the mammal in response to the information indicative of a physiological characteristic of the mammal.

Choosing from an electronically-readable treatment database a neuromodulation treatment regimen for administration to the mammal in response to the information indicative of a physiological characteristic of the mammal.

1857 Choosing from an electronically-readable treatment database a neuromodulation treatment regimen for administration to the mammal in response to a selected outcome and the information indicative of a physiological characteristic of the mammal.

1858 Choosing from a digitally maintained treatment decision table a neuromodulation treatment regimen for administration to the mammal in response to the information indicative of a physiological characteristic of the mammal.

1862 Choosing from a digital library correlating physiological characteristics and neural stimuli a neuromodulation treatment regimen for administration to the mammal in response to the information indicative of a physiological characteristic of the mammal.

1864 Deciding if treatment is indicated in response to the information indicative of a physiological characteristic of the mammal, and if treatment is indicated choosing from an electronically-readable treatment database a neuromodulation treatment regimen for administration to the mammal in response to the information indicative of a physiological characteristic of the mammal.

Electronically initiating an administration of the chosen neuromodulation treatment regimen to a nervous system component of the mammal.

1874 Facilitating a transformation of a physiological characteristic of the mammal to a selected state by electronically initiating an administration of the chosen neuromodulation treatment regimen to a nervous system component of the mammal.

1876 Substantially transforming a physiological characteristic of the mammal to a selected state by electronically initiating an administration of the chosen neuromodulation treatment regimen to a nervous system component of the mammal.

1878 Electronically initiating an administration of a selected outcome-promoting dose of the chosen neuromodulation treatment regimen to a nervous system component of the mammal.

1882 Electronically initiating an administration of the chosen neuromodulation treatment regimen to a nervous system component of the mammal and provoking a selected outcome.

1884 Electronically initiating an administration of the chosen neuromodulation treatment regimen to a nervous system component of the mammal and provoking a state of the mammal.

1886 Administering the chosen neuromodulation treatment regimen to a nervous system component of the mammal and achieving a selected change of a state of the mammal.

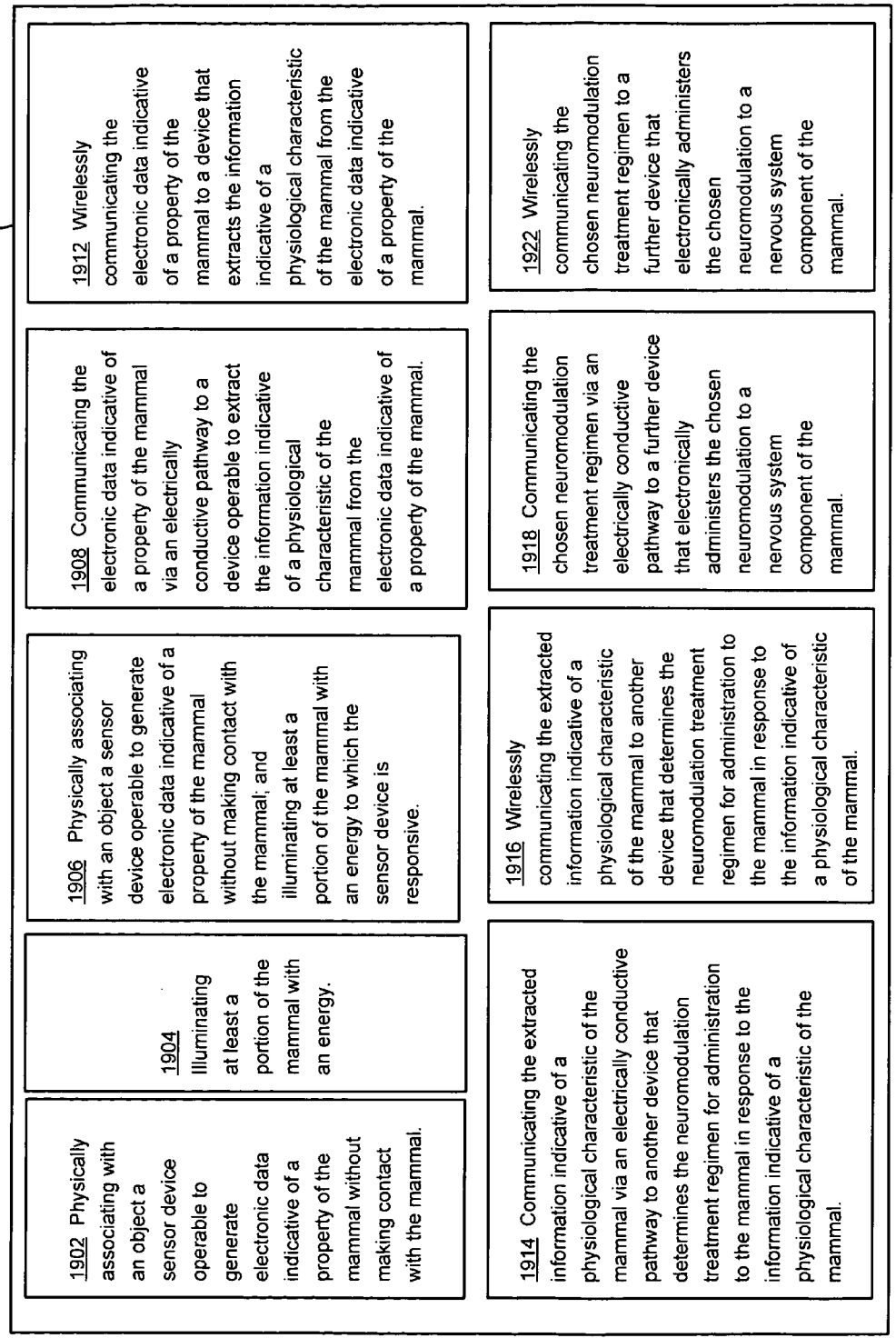

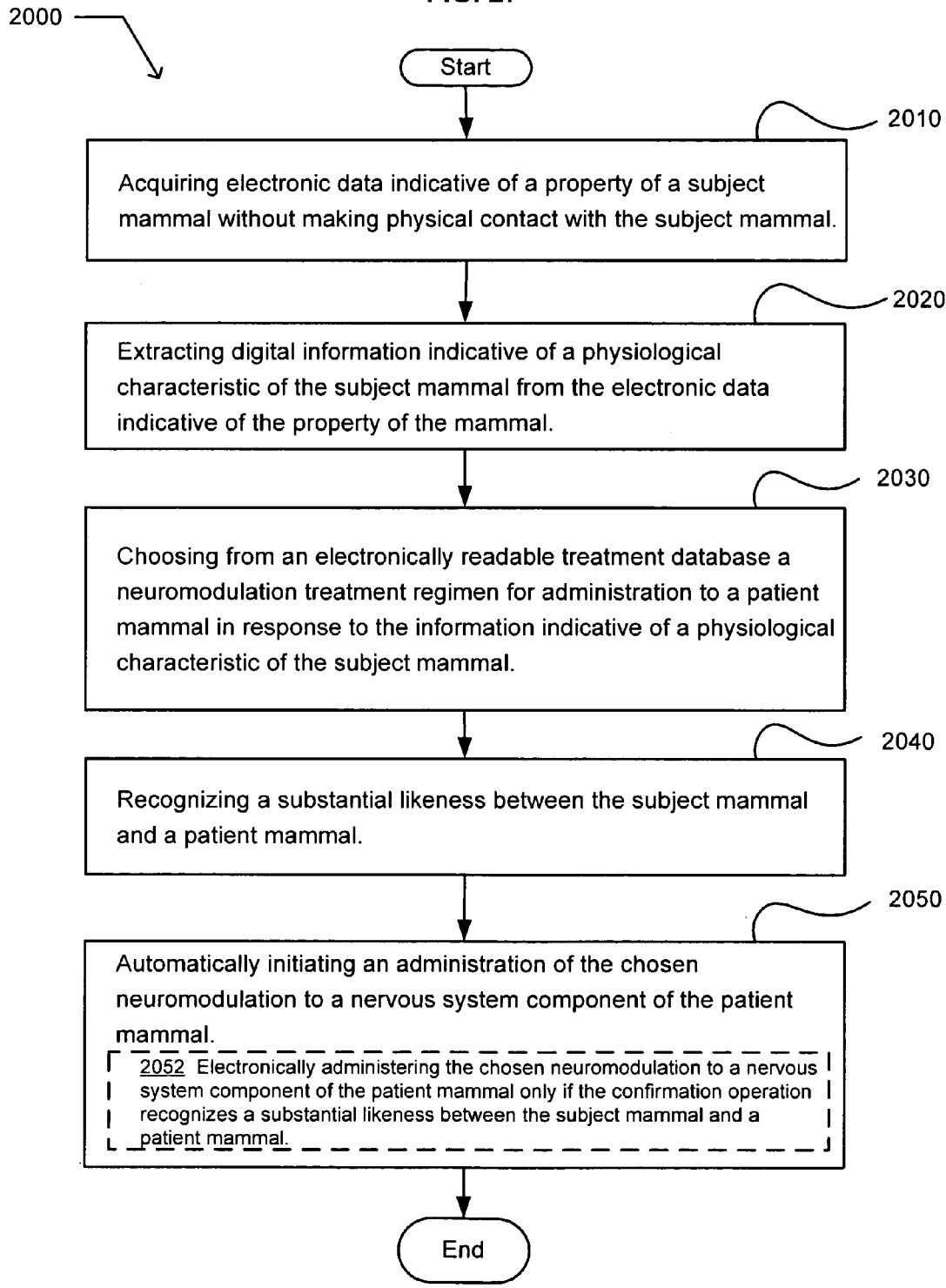

BROADCASTING A SIGNAL INDICATIVE OF A DISEASE, DISORDER, OR SYMPTOM DETERMINED IN RESPONSE TO CONTACTLESSLY ACQUIRED INFORMATION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 12/462,130, now U.S. Pat. No. 8,374,701, entitled STIMULATING A NERVOUS SYSTEM COMPONENT OF A MAMMAL IN RESPONSE TO CONTACTLESSLY ACQUIRED INFORMATION, naming Roderick A. Hyde, Muriel Y. Ishikawa, Eric C. Leuthardt, Dennis J. Rivet, Elizabeth A. Sweeney, Lowell L. Wood, Jr., and Victoria Y.H. Wood as inventors, filed Jul. 28, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/462,123, now U.S. Patent No. 8,346,354, entitled DETERMINING A NEUROMODULATION TREATMENT REGIMEN IN RESPONSE TO CONTACTLESSLY ACQUIRED INFORMATION, naming Roderick A. Hyde, Muriel Y. Ishikawa, Eric C. Leuthardt, Dennis J. Rivet, Elizabeth A. Sweeney, Lowell L. Wood, Jr., and Victoria Y.H. Wood as inventors, filed Jul. 28, 2009, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/462,124 entitled ELECTRONICALLY INITIATING AN ADMINISTRATION OF A NEUROMODULATION TREATMENT REGIMEN CHOSEN IN RESPONSE TO CONTACTLESSLY ACQUIRED INFORMATION, naming Roderick A. Hyde, Muriel Y. Ishikawa, Eric C. Leuthardt, Dennis J. Rivet, Elizabeth A. Sweeney, Lowell L. Wood, Jr., and Victoria Y.H. Wood as inventors, filed Jul. 28, 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

An embodiment of the subject matter described herein includes a system. The system includes a sensor device operable to detect a property of a mammal without a direct physical contact with the mammal. The system also includes a patient assessment device operable to evaluate the detected property of the mammal for an indicator of a disease. The system further includes a patient information device including a computer-readable medium and configured to maintain and to provide access to information corresponding to the indication of the disease. The system further includes a transmitter device operable to broadcast a signal indicative of the disease. In an embodiment, the system may include a user interface operable to electronically output a human-perceivable indication of the disease in response to the broadcast signal indicative of the disease. In an embodiment, the system may include a treatment controller operable to control an administration of a neuromodulation treatment regimen to a nervous system component of the mammal. In an embodiment, the system may include a neuromodulation device operable to administer a neuromodulation treatment regimen to a nervous system component of the mammal. In an embodiment, the system may include an illumination source operable to illuminate at least a portion of the mammal with an energy to which the sensor device is responsive.

An embodiment of the subject matter described herein includes a system. The system includes a sensor device operable to detect a property of a mammal without a direct physical contact with the mammal. The system also includes a patient assessment device operable to evaluate the detected property of the mammal for an indicator of a disease. The system further includes a user interface device operable to electronically output a human-perceivable information responsive to the disease. The system also includes a patient information device having a computer-readable medium. The patient information device is configured to maintain information corresponding to the indicator of a disease, and to provide access to the maintained information. In an embodiment, the system may include a neuromodulation device operable to deliver a neuromodulation treatment regimen to a nervous system component of the mammal.

An embodiment of the subject matter described herein includes a method. The method includes acquiring electronic data indicative of a property of a mammal without making physical contact with the mammal. The method also includes evaluating the detected property of the mammal for an indicator of a disease based on the acquired electronic data indicative of a property of a mammal. The method further includes maintaining and providing access to electronically stored information corresponding to the indication of the disease. The method also includes broadcasting a signal indicative of the disease. In an embodiment, the method may include electronically outputting a human-perceivable indication of the disease in response to the broadcast signal indicative of the disease. In an embodiment, the method may include administering a neuromodulation treatment regimen to a nervous system component of the mammal in response to a human-originated input. In an embodiment, the method may include administering a neuromodulation treatment regimen to a nervous system component of the mammal in response to a human-originated input that is responsive to a proffered neuromodulation treatment regimen.

An embodiment of the subject matter described herein includes a system. The system includes means for acquiring electronic data indicative of a property of a mammal without making physical contact with the mammal. The system also includes means for evaluating the detected property of the mammal for an indicator of a disease based on the acquired electronic data indicative of a property of a mammal. The system further includes means for maintaining and providing access to electronically stored information corresponding to the indicator of the disease. The system also includes means for electronically outputting a human-perceivable indication of the disease. In an embodiment, the system may include means for electronically outputting a human-perceivable indication of the disease in response to the broadcast signal indicative of the disease. In an embodiment, the system may include means for administering a neuromodulation treatment regimen to a nervous system component of the mammal in response to a human-originated input.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 8 illustrates an example environment in which embodiments may be implemented;

FIG. 9 illustrates an example operational flow in which embodiments may be implemented;

FIG. 10 illustrates an example apparatus in which embodiments may be implemented;

FIG. 15 illustrates an example operational flow in which embodiments may be implemented;

FIG. 16 illustrates an example system in which embodiments may be implemented;

FIG. 18 illustrates an example operational flow in which embodiments may be implemented;

FIG. 19 illustrates an example system in which embodiments may be implemented;

FIG. 22 illustrates an alternative embodiment of the example operational flow described in FIG. 21;

FIG. 23 illustrates another alternative embodiment of the example operational flow described in FIG. 21;

FIG. 24 illustrates a further alternative embodiment of the example operational flow described in FIG. 21;

FIG. 25 illustrates another alternative embodiment of the example operational flow described in FIG. 21;

FIG. 26 illustrates a further alternative embodiment of the example operational flow described in FIG. 21;

FIG. 27 illustrates an example operational flow in which embodiments may be implemented;

DETAILED DESCRIPTION

Figure 1:
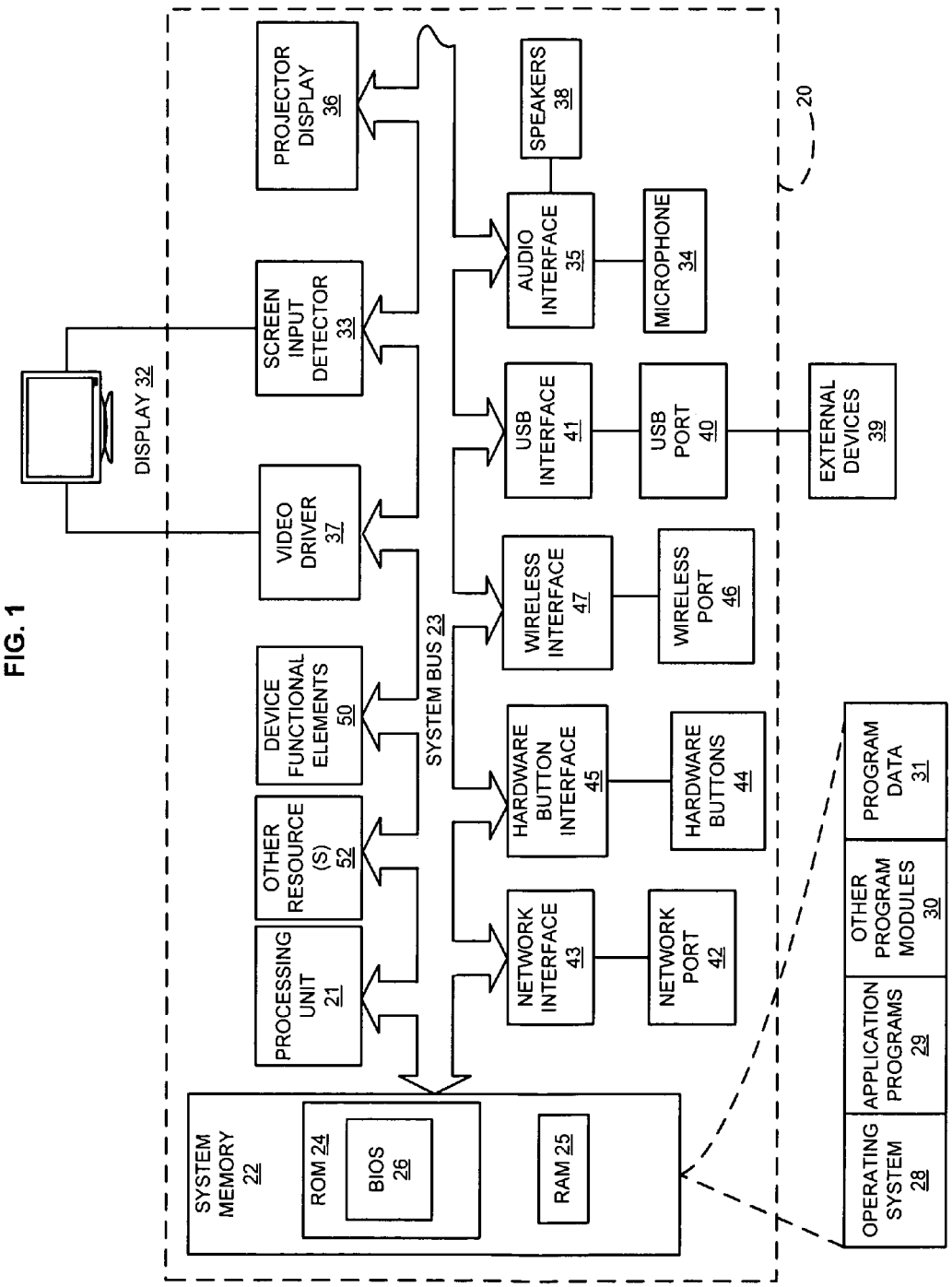
FIG. 1 illustrates an example embodiment of a thin computing device in which embodiments may be implemented.

In the following detailed description, reference is made to the accompanying drawings, which form a part hereof. In the drawings, similar symbols typically identify similar components, unless context dictates otherwise. The illustrated embodiments described in the detailed description, drawings, and claims are not meant to be limiting. Other embodiments may be utilized, and other changes may be made, without departing from the spirit or scope of the subject matter presented here.

FIG. 1 and the following discussion are intended to provide a brief, general description of an environment in which embodiments may be implemented. FIG. 1 illustrates an example system that includes a thin computing device 20, which may be included in an electronic device that also includes a device functional element 50. For example, the electronic device may include any item having electrical or electronic components playing a role in a functionality of the item, such as a limited resource computing device, a wireless communication device, a mobile wireless communication device, an electronic pen, a handheld electronic writing device, a digital camera, a scanner, an ultrasound device, an x-ray machine, a non-invasive imaging device, a cell phone, a PDA, a Blackberry® device, a printer, a refrigerator, a car, and an airplane. In another example, the thin computing device may be included in an implantable medical apparatus or device. In a further example, the thin computing device may be operable to communicate with an implantable or implanted medical apparatus.

The thin computing device 20 includes a processing unit 21, a system memory 22, and a system bus 23 that couples various system components including the system memory 22 to the processing unit 21. The system bus 23 may be any of several types of bus structures including a memory bus or memory controller, a peripheral bus, and a local bus using any of a variety of bus architectures. The system memory includes read-only memory (ROM) 24 and random access memory (RAM) 25. A basic input/output system (BIOS) 26, containing the basic routines that help to transfer information between sub-components within the thin computing device 20, such as during start-up, is stored in the ROM 24. A number of program modules may be stored in the ROM 24 or RAM 25, including an operating system 28, one or more application programs 29, other program modules 30 and program data 31.

A user may enter commands and information into the computing device 20 through input devices, such as a number of switches and buttons, illustrated as hardware buttons 44, connected to the system via a suitable interface 45. Input devices may further include a touch-sensitive display with suitable input detection circuitry, illustrated as a display 32 and screen input detector 33. The output circuitry of the touch-sensitive display 32 is connected to the system bus 23 via a video driver 37. Other input devices may include a microphone 34 connected through a suitable audio interface 35, and a physical hardware keyboard (not shown). Output devices may include at least one the display 32, or a projector display 36.

In addition to the display 32, the computing device 20 may include other peripheral output devices, such as at least one speaker 38. Other external input or output devices 39, such as a joystick, game pad, satellite dish, scanner or the like may be connected to the processing unit 21 through a USB port 40 and USB port interface 41, to the system bus 23. Alternatively, the other external input and output devices 39 may be connected by other interfaces, such as a parallel port, game port or other port. The computing device 20 may further include or be capable of connecting to a flash card memory (not shown) through an appropriate connection port (not shown). The computing device 20 may further include or be capable of connecting with a network through a network port 42 and network interface 43, and through wireless port 46 and corresponding wireless interface 47 may be provided to facilitate communication with other peripheral devices, including other computers, printers, and so on (not shown). It will be appreciated that the various components and connections shown are examples and other components and means of establishing communication links may be used.

The computing device 20 may be primarily designed to include a user interface. The user interface may include a character, a key-based, or another user data input via the touch sensitive display 32. The user interface may include using a stylus (not shown). Moreover, the user interface is not limited to an actual touch-sensitive panel arranged for directly receiving input, but may alternatively or in addition respond to another input device such as the microphone 34. For example, spoken words may be received at the microphone 34 and recognized. Alternatively, the computing device 20 may be designed to include a user interface having a physical keyboard (not shown).

The device functional elements 50 are typically application specific and related to a function of the electronic device, and is coupled with the system bus 23 through an interface (not shown). The functional elements may typically perform a single well-defined task with little or no user configuration or setup, such as a refrigerator keeping food cold, a cell phone connecting with an appropriate tower and transceiving voice or data information, a camera capturing and saving an image, or communicating with an implantable medical apparatus.

In certain instances, one or more elements of the thin computing device 20 may be deemed not necessary and omitted. In other instances, one or more other elements may be deemed necessary and added to the thin computing device.

Figure 2:
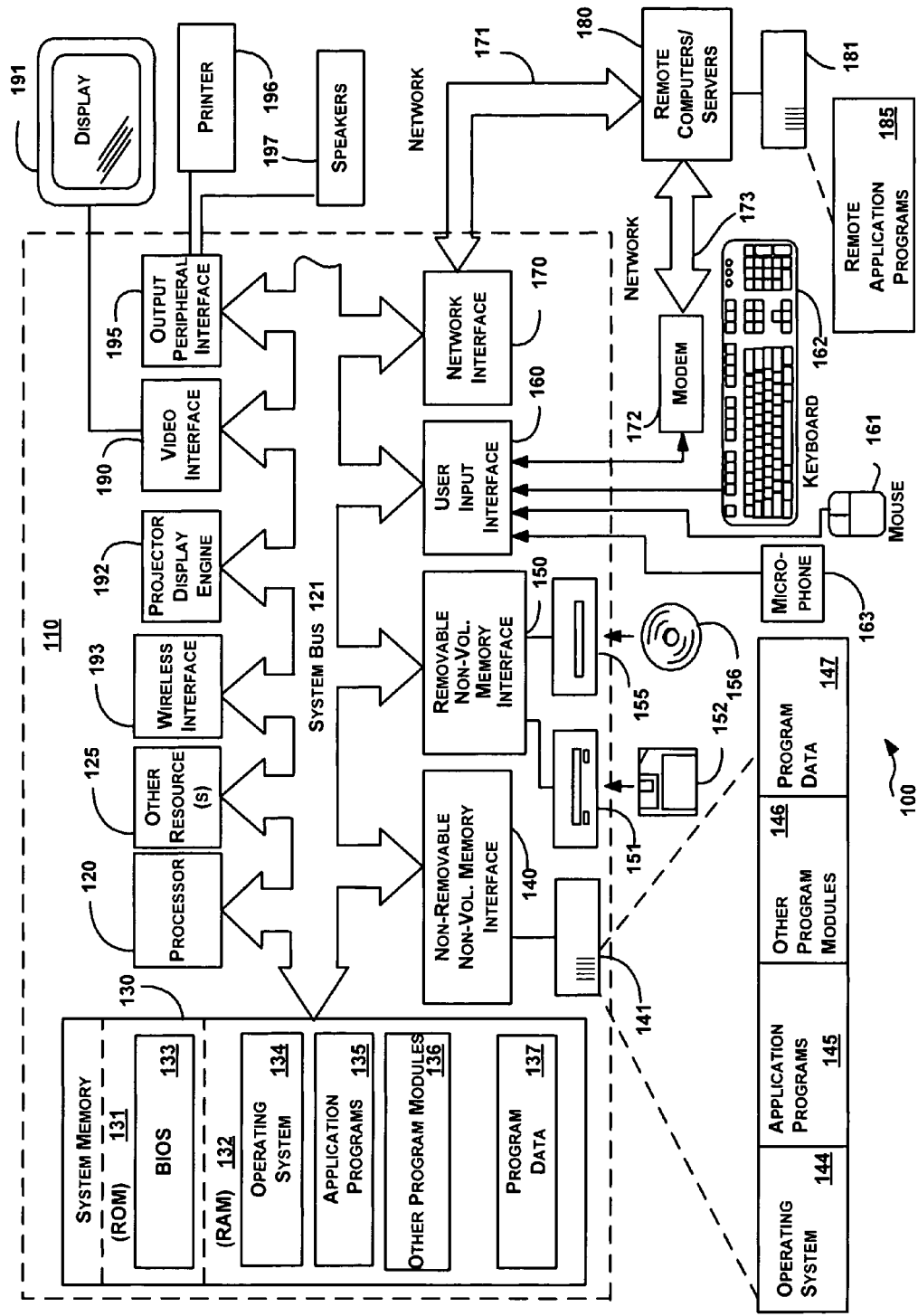
FIG. 2 illustrates an example embodiment of a general-purpose computing system in which embodiments may be implemented.

FIG. 2 illustrates an example embodiment of a general-purpose computing system in which embodiments may be implemented, shown as a computing system environment 100. Components of the computing system environment 100 may include, but are not limited to, a computing device 110 having a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The computing system environment 100 typically includes a variety of computer-readable media products. Computer-readable media may include any media that can be accessed by the computing device 110 and include both volatile and nonvolatile media, removable and non-removable media. By way of example, and not of limitation, computer-readable media may include computer storage media. By way of further example, and not of limitation, computer-readable media may include a communication media.

Computer storage media includes volatile and nonvolatile, removable and non-removable media implemented in any method or technology for storage of information such as computer-readable instructions, data structures, program modules, or other data. Computer storage media includes, but is not limited to, random-access memory (RAM), read-only memory (ROM), electrically erasable programmable read-only memory (EEPROM), flash memory, or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by the computing device 110. In a further embodiment, a computer storage media may include a group of computer storage media devices. In another embodiment, a computer storage media may include an information store. In another embodiment, an information store may include a quantum memory, a photonic quantum memory, or atomic quantum memory. Combinations of any of the above may also be included within the scope of computer-readable media.

Communication media may typically embody computer-readable instructions, data structures, program modules, or other data in a modulated data signal such as a carrier wave or other transport mechanism and include any information delivery media. The term "modulated data signal" means a signal that has one or more of its characteristics set or changed in such a manner as to encode information in the signal. By way of example, and not limitation, communication media include wired media, such as a wired network and a direct-wired connection, and wireless media such as acoustic, RF, optical, and infrared media.

The system memory 130 includes computer storage media in the form of volatile and nonvolatile memory such as ROM 131 and RAM 132. A RAM may include at least one of a DRAM, an EDO DRAM, a SDRAM, a RDRAM, a VRAM, or a DDR DRAM. A basic input/output system (BIOS) 133, containing the basic routines that help to transfer information between elements within the computing device 110, such as during start-up, is typically stored in ROM 131. RAM 132 typically contains data and program modules that are immediately accessible to or presently being operated on by processing unit 120. By way of example, and not limitation, FIG. 2 illustrates an operating system 134, application programs 135, other program modules 136, and program data 137. Often, the operating system 134 offers services to applications programs 135 by way of one or more application programming interfaces (APIs) (not shown). Because the operating system 134 incorporates these services, developers of applications programs 135 need not redevelop code to use the services. Examples of APIs provided by operating systems such as Microsoft's "WINDOWS" are well known in the art.

The computing device 110 may also include other removable/non-removable, volatile/nonvolatile computer storage media products. By way of example only, FIG. 2 illustrates a non-removable non-volatile memory interface (hard disk interface) 140 that reads from and writes for example to non-removable, non-volatile magnetic media. FIG. 2 also illustrates a removable non-volatile memory interface 150 that, for example, is coupled to a magnetic disk drive 151 that reads from and writes to a removable, non-volatile magnetic disk 152, or is coupled to an optical disk drive 155 that reads from and writes to a removable, non-volatile optical disk 156, such as a CD ROM. Other removable/nonremovable, volatile/non-volatile computer storage media that can be used in the example operating environment include, but are not limited to, magnetic tape cassettes, memory cards, flash memory cards, DVDs, digital video tape, solid state RAM, and solid state ROM. The hard disk drive 141 is typically connected to the system bus 121 through a non-removable memory interface, such as the interface 140, and magnetic disk drive 151 and optical disk drive 155 are typically connected to the system bus 121 by a removable non-volatile memory interface, such as interface 150.

The drives and their associated computer storage media discussed above and illustrated in FIG. 2 provide storage of computer-readable instructions, data structures, program modules, and other data for the computing device 110. In FIG. 2, for example, hard disk drive 141 is illustrated as storing an operating system 144, application programs 145, other program modules 146, and program data 147. Note that these components can either be the same as or different from the operating system 134, application programs 135, other program modules 136, and program data 137. The operating system 144, application programs 145, other program modules 146, and program data 147 are given different numbers here to illustrate that, at a minimum, they are different copies.

A user may enter commands and information into the computing device 110 through input devices such as a microphone 163, keyboard 162, and pointing device 161, commonly referred to as a mouse, trackball, or touch pad. Other input devices (not shown) may include at least one of a touch sensitive display, joystick, game pad, satellite dish, and scanner. These and other input devices are often connected to the processing unit 120 through a user input interface 160 that is coupled to the system bus, but may be connected by other interface and bus structures, such as a parallel port, game port, or a universal serial bus (USB).

A display 191, such as a monitor or other type of display device or surface may be connected to the system bus 121 via an interface, such as a video interface 190. A projector display engine 192 that includes a projecting element may be coupled to the system bus. In addition to the display, the computing device 110 may also include other peripheral output devices such as speakers 197 and printer 196, which may be connected through an output peripheral interface 195.

The computing system environment 100 may operate in a networked environment using logical connections to one or more remote computers, such as a remote computer 180. The remote computer 180 may be a personal computer, a server, a router, a network PC, a peer device, or other common network node, and typically includes many or all of the elements described above relative to the computing device 110, although only a memory storage device 181 has been illustrated in FIG. 2. The network logical connections depicted in FIG. 2 include a local area network (LAN) and a wide area network (WAN), and may also include other networks such as a personal area network (PAN) (not shown). Such networking environments are commonplace in offices, enterprise-wide computer networks, intranets, and the Internet.

When used in a networking environment, the computing system environment 100 is connected to the network 171 through a network interface, such as the network interface 170, the modem 172, or the wireless interface 193. The network may include a LAN network environment, or a WAN network environment, such as the Internet. In a networked environment, program modules depicted relative to the computing device 110, or portions thereof, may be stored in a remote memory storage device. By way of example, and not limitation, FIG. 2 illustrates remote application programs 185 as residing on computer medium 181. It will be appreciated that the network connections shown are examples and other means of establishing communication link between the computers may be used.

In certain instances, one or more elements of the computing device 110 may be deemed not necessary and omitted. In other instances, one or more other elements may be deemed necessary and added to the computing device.

Figure 3:
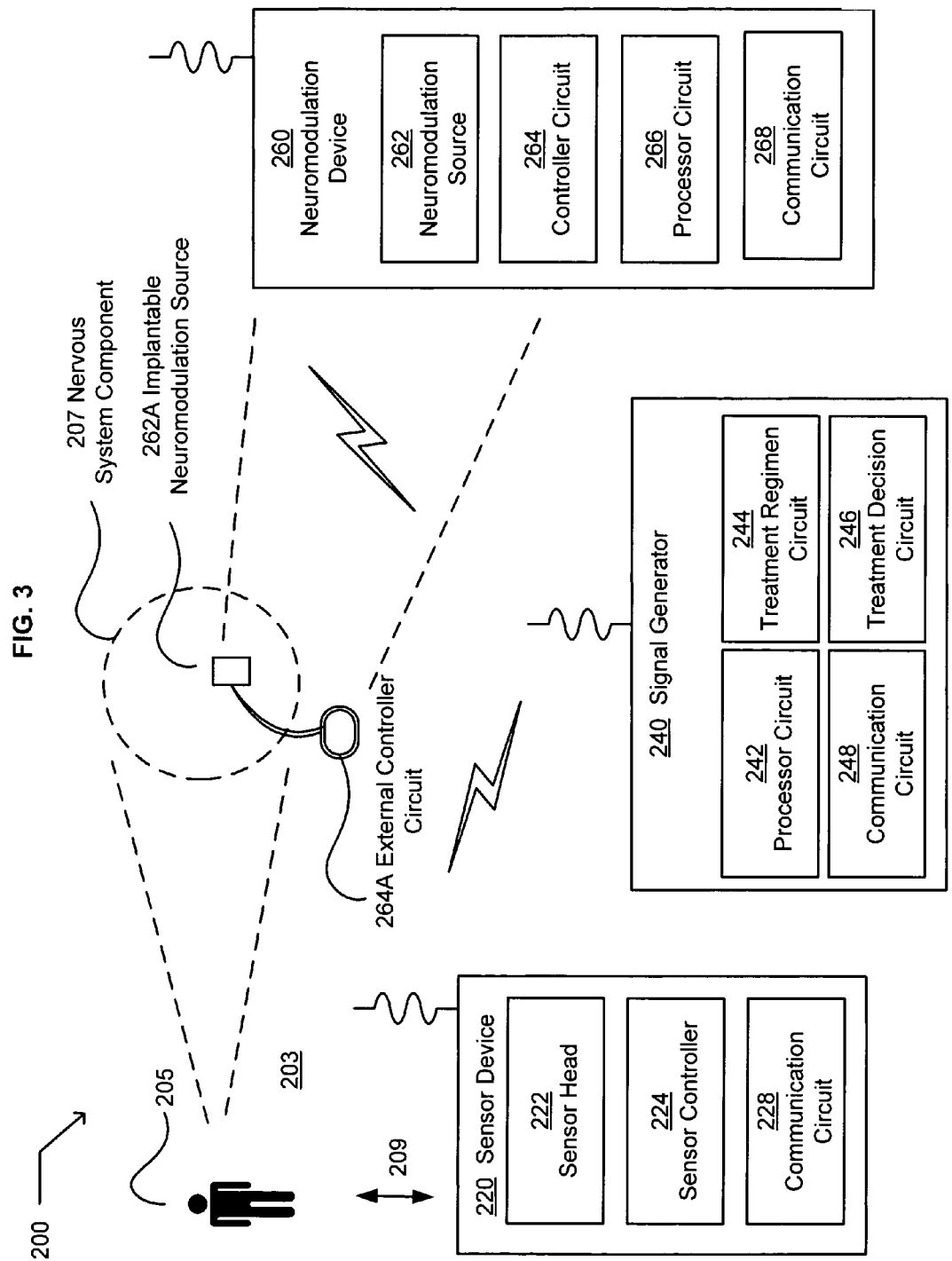
FIG. 3 illustrates an example environment in which embodiments may be implemented.

FIG. 3 illustrates an example environment 200 in which embodiments may be implemented. The example environment includes a mammal 205, illustrated by a human shape, and a system 203. The system includes a sensor device 220, a signal generator 240, and a neuromodulation device 260. The sensor device is configured to sense a property of the mammal without physically contacting the mammal. A gap between the sensor device and the mammal is illustrated by a gap 209. In an embodiment, the sensor device includes a device that detects or measures a physical property of the mammal. In an embodiment, the sensor device includes a device that detects or measures a physical property of the mammal and records, indicates, or responds to it. In an embodiment, the sensor device may include a sensor head 222, a sensor controller 224, or a communications circuit 228. In an embodiment, the communications circuit may be operable to communicate using an electrical conductor or using a wireless transmission.

The signal generator 240 includes a signal generator configured to generate a signal indicative of the sensed property of the mammal. In an embodiment, the signal may include a raw data signal, i.e., a capacitance measurement, a change in position of skin over artery in the neck, an acoustic pressure, or a brain electrical activity of the mammal 205. In an embodiment, the signal generator may include a processor circuit 242, a treatment regimen circuit 244, a treatment decision circuit 246, or a communications circuit 248. In an embodiment, the communications circuit may be operable to communicate using an electrical conductor or using a wireless transmission. In an embodiment, the signal generator may include an instance of the thin computing device 20 and the processor circuit may be the processing unit 21, as described in conjunction with FIG. 1. In an embodiment, the signal generator may include the computing device 110 and the processor circuit may be the processor 120, as described in conjunction with FIG. 2. In an embodiment, the treatment regimen circuit 244 or the treatment decision circuit 246 can be included in any of the devices—it need not be only in the signal generator 240.

The neuromodulation device 260 includes a neuromodulation device configured to output a stimulus operable to modulate a nervous system component of the mammal 207 in response to the signal indicative of the sensed property of the mammal 205 and generated by the signal generator 240. In an embodiment, the signal indicative of the sensed property of the mammal may include a processed signal indicative of the sensed property of the mammal. The processed signal may include a signal that has been subjected to a process including one or more of analyzing, sampling, correlating, filtering, modification, alteration, or conditioning by an intermediate device (not shown) after generation by the signal generator and before receipt by the neuromodulation device. In an embodiment, the signal indicative of the sensed property of the mammal may include a processed signal indicative of the sensed property of the mammal; the process including one or more of analyzing, sampling, correlating, filtering, modification, alteration, or conditioning by the neuromodulation device. In an embodiment, the stimulus includes a stimulus operable to at least one of excite, stimulate, de-stimulate, block, inhibit, or augment the nervous system component. In an embodiment, the neuromodulation device may include a neuromodulation source 262, a controller circuit 264, a processor circuit 266, or a communications circuit 268. In an embodiment, the communications circuit may be operable to communicate using an electrical conductor or using a wireless transmission. In an embodiment, the neuromodulation device may include an instance of the thin computing device 20 and the processor circuit may be the processing unit 21, as described in conjunction with FIG. 1. The neuromodulation source may include an implantable neuromodulation source 262A operable to output a stimulus. In an embodiment, an implantable neuromodulation source includes an injectable neuromodulation source. In another embodiment, the neuromodulation source may include a neuromodulation source configured to contact a peripheral portion (not shown) of the mammal and operable to output a stimulus.

In an embodiment, the sensor device 220 includes a sensor array configured to sense a property of the mammal 205 without physically contacting the mammal. For example, the sensor array may include at least two sensor heads 222. In an embodiment, the at least two sensor heads may include at least two sensor heads configured to sense the same property of the animal. In an embodiment, the at least two sensor heads may include sensor heads configured to sense different properties of the animal. For example, one sensor head may be configured to sense temperature, another sensor head configured to sense heart rate, and a further sensor head configured to sense blood pressure. In an embodiment, the sensor device includes a sensor device responsive, without physically contacting the mammal, to an impedance, capacitance, permittivity, reflectivity, absorption, or electrical activity of the mammal. For example, a sensor device including a capacitive proximity sensor element configured to sense a property of a mammal without physically contacting the mammal is described in U.S. Patent Application Pub. No. 20080246495, Detection apparatus for a capacitive proximity sensor, to S. Zarabadi et al. For example, in an embodiment, a reflection or reflectivity property may include an acoustic, light, or radio wave reflectivity. In an embodiment, the sensor device includes a sensor device responsive to the property of a mammal without physically contacting the mammal. In an embodiment, the sensor device includes a sensor device configured to sense a property of a mammal without physically contacting the mammal. In an embodiment, the property includes a property of the mammal indicative of a disease, neurological disease, disorder, nervous system disorder, heart rhythm, heart disease, medical condition, treatable condition, health condition, physiological characteristic, or sleep disorder. In an embodiment, the sensor device includes a sensor device configured to sense at least one of a quality or attribute of a mammal without physically contacting the mammal.

In an embodiment, the sensor device 220 includes a sensor device configured to sense a physiological property of the mammal 205 without physically contacting the mammal. In an embodiment, the sensor device includes a sensor device configured to sense a physiological aspect of a mammal without physically contacting the mammal. In an embodiment, the sensor device includes a sensor device configured to sense a corporeal property or a physical property of a mammal without physically contacting the mammal. In an embodiment, the sensor device includes a sensor device configured to sense a dynamic physical property of the mammal without physically contacting the mammal. For example, a dynamic physical property may include a property of a pulse rate measured over time, such as four, ten, or twenty-four hours. In another example, a dynamic physical property may include a pupil diameter measured over time. In an embodiment, the sensor device includes a sensor device configured to sense a bodily condition or physiological state property of a mammal without physically touching the mammal. For example, a bodily condition or physiological state property may include a condition or state of the body or bodily functions. In an embodiment, the sensor device includes a sensor device configured to sense a bodily condition or physiological state property of a fetus. For example, the sensor device may include a sensor device configured to sense a fetal heart rate. In an embodiment, the sensor device includes a sensor device configured to scan the gap 209 between the sensor and the mammal. In an embodiment, the sensor device includes a sensor device configured to progressively scan a space in which the mammal may be present. In an embodiment, the sensor device includes a sensor device configured to monitor a property of a mammal without physically contacting the mammal. For example, a sensor device configured to monitor a property may include a sensor device configured to observe or check the property periodically. For example, the sensor device may observe a property once each five minutes, or the sensor device may enter a sleep mode to be subsequently awakened on receipt of a command.

In an embodiment, the sensor device 220 includes a sensor device configured for an association with the mammal 205 and to sense a property of the mammal without physically contacting the mammal. In an embodiment of this sensor device, the sensor device may include a sensor device configured for a physical association with a mammal and to sense a property of the mammal without physically contacting the mammal. For example, the sensor device may be configured for an association with a chair, a pillow, or a gurney. In an embodiment of this sensor device, the sensor device may include a sensor device configured for a physical association with an article of clothing or garment wearable by a mammal and to sense a property of the mammal without physically contacting the mammal. In an embodiment of this sensor device, the sensor device may include a sensor device configured for a physical association with an object wearable by a mammal and to sense a property of the mammal without physically contacting the mammal. For example, the sensor device may be configured for a physical association with eye glasses or jewelry. For example, a sensor device configured for a physical association with an object wearable by a mammal is described by U.S. Patent Application Pub. No. 20060058694, Electrodynamic sensors and applications thereof, to T. Clark et al.; WO 2003/048789, Electrodynamic sensors and applications thereof, by T. D. Clark et al.; or C. J. Harland et al., *High resolution ambulatory electrocardiographic monitoring using wrist-mounted electric potential sensors,* 14 Meas. Sci. Technol. 923-928 (2003).

Figure 4:
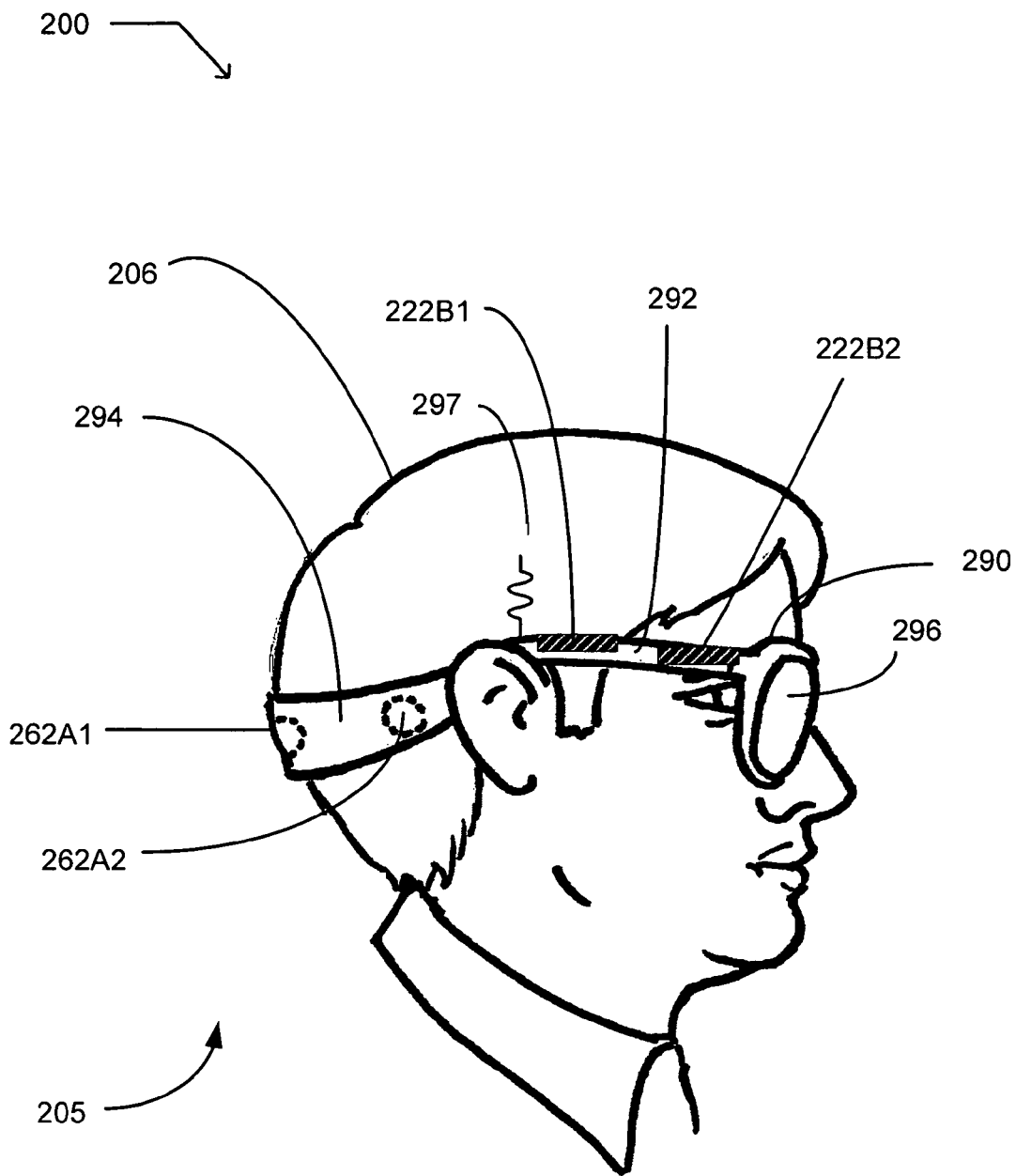
FIG. 4 illustrates another example of the environment that illustrates a head of the mammal wearing eyeglasses.

FIG. 4 illustrates another example of the environment 200. The environment includes a head 206 of the mammal 205 wearing eyeglasses 290. The eyeglasses include lens 296 and earpiece 292. Example sensor devices 222B1 and 222B2 are illustrated as physically associated with the earpiece. In an embodiment of this sensor device, the sensor device may include a sensor device configured for carrying by a mammal and to sense a property of the mammal without physically contacting the mammal. For example, the sensor device may include an electrodynamic sensor, such as described by U.S. Patent Application Pub. No. 20060058694, supra. The eyeglasses also include a communications circuit 297.

The eyeglasses 205 further include a retaining strap 294. An example neuromodulation source is illustrated as physically associated with the retaining strap. The neuromodulation source is illustrated as neuromodulation sources 262A1 and 262A2 physically associated with the retaining strap. In an embodiment, the neuromodulation sources 262A1 and 262A2 either in combination or each respectively include an external control module physically associated with the retaining strap and a scalp-mounted electrode and/or an implanted electrode (not shown). For example, a neuromodulation source including an external control module, and a scalp-mounted electrode and/or an implanted control module and electrode is described in U.S. Pat. No. 6,016,449, System for treatment of neurological disorders, to R. E. Fishell et al. For example, a neuromodulation source including an external stimulator and an implanted stimulus receiver including an electrode is described in U.S. Patent No. Application Pub. No. 20070067004, Methods and systems for modulating the vagus nerve ($10^{th}$ cranial nerve) to provide therapy for neurological and neuropsychiatric disorders, by B. R. Boveja et al. For example, a neuromodulation source including an external control module and a nonimplanted transcranial magnetic stimulator is described in U.S. Patent Application Pub. No. 20070179558, Systems and methods for varying electromagnetic and adjunctive neural therapies, by B. Gliner et al.

Returning to FIG. 3, in an embodiment, the sensor device 220 includes a sensor device configured for an association with an object and to sense a property of the mammal 205 without physically contacting the mammal. For example, the object may include a substantially fixed object. For example, the object may include a chair, table, bed, or gurney. For example, the object may include an object locatable in a space where the mammal is present and free to move. In an embodiment, the sensor device includes a sensor device configured for a mounted, placed, integrated, or embedded association with an object and to sense a property of a mammal without physically contacting the mammal. For example, the object may include a wall, chair, or pillow. In an embodiment, the sensor device includes a sensor device configured for an association with an object, and configured to sense a property of a mammal while separated from a direct contact with the mammal by an intervening material or substance. For example, the object may include a substantially fixed object. For example, the sensor device may be separated from a direct contact with the mammal by an intervening material or substance forming the gap 209 schematically illustrated in FIG. 3. For example, the sensor device may be configured to sense a property of a mammal while spaced apart by the gap from a direct contact with the mammal by an intervening material or substance. For example, the separation or gap between the sensor device and the mammal may be formed by a portion of a chair (including a chair support structure or a fabric covering the chair), gurney, pillow, bedding, or clothing worn by mammal. For example, in an embodiment, the intervening material or substance may include an intervening material or substance permitting the sensor device to sense a property of a mammal. For example, in an embodiment, the intervening material or substance may include an intervening non-conductive material or substance permitting the sensor device to sense a property of a mammal. In an embodiment, the intervening material or substance does not include a conducting substance, such as an ultrasound gel or an electrically conductive material. An example of a sensor device configured for an association with an object, and configured to sense a bioelectric field or a bioelectric signal of a mammal while separated from a direct contact with the mammal by an intervening material or substance is described in U.S. Pat. No. 7,245,956, Unobtrusive measurement system for bioelectric signals, to R. Matthews et al.

In an embodiment, the sensor device 220 includes a sensor device configured to sense a property of the mammal 205 without physically touching the mammal. In an embodiment, the sensor device includes a sensor device configured to sense a property of a mammal without a resistive contact with the mammal. In an embodiment, the sensor device includes a sensor device configured to sense a property of a mammal without an electrically conductive contact with the mammal. In an embodiment, the sensor device includes a sensor device configured to sense a property of a mammal across a non-electrically conductive gap 209 with the mammal. In an embodiment, the sensor device includes an electrodynamic sensor device configured to sense an electrical activity of the heart of a mammal without physically contacting the mammal. For example, the electrodynamic sensor may be configured to sense a heart rate, electrical activity of the heart, such as electrocardiography (ECG), or conductivity. An example of an high input impedance electrodynamic sensor device configured to sense an electrical activity of a heart of a mammal without physically contacting the mammal is described in U.S. Patent Application Pub. No. 20060058694; WO 2003/048789, supra; Electrodynamic sensors and applications thereof, to T. Clark et al. In an embodiment, the sensor device includes an adaptive electric potential sensor device configured to sense a property of a mammal without physically contacting the mammal. An example of an adaptive electric potential sensor device configured to sense a property of a mammal without physically contacting the mammal is described in R. L. Prance et al., *Adaptive Electric Potential Sensors for smart signal acquisition and processing,* 76 Journal of Physics: Conference Series, 012025 (2007). In an embodiment, the sensor device includes an electric potential probe sensor device configured to sense a property of a mammal without physically contacting the mammal. An example of an electric potential probe sensor device configured to sense a body electrical activity or signals, such as for example arterial pulse or other body electrodynamics, of a mammal without physically contacting the mammal is described in C. J. Harland et al., *Electric potential probes—new directions in the remote sensing of the human body*, 13 Meas. Sci. Tech. 163-169 (2002). In an embodiment, the sensor device 220 and the signal generator 240 share at least a portion of a common chassis. In an embodiment, the sensor device and the signal generator do not share a common chassis.

In an embodiment, the sensor device 220 of FIG. 3 includes a sensor device configured to sense at least one of an electrical, acoustic, thermal, radiative, absorption, reflection, gaseous emission, or transmissibility property of the mammal without physically contacting the mammal. In an embodiment, a thermal property may include an infrared measured thermal property. In an embodiment, a thermal property may include microwave length (3-30 cm) electromagnetic radiation naturally emitted by the mammal, for example, as described in V. Troitskii et al., *Intrinsic microwave radiation from the human body*, Radiophysics Scientific-Research Institute (Translated from Izvestiya Vysshtkh Uchebnykh Zavedenii, Radiofizilm, Vol. 24, No. 1, pp. 118-121, January, 1981. For example, a sensor device configured to sense a thermal property of the mammal includes a microwave radiometer operable to measure natural electromagnetic radiation from the mammal's internal tissue in the microwave range. In an embodiment, the microwave radiometer may be combined with an infrared sensor as described in R. Avagyan et al., *New diagnostic methods in acupuncture*, ICMART '99 International Medical Acupuncture Symposium 7, Riga, (May 21-23, 1999). See also, Pub. No. WO 2006/091123 (PCT/RU2006/000072), Microwave radio thermograph, to V. Hokkanen. For example, a transmissibility property may include a light or radio wave transmissibility property. For example, in an embodiment, a radiative property may include gammas or other types of radiation emitted by the body of the mammal itself, for example potassium 40. An embodiment of a gamma-ray sensor device configured to sense a property of a mammal without physically contacting the mammal is expected to be provided by the Radtell™ passive gamma-ray sensor by Oak Ridge National Laboratory of Oak Ridge, Tenn.

In an embodiment, the signal generator 240 is further configured to determine if treatment is indicated in response to the sensed property of the mammal. In an embodiment, another device may be configured to determine if treatment is indicated, and to output that determination to the signal generator. The signal generator is also configured, if a treatment is indicated, to output a signal indicative of the sensed property of the mammal.

In an embodiment, the neuromodulation device 260 of FIG. 3 includes a neuromodulation device configured for implantation in the mammal 205, for example, such as illustrated by implantable neuromodulation source 262A. In an embodiment, the neuromodulation device includes a neuromodulation device configured for implantation in the mammal. The neuromodulation device is also configured to output a stimulus operable to modulate a nervous system component 207 of the mammal in response to the signal indicative of the sensed property of the mammal. In an embodiment, the neuromodulation device includes a neuromodulation device configured for a physical contact with the mammal. The neuromodulation device is also configured to output a stimulus operable to modulate a nervous system component of the mammal in response to the signal indicative of the sensed property of the mammal. In an embodiment, the neuromodulation device includes a neuromodulation device configured for a physical association with the mammal. The neuromodulation device is also configured to output a stimulus operable to modulate a nervous system component of the mammal in response to the signal indicative of the sensed property of the mammal. In an embodiment, the neuromodulation device includes a neuromodulation device configured for a positioning proximate to the mammal. The neuromodulation device is also configured to output a stimulus operable to modulate a nervous system component of the mammal in response to the signal indicative of the sensed property of the mammal.

In an embodiment, the neuromodulation device 260 of FIG. 3 includes a neuromodulation device configured to output an ultrasonic stimulus operable to modulate a nervous system component of the mammal in response to the signal indicative of the sensed property of the mammal. A system and method employing ultrasonic stimulation is described in U.S. Patent Application Pub. No. 20070191906, Method and apparatus for selective nerve stimulation, by A. Iyer et al.; W. Tyler et al., *Remote Excitation of Neuronal Circuits Using Low-Intensity, Low-Frequency Ultrasound*, 3(10) PLoS ONE e3511 (2008). In an embodiment, the neuromodulation device includes a neuromodulation device configured to output an ultrasonic wave stimulus in a presence of a magnetic field that is operable to modulate a nervous system component of the mammal in response to the signal indicative of the sensed property of the mammal. A system and method employing an ultrasonic wave stimulus in a presence of a magnetic field is described in S. Norton, *Can ultrasound be used to stimulate nerve tissue*? BioMedical Engineering OnLine (Mar. 4, 2003).

In an embodiment, the neuromodulation device 260 includes a neuromodulation device configured to output a magnetic stimulus operable to modulate a nervous system component of the mammal in response to the signal indicative of the sensed property of the mammal, for example to provide transcranial stimulation to a nervous system component. A system and method employing transcranial magnetic stimulation is described in U.S. Patent Application Pub. No. 20070179558, supra; and M. Massimini et al., *Triggering sleep slow waves by transcranial magnetic stimulation*, 104 (20) PNAS 8496 (May 2007).

In an embodiment, the neuromodulation device 260 includes a neuromodulation circuit configured to output a stimulus operable to modulate a nervous system component 207 of the mammal 205 in response to the signal indicative of the sensed property of the mammal. In an embodiment, the neuromodulation device includes a neuromodulation mechanism configured to output a stimulus operable to modulate a nervous system component of the mammal in response to the signal indicative of the sensed property of the mammal. In an embodiment, the neuromodulation device includes a neuromodulation device configured to output a stimulus operable to modulate a central nervous system component, a sensory nerve, a motor nerve, an autonomic nervous system component, or an enteric nervous system component of the mammal in response to the signal indicative of the sensed property of the mammal.

In an embodiment, the neuromodulation device 260 includes a neuromodulation device configured to output a stimulus operable to modulate a neurotransmitter-releasing component of the nervous system of the mammal in response to the signal indicative of the sensed property of the mammal. In an embodiment, the neuromodulation device includes a neuromodulation device configured to output a stimulus operable to modulate a nervous system component of the mammal in response to the signal indicative of the sensed property of the mammal. In an embodiment, the stimulus if delivered to the mammal is configured to excite, stimulate, enhance, alter, mediate, modify, inhibit, block, negate, or augment the nervous system component of the mammal. In an embodiment, the neuromodulation device includes a neuromodulation device configured to output a stimulus operable to at least one of excite, stimulate, enhance, alter, mediate, modify, inhibit, block, negate, or augment an aspect of the nervous system of the mammal in response to the signal indicative of the sensed property of the mammal. In an embodiment, the stimulus includes a stimulus operable to directly or indirectly affect a signal sent from or via a nerve.

In an embodiment, the mammal 205 includes a fetus. In an embodiment, the mammal includes a human being. In an embodiment, the human being includes a fetus. In an embodiment, the mammal includes a living organism that is distinguished from plants by independent movement and responsive sense organs.

In an embodiment, a system described herein, such as the system 203 described herein, or a method described herein, may be used to treat a health condition affecting the heart of the mammal 205. In an embodiment the sensor device 220 may sense heartbeat intervals and ECG readings remotely by measuring small electrical potentials using a high input impedance electrometer. An example of such a sensor device is described in U.S. Patent Application Pub. No. 20060058694, supra; WO 2003/048789, supra; Harland, Meas. Sci. Technol., supra; Prance, 2007 Journal of Physics: Conference Series, supra. Such sensor devices are expected to provide noninvasive and remote monitoring. In an embodiment, the sensor device 220 may be worn by the mammal in or on clothing or jewelry, such as in wrist bands, and may be in non-conductive contact with the body. For example, as described by U.S. Patent Application Pub. No. 20060058694, supra; WO 2003/048789, supra; C. J. Harland et al., *High resolution ambulatory electrocardiographic monitoring using wrist-mounted electric potential sensors*, 14 Meas. Sci. Technol. 923-928 (2003). In an embodiment, the sensor device 220 may be included in or associated with a piece of furniture, such as a chair or desk, or electronics such as a personal computer, or with some other item within, e.g., one meter from the mammal. In an embodiment, the sensor device 220 able to measure electric potentials may be embedded in objects, such as a bed or chair, in direct but non-conductive contact with the mammal. For example, as described by U.S. Pat. No. 7,245,956, supra. In an embodiment, the sensor device 220 may sense heartbeat intervals and electrocardiographic information by examining physiologic activity of the mammal or its organs and may be operable to sense a property of the mammal 205 in response to an electromagnetic signal sent at or illuminating the mammal and reflected from the mammal. In an embodiment, the illuminating may include exposing, subjecting, or directing energy at the mammal. Systems using illuminating or reflected electromagnetic signals, including radiofrequency (RF) or microwave signals, are described in U.S. Pat. No. 7,272,431, Remote-sensing method and device to W. McGrath; U.S. Patent Application Pub. No. 20040123667, Remote-sensing method and device, by W. McGrath; or U.S. Patent Application Pub. No. 20080045832, Remote-sensing method and device, by W. McGrath. In an embodiment, one or more sensor device 220, which may be or include a sensor array, may be deployed, for example, throughout a room, perhaps as part of a smart room network, so as to monitor the mammal at rest or in motion.

In an embodiment, information gathered by the sensor device 220 and processed by the signal generator 240 may be communicated to a computer. In an embodiment, information may be communicated to a computer of the system electronically. In an embodiment, information may be communicated to a computer of the system wirelessly, for example using radio waves or ultrasound waves, or Bluetooth technology. In an embodiment, a computer, such as the thin computing device 20 described in conjunction with FIG. 1 or the computing device 110 described in conjunction with FIG. 2 may be used to process the information. The computer may be part of a network. The processing may include application of a computer program or input from a user, for example the mammal or a health care provider. If observations are determined by the computer or user to constitute a pathology, the system 203 or user can initiate a neuromodulation treatment.

In an embodiment, a system described herein, such as the system 203 described herein, or a method described herein, may be used to provide a neuromodulation, such as a neuromodulation current, to a vagus nerve or related fiber by the neuromodulation source 262, which may initiate a stimulating action potential; in some forms the neuromodulation may block an action potential. In an embodiment, the system 203 may provide a stimulus or blocking neuromodulation to a vagal nerve. In an embodiment, the neuromodulation device 260 may be configured to be partially or completely implanted. In an embodiment, a neuromodulation device 260 may be responsive to instructions transmitted from a computer or via network. In an embodiment, the instructions may be generated by the treatment regimen circuit 244 or the treatment decision circuit 246. In an embodiment, at least a portion of an implantable neuromodulation device 260, such as the neuromodulation source 262, may be placed within a blood vessel near a nerve and able to stimulate the nerve. For example, as described in U.S. Patent Application Pub. No. 20050187584, Vagal nerve stimulation using vascular implanted devices for treatment of atrial fibrillation, by S. Denker et al.; or U.S. Patent Application Pub. No. 20060259085, Neural stimulation system with pulmonary artery lead, by Y. Zhang.

In an embodiment, a treatment may include a computer or network programmable to communicate instructions wirelessly with one or more partial or completely implanted neuromodulation devices 260. In an embodiment, a treatment may include the computer or network responsive to commands from the user through a user input interface, such as a user interface of the thin computing device described in conjunction with FIG. 1, or a user interface such as the user interface 160 described in conjunction with FIG. 2. In an embodiment, the computer may provide an indicator, such as an audio or visual indicator or a report to the mammal, or provide instructions to the mammal or a third-party user of the computer. In an embodiment, a computing device, having processed the information from the remote sensor device 220 or signal generator 240 as part of its programming or as instructed to do so by a user, may send out a radio signal to a receiver, such as the communication circuit 268, associated with the implantable neuromodulation source. For example, as described in U.S. Patent Application Pub. No. 20070191906, Method and Apparatus for Selective Nerve Stimulation, by A. Iyer.

Figure 5:
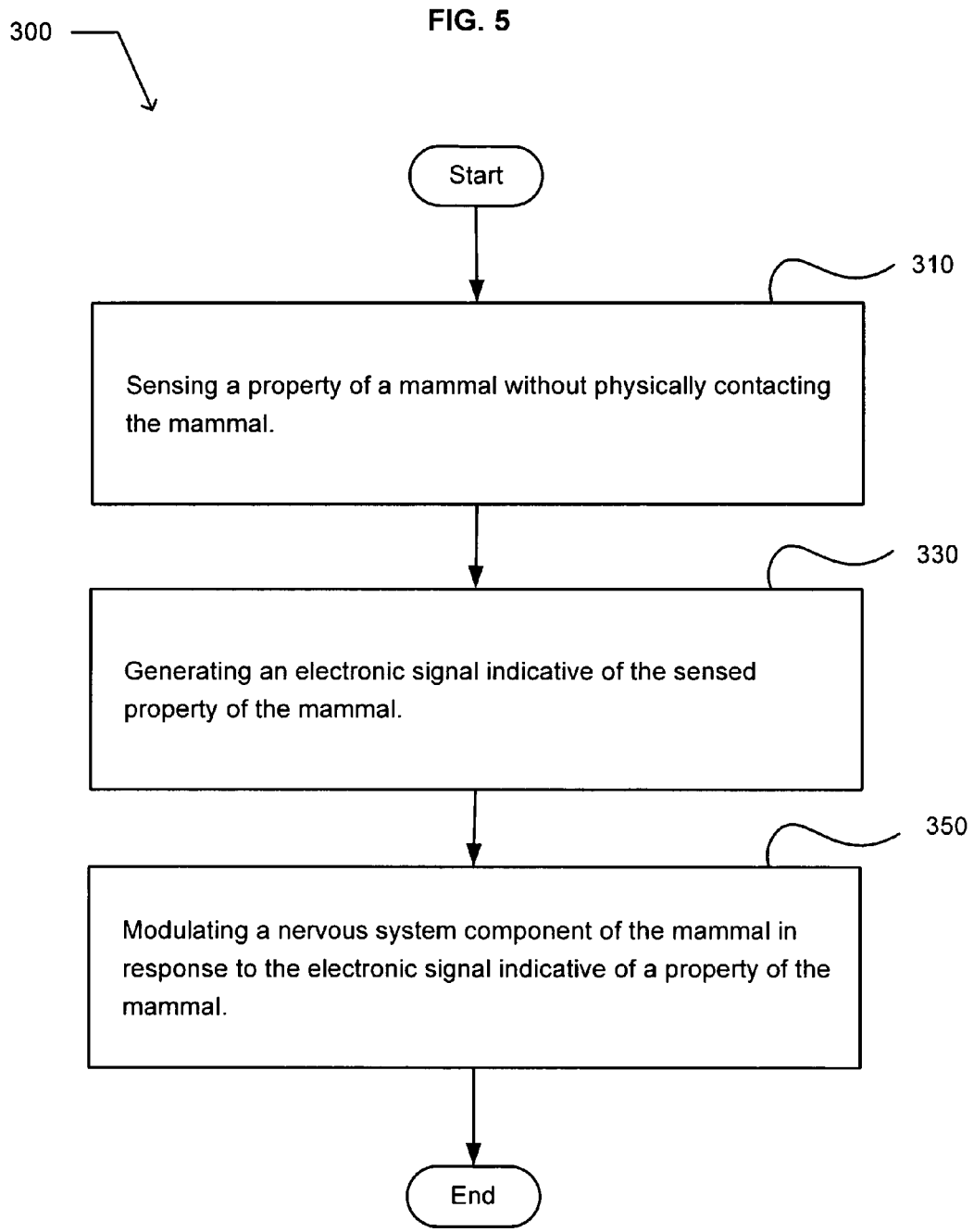
FIG. 5 illustrates an example operational flow in which embodiments may be implemented.

In an embodiment, a system described herein, such as the system 203 described in conjunction with FIG. 3, or a method described herein, such as the operational flow 300 described in conjunction with FIG. 5, may utilize a type of neuromodulation device in which a portion, such as a controller, illustrated in FIG. 3 as the external controller circuit 264A, may be external to the body of the mammal 205 and electronically coupled with the computer or network. In an embodiment, the external controller circuit may be a transcutaneous controller. In an embodiment, the external controller circuit may be programmed to accept information or instructions from the computer, network, or remote detector and, in response to transmit a signal to the implantable neuromodulation source 262A, which then stimulates or blocks a vagus nerve or fiber. In an embodiment, a wireless transmission to an external controller circuit 264A may also serve as a means of powering an implantable neuromodulation source such as the implantable neuromodulation source 262A.

In an embodiment, a system described herein, such as the system 203, or a method described herein, may use the neuromodulation device 260 with at least two capabilities. The neuromodulation device may provide two or more similar or different stimuli separated temporally. The neuromodulation device may provide a second signal that influences a first signal or its effects. Examples of such capabilities are described in U.S. Patent Application Pub. No. 20080091241, Vagal stimulation for cardioversion of atrial fibrillation, by O. Ben-Ezra et al; U.S. Patent Application Pub. No. 20080125825, Therapeutic maintenance of atrial fibrillation by electrical stimulation, by T. David; U.S. Patent Application Pub. No. 20040193231, Selective nerve fiber stimulation for treating heart conditions, by T. David; U.S. Patent Application Pub. No. 20080125827, Selective nerve fiber stimulation for treating heart conditions, by T. David; U.S. Patent Application Pub. No. 20060271115, Vagal stimulation for anti-embolic therapy, by O. Ben-Ezra et al; or U.S. Pat. No. 7,321,793, Vagal stimulation for atrial fibrillation therapy, by O. Ben-Ezra et al. In an embodiment, a computer may be programmed to continue monitoring via the remote sensor device 220 and the signal generator 240, and may send different or additional instructions to the neuromodulation device. In an embodiment, additional neuromodulation devices 260 may be used to affect additional nerves, e.g. such as efferent or afferent to the vagus nerves, sympathetic nerves, myogenic tissue, or myocardial tissue. In an embodiment, monitoring the mammal 205 via the sensor device 220 may continue during and following treatment, and the treatment may be adjusted accordingly as determined by a computer program or a user input. In an embodiment, the neuromodulation device, perhaps as part of the controller 264, may report information to a computer regarding the neuromodulation treatment provided, for example the type and duration of stimulation applied to a vagus nerve.

In an embodiment, a system, such as the system 203 described herein, or a method described herein, may be used to treat a sleep disorder or an effect thereof. In an embodiment, the sensor device 220 may include a pupillometer. An example of a pupillometer sensor device using a camera or infrared optics is described in U.S. Pat. No. 6,097,295, Apparatus for determining the alertness of a driver, to M. Griesinger et al.; or U.S. Pat. No. 7,226,164, Method and apparatus for testing sleepiness, to M. Griesinger et al. In an embodiment, a sensor device including a pupillometer may be incorporated into a computer monitor or the dashboard of a vehicle. In an embodiment, a sensor device may be configured to scan the pupils of an individual facing the monitor or dashboard, perhaps at programmed intervals.

In an embodiment, the sensor device 220 may be configured to obtain electroencephalography (EEG) readings by measuring small electrical potentials using a high input impedance electrometer. Examples using one or more sensor devices and technologies are described in U.S. Patent Application Pub. No. 20060058694 supra; WO 2003/048789, supra; C. J. Harland et al, *Remote detection of human electroencephalograms using ultrahigh input impedance electric potential sensors* 81(17) Appl. Phys. Letters, 3284-3286 (2002); or R. J. Prance et al., *Adaptive Electric Potential Sensors for smart signal acquisition and processing*, 76 Journal of Physics: Conference Series 012025 (2007).

In an embodiment, the sensor device 220 may include an electromagnetic inductance sensor device. An example of an electromagnetic inductance sensor device is described in U.S. Pat. No. 7,254,439, Method and system for contactless evaluation of fatigue of an operator, to D. Misczynski. In an embodiment, the sensor device 220 may include an electromagnetic signal sensor device may be used. An example of an electromagnetic signal sensor device is described in U.S. Pat. No. 7,272,431, Remote-sensing method and device, to W. McGrath; U.S. Patent Application Pub. No. 20040123667, supra; or U.S. Patent Application Pub. No. 20080045832, supra. In an embodiment, one or more sensor device 220 may be arranged as an array, embedded in a number of items, or within a defined area, for example a vehicle or room.

In an embodiment, the implantable neuromodulation device 260 may include of multiple electrodes, which in some embodiments may be quite small. For example, see U.S. Pat. No. 5,540,734, Cranial nerve stimulation treatments using neurocybernetic prosthesis, to J. Zabara; or U.S. Pat. No. 7,167,751, Method of using a fully implantable miniature neurostimulator for vagus nerve stimulation, to T. Whitehurst et al. In an embodiment, the implantable neuromodulation device 260 may be a subcutaneous injectable neuromodulation device. Examples of subcutaneous injectable neuromodulation sources include the SAINT™ system by MicroTransponder of Dallas, Tex., which is described as including an arrangement of injectable neuromotransponder devices and eliminating any implantable battery or wires. MicroTransponder's SAINT system neuromotransponder devices are injectable with a 12-gauge needle in an outpatient procedure. MicroTransponder describes that its SAINT system will be coupled to an external controller, which can be worn like an armband; and will provide the power and stimulus parameters for the device. The external controller will be able to interface with a laptop or PDA in order to change the stimulus parameters to better treat the patient's pain profile. An example of injectable microtransponders is described in http://www.microtransponder.com/technology/index.html (accessed May 18, 2009); *Tiny Implants for Treating Chronic Pain*, Technology Review (May 15, 2009) http://www.technologyreview.com/biomedicine/22657/?nlid=2032 (accessed May 18, 2009); U.S. Patent Application Pub. No. 20090157147 Implantable Transponder Systems and Methods by L. Cauller and R. Weine; and U.S. Pub. App. No. 20080319506, Grooved electrode and wireless microtransponder system, by L. Cauller.

In an embodiment, a system described herein, such as the system 203, or a method described herein, may include modulating the autonomic nervous system. In an embodiment, the system or method may provide a treatment that includes stimulating or inhibiting the autonomic nervous system via a nerve pathway or by stimulating the spinal cord via an implanted or transcutaneous device. An example is described in U.S. Pat. No. 7,149,574, Treatment of conditions through electrical modulation of the autonomic nervous system, to A. Yun et al.; or U.S. Pat. No. 7,155,278, Neurostimulation to treat effects of sleep apnea, to G. King et al. In an embodiment the system or method may provide a treatment that may include stimulation of a targeted nerve such as the phrenic nerve as described in U.S. Pat. No. 7,340,302, Treating sleep apnea in patients using phrenic nerve stimulation, to E. Falkenberg et al., perhaps to directly affect a physiologic system such as respiration.

FIG. 5 illustrates an example operational flow 300. After a start operation, the operational flow includes a remote detection operation 310. The remote detection operation includes sensing a property of a mammal without physically contacting the mammal. In an embodiment, the remote detection operation may be implemented using the sensor device 220 described in conjunction with FIG. 3. A mammal information operation 330 includes generating an electronic signal indicative of the sensed property of the mammal. In an embodiment, the mammal information operation may be implemented using the neuromodulation device 260 described in conjunction with FIG. 3. A treatment operation 350 includes modulating a nervous system component of the mammal in response to the electronic signal indicative of a property of the mammal. In an embodiment, the modulating a nervous system component of the mammal in response to the electronic signal indicative of a property of the mammal includes substantially transforming a physiological aspect of the mammal by modulating a nervous system component of the mammal in response to the electronic signal indicative of a property of the mammal. In an embodiment, the substantially transforming a physiological aspect of the mammal may include firing an extra neuron, causing a cascade of neurons, increasing or decreasing a pulse rate, reducing an abnormal heart rhythm, stopping a seizure, or effecting a cellular activity. In an embodiment, the treatment operation may be implemented using the neuromodulation device 260 described in conjunction with FIG. 3. The operational flow includes an end operation.

Figure 6:
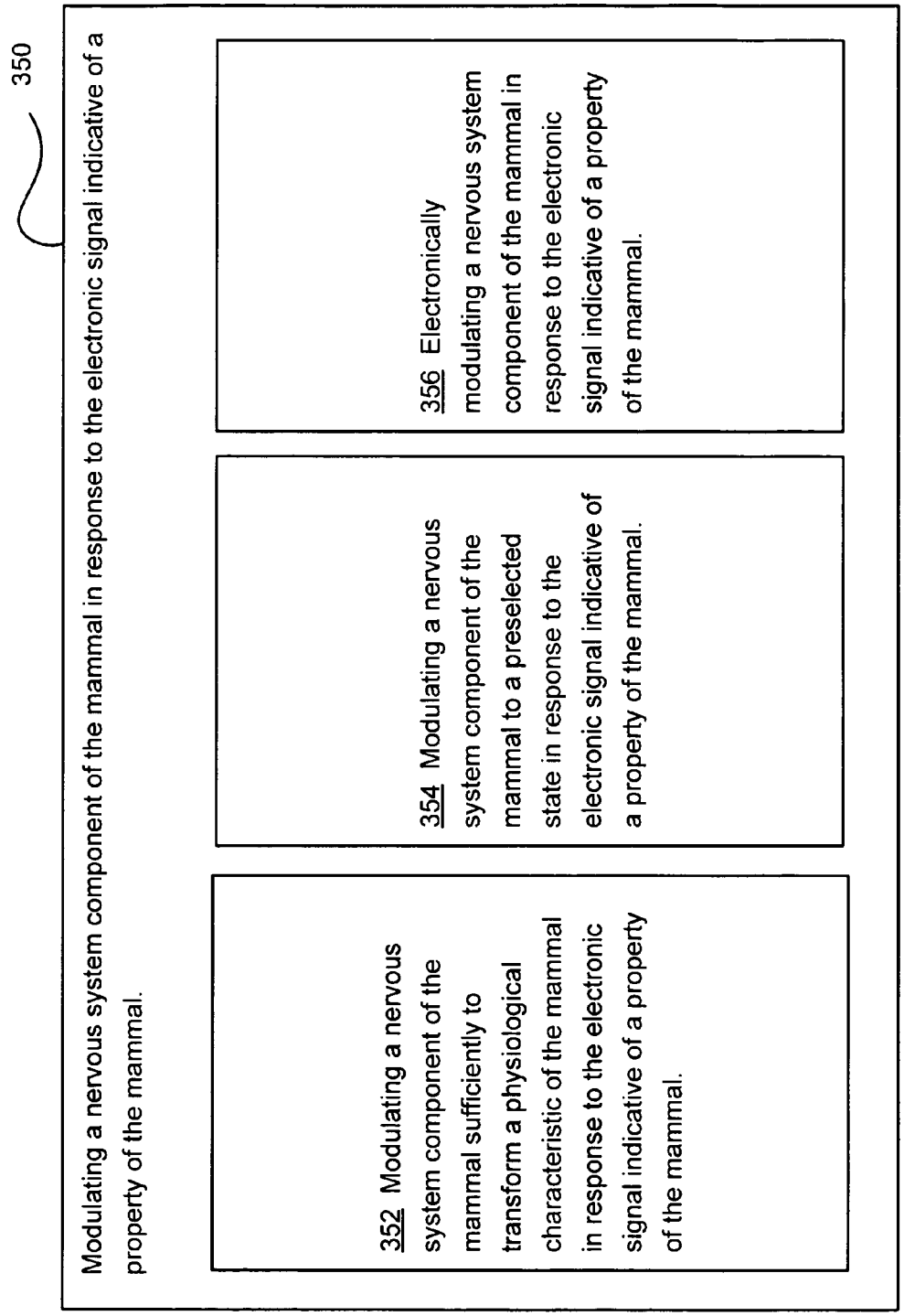
FIG. 6 illustrates an alternative embodiment of the operational flow of FIG. 5.

FIG. 6 illustrates an alternative embodiment of the operational flow 300 of FIG. 5. The treatment operation 350 may include at least one additional operation. The at least one additional operation may include an operation 352, an operation 354, or an operation 356. The operation 352 includes modulating a nervous system component of the mammal sufficiently to transform a physiological characteristic of the mammal in response to the electronic signal indicative of a property of the mammal. In an embodiment, "sufficiently to transform a physiological characteristic of the mammal" may include a treatment of a disease, disorder, or condition sufficiently to transform a physiological characteristic of the mammal. The operation 354 includes modulating a nervous system component of the mammal to a preselected state in response to the electronic signal indicative of a property of the mammal. The operation 356 includes electronically modulating a nervous system component of the mammal in response to the electronic signal indicative of a property of the mammal.

Figure 7:
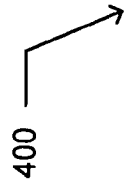
FIG. 7 illustrates an example apparatus in which embodiments may be implemented.

FIG. 7 illustrates an example apparatus 400. The apparatus includes means 410 for sensing a property of a mammal without physically contacting the mammal. The apparatus also includes means 420 for generating an electronic signal indicative of the sensed property of the mammal. The apparatus includes means 430 for modulating a nervous system component of the mammal in response to the electronic signal indicative of a property of the mammal.

FIG. 8 illustrates an example environment 500. The environment includes a system 503. The system includes a sensor device 520 configured to sense a property of a subject mammal 201 without physically contacting the subject mammal. The system includes a signal generator 540 configured to generate a signal indicative of the sensed property of the subject mammal. The system includes a patient confirmation device 580 configured to determine a substantial likeness between the subject mammal and a patient mammal, illustrated as the mammal 205, and sometimes referred to herein as the patient mammal 205. In an embodiment, a substantial likeness includes a substantial similarity. In an embodiment, a substantial likeness includes an identicality. The system includes a neuromodulation device 560 configured to output a stimulus operable to modulate a nervous system component of the patient mammal. The stimulus is selected in response to the signal indicative of the sensed property of the subject mammal. The stimulus is output only if the patient confirmation device determines a substantial likeness between the subject mammal and the patient mammal. In an embodiment, the neuromodulation device is configured to contact or touch the patient mammal. In an embodiment, at least a portion of the neuromodulation device is configured for implantation in the patient mammal, such as illustrated by implantable neuromodulation source 562A.

In an embodiment, the patient confirmation device 580 includes a patient confirmation device configured to determine a substantially common quality or aspect of the subject mammal and the patient mammal. For example, a substantially common quality or aspect may be indicated by a facial recognition algorithm. For example, a substantially common quality or aspect may be indicated by a substantially common physical profile, such as height, weight, age, or sex. For example, a substantially common quality or aspect may be indicated by a biometric technique. In an embodiment, the patient confirmation device includes a patient confirmation device operable to determine that the subject mammal and a patient mammal have a substantial probability of being the same mammal. For example, a substantial probability of being the same mammal may include an absence of any another mammal in a space in which the patient mammal is present. For example, a substantial probability of being the same mammal may include absence of any another mammal in a sensing range of the sensor device 520. For example, a substantial probability of being the same mammal may include a proximity between the sensor device and the neuromodulation device 560. In an embodiment, the patient confirmation device includes a patient confirmation device operable to determine a selfsameness between the subject mammal and a patient mammal. For example, a selfsameness between the subject mammal and a patient mammal may include receipt of identifying information from an RFID tag associated with the patient mammal.

FIG. 9 illustrates an example operational flow 600. After a start operation, the operational flow includes a remote detection operation 610. The remote detection operation includes sensing a property of a subject mammal without physically contacting the subject mammal. In an embodiment, the remote detection operation may be implemented using the sensor device 520 described in conjunction with FIG. 8. A mammal information operation 620 includes generating an electronic signal indicative of the sensed property of the subject mammal. In an embodiment, the mammal information operation may be implemented using the signal generator 540 described in conjunction with FIG. 8. A confirmation operation 630 includes determining a substantial likeness between the subject mammal and a patient mammal. In an embodiment, the confirmation operation may be implemented using the patient confirmation device 580 described in conjunction with FIG. 8. A treatment operation 640 includes outputting a neuromodulation treatment regimen to a nervous system component of the patient mammal. The neuromodulation treatment regimen determined in response to the signal indicative of the sensed property of the subject mammal. The neuromodulation treatment regimen is outputted only if a substantial likeness between the subject mammal and the patient mammal is determined. In an embodiment, the treatment operation may be implemented using the neuromodulation device 560 described in conjunction with FIG. 8. In an embodiment, the treatment operation 640 includes substantially transforming a physiological aspect of the patient animal by outputting the neuromodulation treatment regimen to a nervous system component of the patient mammal. The operational flow includes an end operation.

In an embodiment, a neuromodulation treatment regimen may include an outputted ultrasound waveform having a frequency, amplitude, or duration. In an embodiment, a neuromodulation treatment regimen may include an outputted electrical current having a frequency, amplitude, or duration. In an embodiment, a neuromodulation treatment regimen may include an outputted stimulus having a frequency, amplitude, or duration. In an embodiment, a neuromodulation treatment regimen may include at least two instances of an outputted stimulus, each instance having a respective frequency, amplitude, or duration. In an embodiment, a neuromodulation treatment regimen may include at least two respective instances of outputted stimulus, each instance having a frequency, amplitude, or duration. In an embodiment, a neuromodulation treatment regimen may include at least two sequential respective instances of an outputted stimulus, each instance having a different frequency, amplitude, or duration.

FIG. 10 illustrates an example apparatus 700. The apparatus includes means 710 for sensing a property of a subject mammal without physically contacting the subject mammal. The apparatus includes means 720 for generating an electronic signal indicative of the sensed property of the subject mammal. The apparatus includes means 730 for determining a substantial likeness between the subject mammal and a patient mammal. The apparatus includes means 740 for outputting a neuromodulation treatment regimen to a nervous system component of the patient mammal. The neuromodulation treatment regimen is determined in response to the signal indicative of the sensed property of the subject mammal. The neuromodulation treatment regimen is outputted only if a substantial likeness between the subject mammal and the patient mammal is determined.

Figure 11:
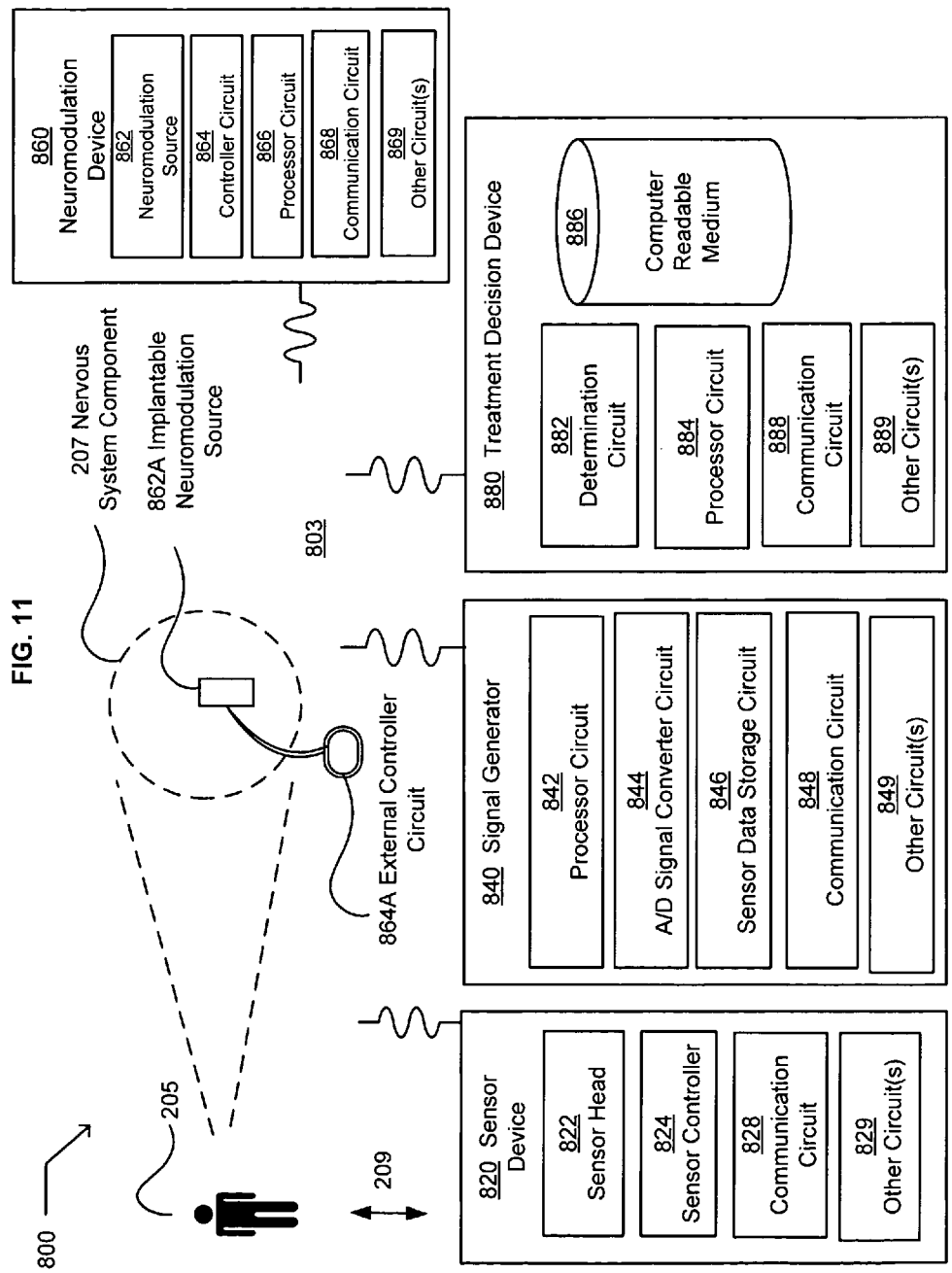
FIG. 11 illustrates an example environment in which embodiments may be implemented.

FIG. 11 illustrates an example environment 800. The example environment includes a system 803. The system includes a sensor device 820 configured to sense a property of the mammal 205 without physically contacting the mammal. In an embodiment, the sensor device may include a sensor head 822, a sensor controller 824, a communications circuit 828, or other circuit(s) 829. The system includes a signal generator 840 configured to generate a signal indicative of the sensed property of the mammal. The signal generator may include a processor circuit 842, an A/D signal converter circuit 844, a sensor data storage circuit 846, a communications circuit 848, or other circuit(s) 849. In an embodiment, the signal generator may include an instance of the thin computing device 20 and the processor circuit may be the processing unit 21, as described in conjunction with FIG. 1. In an embodiment, the signal generator may include the computing device 110 and the processor circuit may be the processor 120, as described in conjunction with FIG. 2.

The system 803 includes a treatment decision device 880 configured to determine in response to the signal indicative of the sensed property of the mammal 205 a neuromodulation treatment regimen for administration to a nervous system component 207 of the mammal. In an embodiment, the treatment decision device may include a determination circuit 882, a processor circuit 884, a computer-readable medium, a communications circuit 888, or other circuit(s) 889. In an embodiment, the treatment decision device may include an instance of the thin computing device 20 and the processor circuit may be the processing unit 21, as described in conjunction with FIG. 1. In an embodiment, the treatment decision device may include the computing device 110 and the processor circuit may be the processor 120, as described in conjunction with FIG. 2. The computer-readable medium is configured to maintain and to provide access to information corresponding to the determined neuromodulation treatment regimen. In an embodiment, the computer-readable medium includes the computer-readable medium 886 associated with the treatment decision device. In another embodiment, the computer-readable medium may include a computer-readable medium not associated with the treatment decision device.

In an embodiment, the treatment decision device 880 includes a treatment decision device configured to determine, in response to the signal indicative of the sensed property of the mammal 205 a selected outcome-promoting neuromodulation treatment regimen for administration to a nervous system component 207 of the mammal. For example, the selected-outcome may include at least one of at least one of a selected efficacious, a health-related, a quality-of-life promoting, or a health-promoting outcome. In an embodiment, the treatment decision device includes a treatment decision device configured to determine a neuromodulation treatment regimen for administration to a nervous system component of the mammal at least partially based upon the signal indicative of the sensed property of the mammal and a reference database of neuromodulation treatment regimens. The reference database may be stored by the computer-readable medium 886. In an embodiment, the reference database of neuromodulation treatment regimens includes a standard practice guideline database, an investigational practice guideline database, or neuromodulation treatment regimen database personalized to the mammal. In an embodiment, the treatment decision device includes a treatment decision device utilizing an algorithm configured to determine a neuromodulation treatment regimen for administration to a nervous system component of the mammal. The algorithm is based at least partially on the signal indicative of the sensed property of the mammal and a reference database of neuromodulation treatment regimens. The algorithm may be stored by the computer-readable medium. In an embodiment, the treatment decision device includes a treatment decision device configured to determine in response to the signal indicative of the sensed property of the mammal a neuromodulation treatment regimen for administration to a nervous system component of the mammal. The determination is based on at least one of an electronically stored database relating sensed properties of the mammal and neuromodulation treatment regimens, a computer-implemented decision table, a digitally maintained neuromodulation treatment regimen table, or a digital library correlating sensed properties of the mammal and neuromodulation treatment regimens.

In an embodiment, the treatment decision device 880 includes a treatment decision device configured to determine in response to the signal indicative of the sensed property of the mammal 205 a neuromodulation treatment regimen for administration to a nervous system component 207 of the mammal based upon a look-up table of stimuli regimens to be administered to a nervous system component of the mammal according to a selected outcome. The look-up table may be stored by the computer-readable medium 886. In an embodiment, the treatment decision device includes a treatment decision device configured to determine in response to the signal indicative of the sensed property of the mammal a neuromodulation treatment regimen for administration to a nervous system component of the mammal. The determined neuromodulation treatment regimen having at least one of a determined frequency, waveform, duration, or amplitude characteristic. In an embodiment, the treatment decision device includes a treatment decision device configured to determine that treatment is not indicated in response to the signal indicative of the sensed property of the mammal. In an embodiment, the treatment decision device includes a treatment decision device configured to determine that treatment is indicated in response to the signal indicative of the sensed property of the mammal. In an embodiment, the computer-readable medium includes a computer-readable medium configured to store information correlating at least one sensed property of the mammal and at least one neuromodulation treatment regimen. In an embodiment, the system further includes a neuromodulation device 860 configured to output a stimulus operable to modulate a nervous system component of the mammal in response to the information corresponding to the determined neuromodulation treatment regimen. In an embodiment, the neuromodulation device may include a neuromodulation source 862, a controller circuit 864, a processor circuit 866, or a communications circuit 868, and other circuits(s) 869. In an embodiment, the neuromodulation source may include an implantable neuromodulation source 862A. In an embodiment, the controller circuit may include an external controller circuit 864A.

In an embodiment, at least two of the sensor device 820, the signal generator 840, and the treatment decision device 880 may communicate using a wireless communication protocol. In an embodiment, at least two of the sensor device 820, the signal generator 840, and the treatment decision device 880 may communicate using an electrical conductor.

In an embodiment, an aspect of the neuromodulation device 860 or other neuromodulation devices described herein may be illustrated by an intracranial electrical stimulation device produced by Northstar Neuroscience and trademarked as the Renova™ cortical stimulation system. Northstar describes its Renova system as designed to deliver targeted stimulation to the cerebral cortex component of a mammal's 205 nervous system, which is illustrated as the nervous system component 207. In an embodiment, a portion of the implantable neuromodulation device 862A may be illustrated by Northstar's implantable electrode. The electrode is connected via a lead wire to a pulse generator type neuromodulation source implanted in the mammal's chest. Another portion of an implantable embodiment of the neuromodulation device 860 or the neuromodulation source 862 of FIG. 11 may be illustrated by Northstar's pulse generator type neuromodulation source. Therapeutic stimulation is controlled by a clinician that Northstar's programming system. For example, a clinician may use a computing device, such as the computing device 2290 of FIG. 29 and its user interface 2292, to control the therapeutic stimulation. Additional aspects of Northstar's Renova system are described in U.S. Pat. No. 7,146,217, Method and apparatus for effectuating a change in neural-functioning of a patient, to A. Firlik et al.

Figure 29:
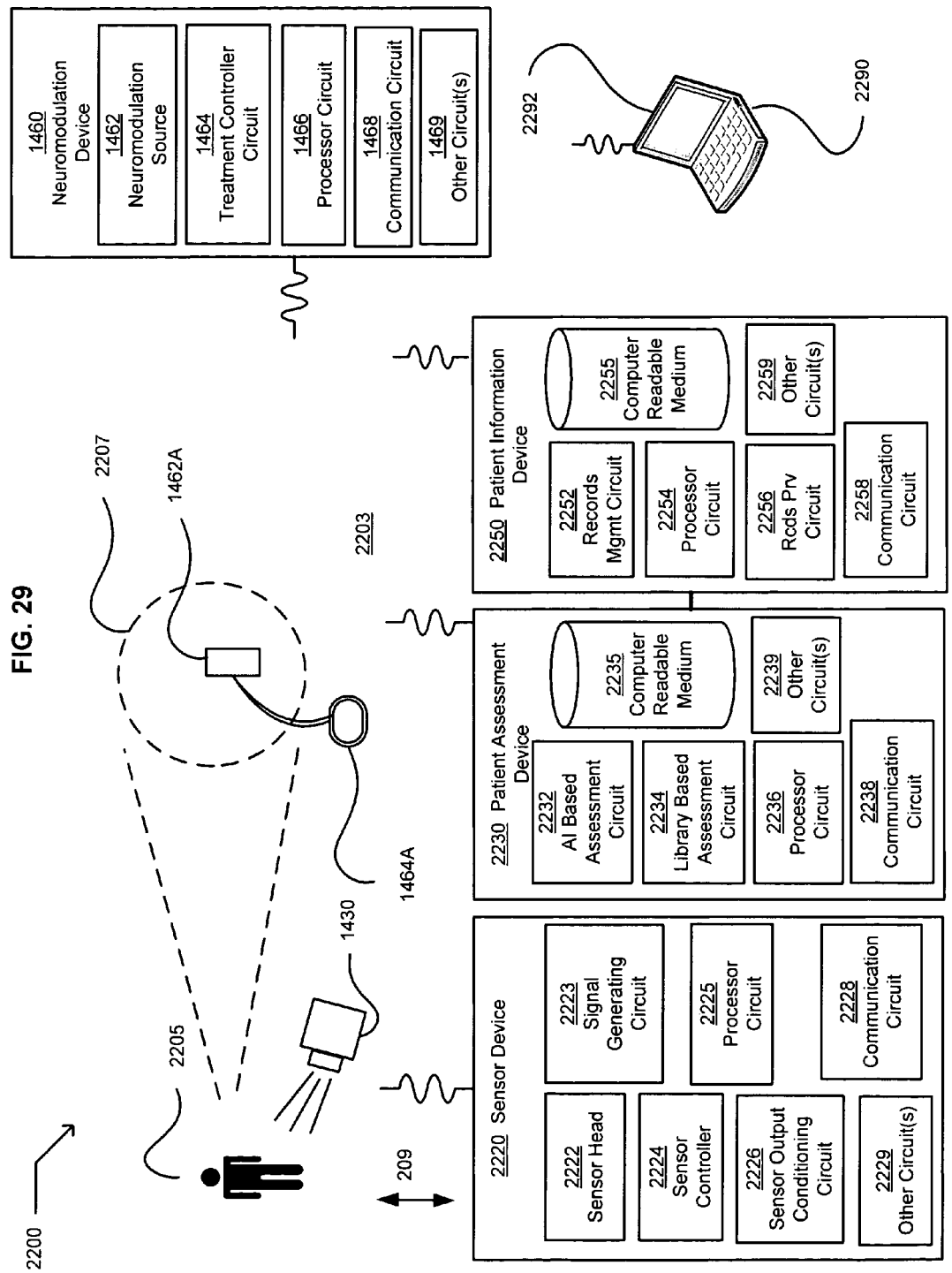
FIG. 29 illustrates an example environment that includes a system in which embodiments may be implemented.

In an embodiment, an aspect of the neuromodulation device 860 or other neuromodulation devices described herein is illustrated by a device produced by Medtronic and trademarked as the Activa® Therapy system for deep brain stimulation. Medtronic describes the Activa system as using a surgically implanted medical device, e.g. their Solentra® single or Kinetra® dual channel neurostimulator, to deliver a controlled electrical stimulation to precisely targeted areas within the brain of the mammal 205, which may be illustrated by the nervous system component 207. A portion of an implantable neuromodulation device 862A is illustrated by an Activa lead, which consists of four thin coiled-insulated wires with four electrodes at the lead tip. The lead tip is implantable in the brain. Another portion of an implantable embodiment of the neuromodulation device 860 or the neuromodulation source 862 of FIG. 11 is illustrated by an Activa neurostimulator, e.g. Solentra single or Kinetra neurostimulator. The Activa lead is connectable by wires to the Activa neurostimulator, which is implantable beneath the chest skin and below the collarbone of the mammal. The Activa neurostimulator includes a small, sealed device housing a battery and electronics, and a pulse generator that produces the electrical pulses needed for stimulation. The Activa neurostimulator delivers electrical pulses through connecting wires to the lead, and through the lead into the targeted areas in the brain. These electrical pulses can be adjusted noninvasively by a clinician or patient with an Activa programmer device, for example Medtronic's Access® controller, which uses a wireless communication link to check or change the neurostimulator's settings. In an embodiment, the computing device 2290 and its user interface 2292 of FIG. 29 are illustrated by the Activa Access controller.

In an embodiment, an aspect of the neuromodulation device 860 or other neuromodulation devices described herein is illustrated by a device produced by Boston Scientific and trademarked as the Precision Plus™ Spinal Cord Stimulation System. The Precision Plus system includes delivering electrical pulses to nerves traveling along the spinal cord of the mammal 205, which may be illustrated as the nervous system component 207. A portion of the implantable neuromodulation device 862A is illustrated by the Precision Plus electrode contacts that are implantable at locations proximate to the spinal cord. In an embodiment, certain aspects of the neuromodulation device 860 may additionally be illustrated by the Precision Plus pulse generator. Another portion of the implantable neuromodulation device 862A is illustrated by an implanted, rechargeable pulse generator, which is connected to the electrode contacts by leads. In an embodiment, certain aspects of the neuromodulation device 860 may additionally be illustrated by the Precision Plus replenishable power source and the internal and external portions of the portable power source replenishing system. In addition, an aspect of the neuromodulation device using the computing device 2290 and its user interface 2292 of FIG. 29 to control the neuromodulation device is illustrated by the Precision Plus remote control. Additional aspects of system of the Precision Plus Spinal Cord Stimulation System are described in U.S. Pat. No. 7,496,404 Rechargeable spinal cord stimulator system to Meadows et al.

In an embodiment, an aspect of the neuromodulation device 860 or other neuromodulation devices described herein is illustrated by any of several St. Jude Medical's Spinal Cord Stimulation (SCS) systems, formerly marketed under Advanced Neuromodulation. The SCS systems deliver electrical pulses to nerves traveling along the spinal cord of the mammal 205, which may be illustrated as the nervous system component 207. A portion of the implantable neuromodulation device 862A is illustrated by the SCS electrode contacts that are implantable at locations proximate to the spinal cord. An implantable embodiment of the neuromodulation device 860 is illustrated by an implantable SCS generator, which includes electronic components and sends electrical current through one or more lead to the electrode contacts. The SCS systems include an implantable pulse generator (IPG), which can include a long-life or rechargeable battery, such as those used in their Eon™ and Genesis™ Systems, or which is powered externally, such as that in their Renew® Radiofrequency System. In an embodiment, certain aspects of the neuromodulation device 1460 may additionally be illustrated by a SCS system's implantable generator. The SCS systems also include an controller that is able to wirelessly communicate with the implanted portion pulse generator and that has programming means, such as Active Balancing™, Dynamic MultiStim™, or PC-Stim®, that provide input to the IPG. In an embodiment, certain aspects of the neuromodulation device 1460 may additionally be illustrated by an SCS system controller and programming.

Figure 12:
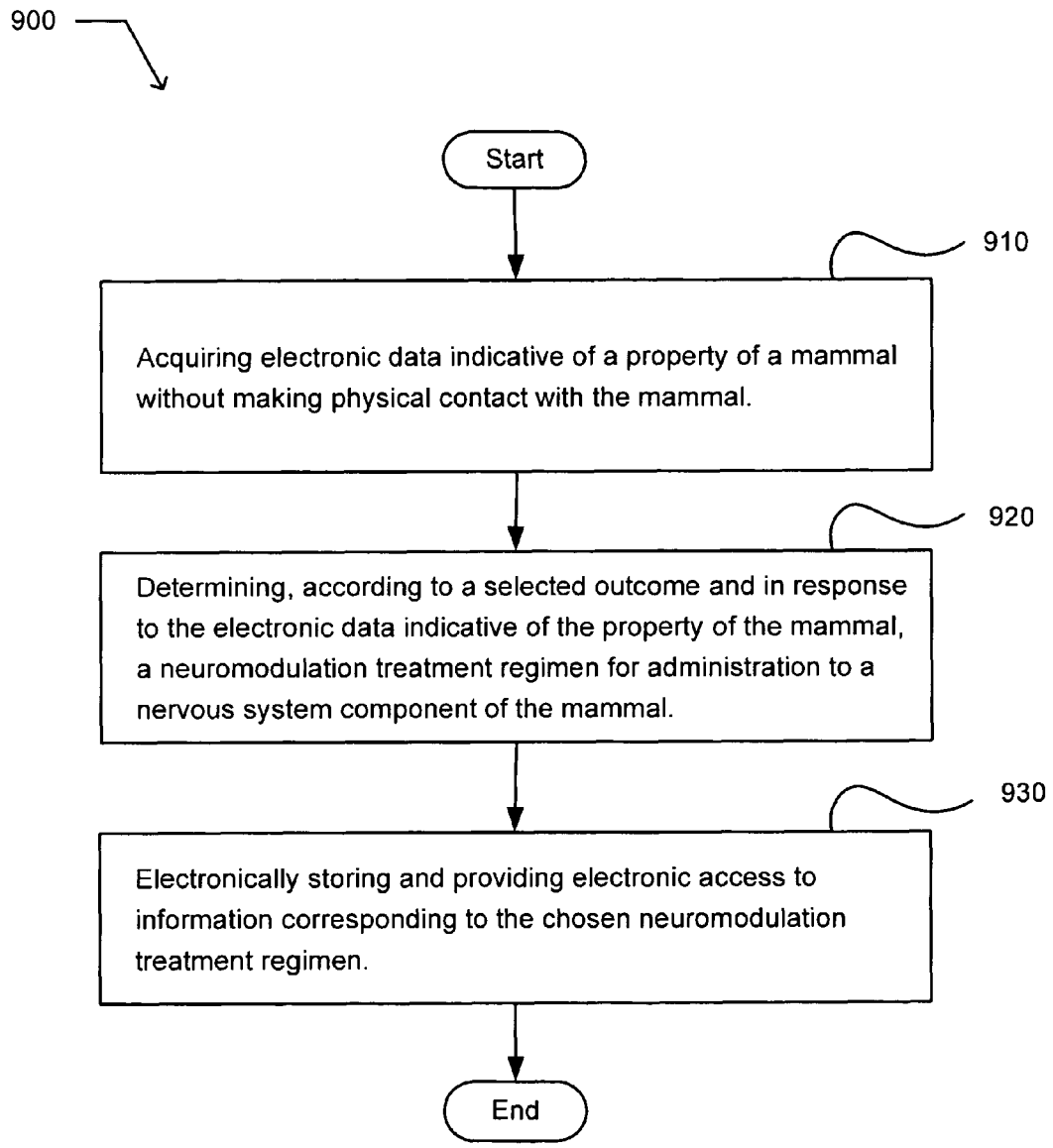
FIG. 12 illustrates an example operational flow in which embodiments may be implemented.

FIG. 12 illustrates an example operational flow 900. After a start operation, the operational flow includes a contactless sensing operation 910. The contactless sensing operation includes acquiring electronic data indicative of a property of a mammal without making physical contact with the mammal. In an embodiment, the contactless sensing operation may be implemented using the sensor device 820 described in conjunction with FIG. 11. In an embodiment, the contactless sensing operation may be implemented using the sensor device 520 described in conjunction with FIG. 8. A treatment selection operation 920 includes determining, according to a selected outcome and in response to the electronic data indicative of the property of the mammal, a neuromodulation treatment regimen for administration to a nervous system component of the mammal. In an embodiment, the treatment selection operation may be implemented using the treatment decision device 880 described in conjunction with FIG. 11. A treatment storage and retrieval operation 930 includes electronically storing and providing electronic access to information corresponding to the chosen neuromodulation treatment regimen. In an embodiment, the treatment storage and retrieval operation may be implemented using a computer-readable medium. For example, the computer-readable medium may include a computer-readable medium associated with a thin computing device, such as the thin computing device 20 described in conjunction with FIG. 1, such as the computing device 110 described in conjunction with FIG. 2, or such as the computer-readable medium 886 described in conjunction with FIG. 11. The operational flow includes an end operation.

Figure 13:
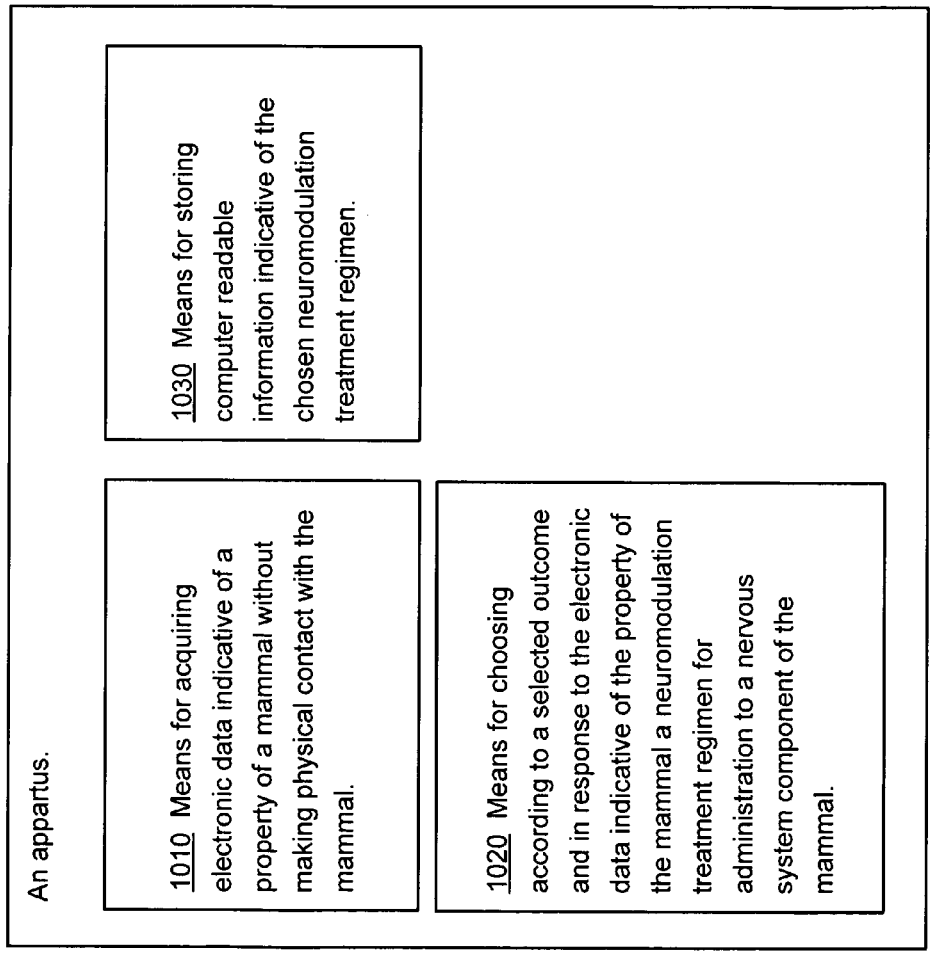
FIG. 13 illustrates an example apparatus in which embodiments may be implemented.

FIG. 13 illustrates an example apparatus 1000. The example apparatus includes means 1010 for acquiring electronic data indicative of a property of a mammal without making physical contact with the mammal. The example apparatus includes means 1020 for choosing according to a selected outcome and in response to the electronic data indicative of the property of the mammal a neuromodulation treatment regimen for administration to a nervous system component of the mammal. The example apparatus includes means 1030 for storing computer readable information indicative of the chosen neuromodulation treatment regimen.

Figure 14:
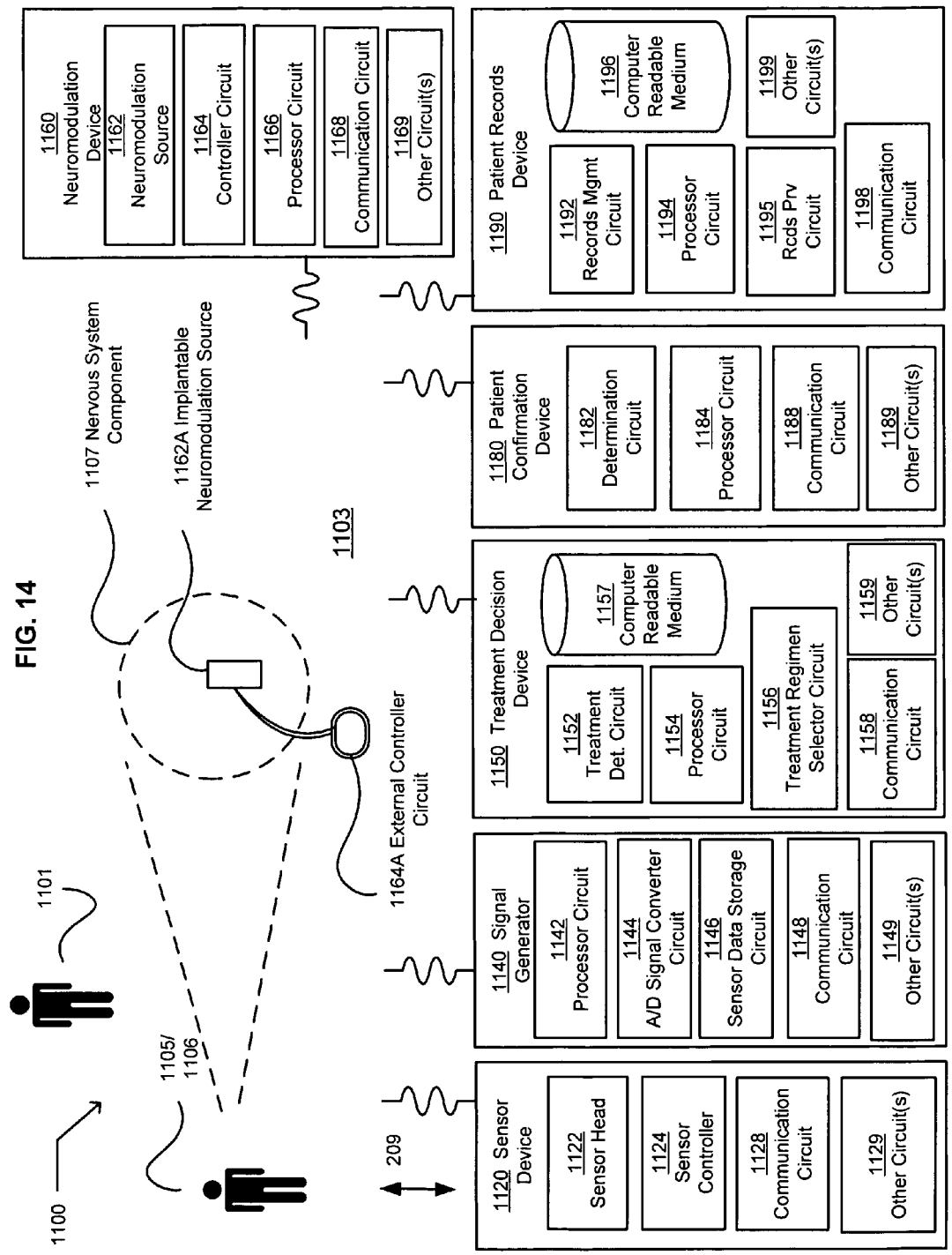
FIG. 14 illustrates an environment in which embodiments may be implemented.

FIG. 14 illustrates an environment 1100. The environment includes a system 1103. The system includes a sensor device 1120, a signal generator 1140, a patient confirmation device 1180, a treatment decision device 1150, and a patient records device 1190. The environment includes a subject mammal 1106 who is sensed by the sensor device 1120, and who may also be a patient mammal 1105. The environment also includes a third-party mammal 1101 that might be within sensing range of the sensor device. For example, the third-party mammal may include a mammal present within a sensing range of the sensor device 1120, such as a visitor, health care provider, relative, or stranger.

The sensor device 1120 is configured to sense a property of the subject mammal 1106 without physically contacting the subject mammal. In an embodiment, the sensor device may include a sensor head 1122, a sensor controller 1124, a communications circuit 1128, or other circuit(s) 1129. In an embodiment, the communications circuit 1128 may be configured for communications using an electrical conductor or a wireless system.

The signal generator 1140 is configured to generate a signal indicative of the sensed property of the subject mammal 1106. In an embodiment, the signal generator may include a processor circuit 1142, an analog to digital signal converter circuit 1144, a sensor data storage circuit 1146, a communications circuit 1148, or other circuit(s) 1149. In an embodiment, the communications circuit 1148 may be configured for communications using an electrical conductor or communications using a wireless system. In an embodiment, the signal generator may include an instance of the thin computing device 20 and the processor circuit may include the processing unit 21, as described in conjunction with FIG. 1. In an embodiment, the signal generator may include the computing device 110 and the processor circuit may include the processor 120, as described in conjunction with FIG. 2.

The treatment decision device 1150 is configured to determine in response to the signal indicative of the sensed property of the subject mammal 1106 a neuromodulation treatment regimen for administration to a nervous system component 1107 of the patient mammal 1105. In an embodiment, the treatment decision device may include a treatment determination circuit 1152, a processor circuit 1154, a treatment regimen selector circuit 1156, a computer-readable medium 1157, a communications circuit 1158, or other circuit(s) 1159. In an embodiment, the treatment decision device may include or be implemented by an instance of the thin computing device 20 and the processor circuit 1154 may include the processing unit 21, as described in conjunction with FIG. 1. In an embodiment, the treatment decision device may include or be implemented by an instance of the computing device 110 and the processor circuit may include the processor 120, as described in conjunction with FIG. 2. In an embodiment, the communications circuit 1158 may be configured for communications using an electrical conductor or communications using a wireless system.

In an embodiment, the treatment decision device 1150 is configured to determine in response to the signal indicative of the sensed property of the subject mammal 1106 a neuromodulation treatment regimen for administration to a nervous system component 1107 of the patient mammal 1105. The treatment decision device is also configured to authorize provision of the determined neuromodulation treatment regimen to the patient mammal in response to the determined identity correlation between the subject mammal and the patient mammal. In an embodiment, the treatment decision device is configured to determine in response to the signal indicative of the sensed property of the subject mammal a neuromodulation treatment regimen for administration to a nervous system component of the patient mammal and to provide electronic access to the stored information. The treatment decision device having an electronically maintained information correlating at least one possible sensed property of the subject mammal and at least one possible neuromodulation treatment regimen, a computer-implemented decision table, or a digital library correlating at least one possible sensed property of the subject mammal and at least one possible neuromodulation treatment regimen. In an embodiment, the electronically maintained information may be saved on the computer-readable medium 1196. In an embodiment, the electronically maintained information may be saved on a remote computer-readable medium (not shown) accessible by the treatment decision device.

The patient confirmation device 1180 is configured to determine an identity correlation between the subject mammal 1106 and the patient mammal 1105. For example, the third-party mammal 1101 may be within a sensing range of the sensor device 1120. In an embodiment, the patient confirmation device 1180 determines an identity correlation between the subject mammal 1106 and the patient mammal 1105, i.e., that the sensor device sensed a property of the patient mammal and not a property of the third-party mammal 1101. In an embodiment, the patient confirmation device may include a determination circuit 1182, a processor circuit 1184, a communication circuit 1188, or other circuit(s) 1189. In an embodiment, the patient confirmation device may include or may be implemented by an instance of the thin computing device 20 and the processor circuit 1184 may include the processing unit 21, as described in conjunction with FIG. 1. In an embodiment, the patient confirmation device may include or be implemented by an instance of the computing device 110 and the processor circuit may include the processor 120, as described in conjunction with FIG. 2. In an embodiment, the communications circuit 1188 may be configured for communications using an electrical conductor or communications using a wireless system. In an embodiment, the patient confirmation device includes a patient confirmation device configured to determine an identity correlation between the subject mammal and the patient mammal. The patient confirmation device in this embodiment is also configured to authorize provision of the determined neuromodulation treatment regimen to the patient mammal in response to the determined identity correlation between the subject mammal and a patient mammal.

The patient records device 1190 is configured to store information corresponding to the determined neuromodulation treatment regimen in a computer-readable medium 1196 and to provide electronic access to the stored information. In an embodiment, the patient records device may include a records management circuit 1192, a processor circuit 1194, a records privacy circuit 1195, the computer-readable medium 1196, a communications circuit 1198, and other circuit(s) 1199. In an embodiment, the patient records device may include or be implemented by an instance of the thin computing device 20 and the processor circuit 1194 may include the processing unit 21, as described in conjunction with FIG. 1. In an embodiment, the patient records device may include or be implemented by an instance of the computing device 110 and the processor circuit may include the processor 120, as described in conjunction with FIG. 2. In an embodiment, the communications circuit 1198 may be configured for communications using an electrical conductor or communications using a wireless system.

In an embodiment, the patient records device 1190 includes a patient records device configured to store information corresponding to the determined neuromodulation treatment regimen in the computer-readable medium 1196. The patient records device is also configured to store information corresponding to the identity correlation between the subject mammal and the patient mammal in the computer-readable medium. The patient records device is also configured to provide electronic access to the stored information. In an embodiment, the patient records device includes a patient records device configured to store information corresponding to the determined neuromodulation treatment regimen in the computer-readable medium. The patient records device is also configured to store information corresponding to the determined neuromodulation treatment regimen in response to the determined identity correlation between the subject mammal and a patient mammal in the computer-readable medium. The patient records device is further configured to provide electronic access to the stored information. In an embodiment, the patient records device includes a patient records device configured to store information corresponding to the determined neuromodulation treatment regimen in a computer-readable medium. The patient records device is also configured to store information corresponding to the authorized provision of the determined neuromodulation treatment regimen to the patient mammal in the computer-readable medium. The patient records device is further configured to provide electronic access to the stored information.

In an embodiment, the system 203 further includes a neuromodulation device 1160 operable to administer the determined neuromodulation treatment regimen to the nervous system component 1107 of the patient mammal 1105 if the identity correlation between the subject mammal 1106 and the patient mammal 1105 satisfies a criteria. For example, in an embodiment, the identity correlation criteria may require at least a 90% match or confidence level.

FIG. 15 illustrates an example operational flow 1200. After a start operation, the operational flow moves to a contactless sensing operation 1210. The contactless sensing operation includes sensing a property of a subject mammal without physically contacting the subject mammal. In an embodiment, the contactless sensing operation may be implemented using the sensor device 1120 described in conjunction with FIG. 14. A subject information operation 1220 includes generating a signal indicative of the sensed property of the subject mammal. In an embodiment, the subject information operation may be implemented using the signal generator 1140 described in conjunction with FIG. 14. A treatment selection operation 1230 includes determining a neuromodulation treatment regimen for administration to a nervous system component of a patient mammal in response to the signal indicative of the sensed property of the subject mammal. In an embodiment, the treatment selection operation may be implemented using the treatment decision device 1150 described in conjunction with FIG. 14. A patient verification operation 1240 includes determining an identity correlation between the subject mammal and the patient mammal. In an embodiment, the patient verification operation may be implemented using the patient confirmation device 1180 described in conjunction with FIG. 14. A patient records operation 1250 includes electronically maintaining information corresponding to the determined neuromodulation treatment regimen and to the determined identity correlation between the subject mammal and the patient mammal. In an embodiment, the patient records operation may be implemented using the patient records device 1190 described in conjunction with FIG. 14. In an embodiment, the operational flow may include at least one additional operation, such as the patient resources operation 1260. The patient resources operation includes providing electronic access to the information corresponding to the determined neuromodulation treatment regimen and to the determined identity correlation between the subject mammal and the patient mammal. The operational flow includes an end operation.

FIG. 16 illustrates an example system 1300. The example system includes means 1310 for sensing a property of a subject mammal without physically contacting the subject mammal. The system also includes means 1320 for generating a signal indicative of the sensed property of the subject mammal. The system further includes means 1330 for determining a neuromodulation treatment regimen for administration to a nervous system component of a patient mammal in response to the signal indicative of the sensed property of the subject mammal. The system also include means 1340 for determining an identity correlation between the subject mammal and the patient mammal. The system further includes means 1350 for electronically maintaining information corresponding to the determined neuromodulation treatment regimen and to the determined identity correlation between the subject mammal and the patient mammal. In an embodiment, the system may include means 1360 for providing electronic access to the information corresponding to the determined neuromodulation treatment regimen and to the determined identity correlation between the subject mammal and the patient mammal.

Figure 17:
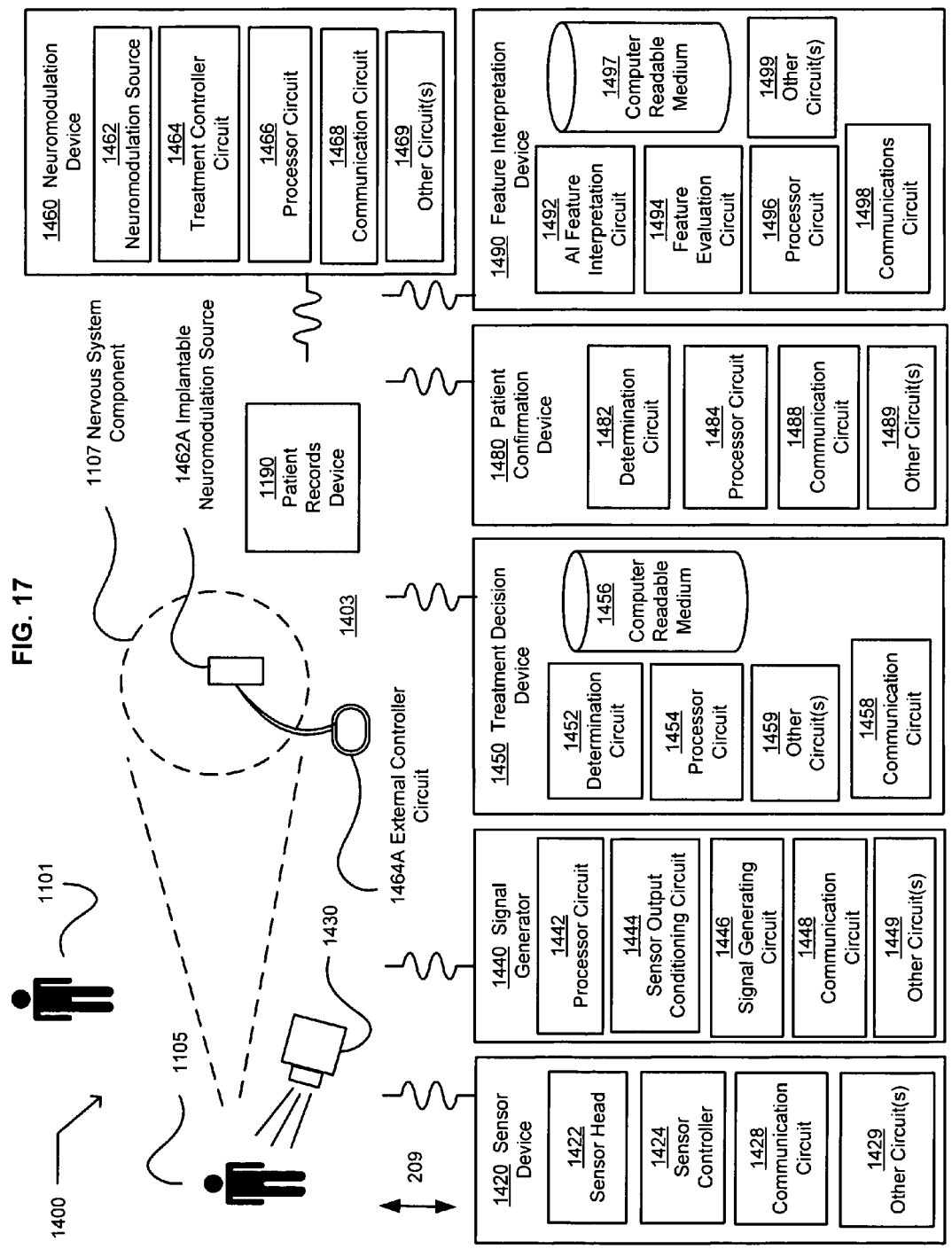
FIG. 17 illustrates an environment that includes a system in which embodiments may be implemented.

FIG. 17 illustrates an environment 1400 that includes a system 1403. The system includes a sensor device 1420, a signal generator 1440, a feature interpretation device 1490, a treatment decision device 1450, and a patient records device, illustrated as the patient records device 1190 described in conjunction with FIG. 14. The sensor device is configured to sense a property of the mammal 1105 without physically touching the mammal. The signal generator is configured to generate a signal indicative of the sensed property of the mammal. The feature interpretation device is configured to generate data indicative of a physiological characteristic of the mammal in response to the signal indicative of the property of the mammal. For example, in an embodiment, the feature interpretation device may generate data indicative of the mammal's brain wave, cardiac waveform, neural activity, pupil diameter, breathing, or temperature. In an embodiment, the feature interpretation device may include an artificial intelligence feature interpretation circuit 1492, a feature evaluation circuit 1494, a processor circuit 1496, a computer-readable medium 1497, a communications circuit 1498, or other circuit(s) 1499. In an embodiment, the feature interpretation device may include an instance of the thin computing device 20 and the processor circuit may be the processing unit 21 and the computer-readable medium may be part of the system memory, as described in conjunction with FIG. 1. In an embodiment, the feature interpretation device may include the computing device 110 and the processor circuit may be the processor 120 and the computer-readable medium may be the hard disk drive 141, as described in conjunction with FIG. 2.

The treatment decision device 1450 is configured to determine in response to the data indicative of a physiological characteristic of the mammal 1105 a neuromodulation treatment regimen for administration to a nervous system component 1107 of the mammal. In an embodiment, the treatment decision device may include an instance of the thin computing device 20 and the processor circuit may be the processing unit 21 and the computer-readable medium may be part of the system memory, as described in conjunction with FIG. 1. In an embodiment, the treatment decision device may include the computing device 110 and the processor circuit may be the processor 120 and the computer-readable medium may be the hard disk drive 141, as described in conjunction with FIG. 2. The patient records device is configured to store information corresponding to the determined neuromodulation treatment regimen in a computer-readable medium, such as the computer-readable medium 1196 of FIG. 14, and to provide electronic access to the stored information.

In an embodiment, the signal generator 1440 includes a signal generator configured to generate and to transmit via an electrically conductive pathway a signal indicative of the sensed property of the mammal 1105. In an embodiment, the signal generator may transmit via an electrically conductive pathway. For example, the electrically conductive pathway may include a bus, an interconnect, dedicated wiring, cable, Ethernet cable, telephone line, or a wired system. In an embodiment, the signal generator includes a signal generator configured to generate and wirelessly transmit a signal indicative of the sensed property of the mammal. For example, wireless transmit may include wirelessly transmitting using a local wireless system, the Internet, a global computer network, a private wireless network, a LAN, or a cellular network communications system. In an embodiment, the signal generator may be configured to transmit a signal indicative of the sensed property of the mammal in a format usable by the feature interpretation circuit 1490.

In an embodiment, the feature interpretation device 1490 includes a feature interpretation device configured to generate data indicative of a brain waveform, cardiac waveform, neural activity, pupil diameter, breathing, temperature, movement, acoustic, or body position characteristic of the mammal 1105 in response to the signal indicative of the property of the mammal. For example, a body position may include a fallen, sitting, or crumpled body position as sensed by an accelerometer, camera, or other sensor device. For example, a body position may include a position of a part of a body, such as head nodding, twitching, or repetitive limb motion. In an embodiment, the feature interpretation device includes a feature interpretation device configured to generate data indicative of a static or a varying physiological characteristic of the mammal in response to the signal indicative of the property of the mammal. In an embodiment, the feature interpretation device includes a feature interpretation device not physically coupled with the sensor device and configured to generate data indicative of a physiological characteristic of the mammal in response to the signal indicative of the property of the mammal. In an embodiment, the feature interpretation device includes a feature interpretation device physically coupled with the sensor device and configured to generate data indicative of a physiological characteristic of the mammal in response to the signal indicative of the property of the mammal.

In an embodiment, the feature interpretation device 1490 includes a feature interpretation device configured to receive a transmitted signal indicative of the property of the mammal 1105. In this embodiment, the feature interpretation device is also operable to generate data indicative of a physiological characteristic of the mammal in response to the received signal indicative of the property of the mammal. For example, the feature interpretation device may receive the transmitted signal via an electrically conductive pathway, such as a bus, or an interconnect. In an embodiment, the feature interpretation may include a feature interpretation device configured to receive a wirelessly transmitted signal indicative of the property of the mammal, and to generate data indicative of a physiological characteristic of the mammal in response to the received signal indicative of the property of the mammal. For example, the feature interpretation device may wirelessly receive the transmitted signal, such as via a local wireless system, the Internet, a global computer network, a private wireless network, a LAN, or a cellular network communications system. In an embodiment, the feature interpretation device includes a feature interpretation device configured to generate and to transmit via an electrically conductive pathway data indicative of a physiological characteristic of the mammal in response to the signal indicative of the property of the mammal. In an embodiment, the feature interpretation device includes a feature interpretation device configured to generate and to wirelessly transmit data indicative of a physiological characteristic of the mammal in response to the signal indicative of the property of the mammal.

In an embodiment, the treatment decision device 1450 includes a treatment decision device configured to decide if treatment is indicated in response to the data indicative of a physiological characteristic of the mammal 1105. In this embodiment, the treatment decision device is also configured to determine a neuromodulation treatment regimen for administration to a nervous system component 1107 of the mammal in response to the data indicative of a physiological characteristic of the mammal. In an embodiment, the treatment decision device includes a treatment decision device configured to determine in response to the data indicative of a physiological characteristic of the mammal a selected outcome-promoting neuromodulation treatment regimen for administration to a nervous system component of the mammal. In an embodiment, the treatment decision device includes a treatment decision device configured to determine a neuromodulation treatment regimen for administration to a nervous system component of the mammal at least partially based upon the signal indicative of the sensed property of the mammal and a reference database of neuromodulation treatment regimens. In an embodiment, the treatment decision device includes a treatment decision device utilizing an algorithm configured to determine a neuromodulation treatment regimen for administration to a nervous system component of the mammal at least partially based upon the signal indicative of the sensed property of the mammal and a reference database of neuromodulation treatment regimens. In an embodiment, the treatment decision device includes a treatment decision device configured to determine a neuromodulation treatment regimen for an administration to a nervous system component of the mammal according to a selected outcome and in response to the data indicative of a physiological characteristic of the mammal. For example, a selected outcome may include a selected treatment outcome, such as cure, symptom relief, a reduction or increase in neural regeneration. For example, a selected outcome may include a subjective or objective outcome perception by the mammal or health care provider, or a change at a molecular level in the mammal.

In an embodiment, the treatment decision device 1450 includes a treatment decision device configured to determine in response to the data indicative of a physiological characteristic of the mammal 1105 a neuromodulation treatment regimen for administration to a nervous system component 1107 of the mammal. The determination is responsive to an electronically stored database relating a physiological characteristic of the mammal and a neuromodulation treatment regimen, a computer-implemented decision table, a digitally maintained neuromodulation treatment regimen table, or a digital library correlating physiological characteristics of the mammal and neuromodulation treatment regimens. In an embodiment, the treatment decision device includes a treatment decision device configured to determine in response to the data indicative of a physiological characteristic of the mammal a neuromodulation treatment regimen for administration to a nervous system component of the mammal. The determined neuromodulation treatment regimen including at least one of a source, frequency, waveform, duration, or amplitude characteristic. In an embodiment, the treatment decision device includes a treatment decision device configured to determine in response to the data indicative of a physiological characteristic of the mammal a neuromodulation treatment regimen for administration to a nervous system component of the mammal. The determined neuromodulation treatment regimen having at least one of a single instance of a neural stimulus, at least two instances of neural stimuli, or a course of neural stimuli. In an embodiment, the treatment decision device includes a treatment decision device not physically coupled with the feature interpretation device and configured to determine in response to the data indicative of a physiological characteristic of the mammal a neuromodulation treatment regimen for administration to a nervous system component of the mammal.

In an embodiment, the treatment decision device 1450 includes a treatment decision device configured to determine in response to the data indicative of a physiological characteristic of the mammal 1105 a neuromodulation treatment regimen for administration to a nervous system component 1107 of the mammal. In this embodiment, treatment decision device is also configured to facilitate an administration of the neuromodulation treatment regimen to the nervous system component of the mammal. In an embodiment, the treatment decision device includes a treatment decision device configured to determine in response to the data indicative of a physiological characteristic of the mammal a neuromodulation treatment regimen for administration to a nervous system component of the mammal. In this embodiment, the treatment decision device is also configured to control an administration of the selected neuromodulation treatment regimen to the nervous system component of the mammal by a neuromodulation device 1460. The treatment decision device includes a treatment decision device configured to determine a neuromodulation treatment regimen for administration to a nervous system component of the mammal in response to the data indicative of a physiological characteristic of the mammal and in response to a previous administration of at least one neuromodulation treatment regimen to the mammal. For example, a response to a previous administration of at least one neuromodulation treatment regimen to the mammal, the treatment decision device may include a rule such as do not treat more than once in 60 minutes, or make this next treatment different than previous. In an embodiment, the treatment decision device includes a treatment decision device configured to determine in response to the data indicative of a physiological characteristic of the mammal a first neuromodulation treatment regimen and a second neuromodulation treatment regimen for a possible administration to a nervous system component of the mammal.

In an embodiment, the treatment decision device 1450 includes a treatment decision device configured to determine a neuromodulation treatment regimen for administration to a nervous system component 1107 of the mammal 1105 in response to the data indicative of a physiological characteristic of the mammal and in response and responsive to data from another source. For example, the data from another source may include a time (such as a precise time, or a portion of a day, such as morning, afternoon, evening, or night), ambient temperature, mammal body temperature, or a location (such as in bed, concert hall, or in a vehicle). In an embodiment, the treatment decision device includes a treatment decision device configured to receive a transmitted signal indicative of the data indicative of a physiological characteristic of the mammal. In this embodiment, the treatment decision device is also configured to determine in response to the data indicative of a physiological characteristic of the mammal a neuromodulation treatment regimen for administration to a nervous system component of the mammal. In an embodiment, the treatment decision device includes a treatment decision device configured to receive a wirelessly transmitted signal indicative of the data indicative of a physiological characteristic of the mammal. In this embodiment, the treatment decision device is also configured to determine in response to the data indicative of a physiological characteristic of the mammal a neuromodulation treatment regimen for administration to a nervous system component of the mammal. In an embodiment, the treatment decision device includes a treatment decision device configured to determine in response to the data indicative of a physiological characteristic of the mammal a neuromodulation treatment regimen for administration to a nervous system component of the mammal. In this embodiment, the treatment decision device is also configured to transmit information indicative of the selected neuromodulation treatment regimen via an electrically conductive pathway. In an embodiment, the treatment decision device includes a treatment decision device configured to determine in response to the data indicative of a physiological characteristic of the mammal a neuromodulation treatment regimen for administration to a nervous system component of the mammal. In this embodiment, the treatment decision device is also configured to wirelessly transmit information indicative of the selected neuromodulation treatment regimen.

In an embodiment, the system 1403 further includes the neuromodulation device 1460. The neuromodulation device is configured to administer the selected neuromodulation treatment regimen to the nervous system component 1107 of the mammal 1105. In an embodiment, the neuromodulation device may include a neuromodulation source 1462, a treatment controller circuit 1464, a processor circuit 1466, a communications circuit 1468, or other circuit(s) 1469. In an embodiment, the neuromodulation source may include an implantable neuromodulation source 1462A. In an embodiment, the treatment controller circuit may include an external controller circuit 1464A. In an embodiment, the neuromodulation device may include a neuromodulation device physically associable with the mammal and configured to administer the selected neuromodulation treatment regimen to the nervous system component of the mammal. For example, the neuromodulation device may include at least an implantable portion, a surface contact portion, or both an implantable portion and a surface contact portion. In an embodiment, the neuromodulation device includes a neuromodulation device operable to generate and administer the selected neuromodulation treatment regimen to a nervous system component of the mammal. In an embodiment, the neuromodulation device includes a neuromodulation device operable to administer the selected neuromodulation treatment regimen to a nervous system component of the mammal while the mammal is within a space. In an embodiment, the neuromodulation device includes a neuromodulation device operable to automatically administer the selected neuromodulation treatment regimen to a nervous system component of the mammal in response to at least one of a command received from the treatment decision device, in response to an input initiated by the mammal, or in response to an input initiated by a health care provider.

In an embodiment, the neuromodulation device 1460 includes a neuromodulation device configured to administer the selected neuromodulation treatment regimen to a component 1107 of the vagal nervous system of the mammal 1105. In an embodiment, the neuromodulation device includes a neuromodulation device configured to administer the selected neuromodulation treatment regimen to a central nervous system component of the mammal. In an embodiment, the neuromodulation device includes a neuromodulation device configured to administer the selected neuromodulation treatment regimen to a component of the brain of the mammal. In an embodiment, the neuromodulation device includes a neuromodulation device configured to administer the selected neuromodulation treatment regimen to a component of the spinal cord of the mammal. In an embodiment, the neuromodulation device includes a neuromodulation device configured to administer the selected neuromodulation treatment regimen to a component of the peripheral nervous system of the mammal. In an embodiment, the neuromodulation device includes a neuromodulation device configured to administer the selected neuromodulation treatment regimen to a component of the somatic nervous system of the mammal. In an embodiment, the neuromodulation device includes a neuromodulation device configured to administer the selected neuromodulation treatment regimen to a sensory nerve, a motor nerve, the autonomic nervous system component, or the enteric nervous system component of the mammal. In an embodiment, the neuromodulation device includes a neuromodulation device configured to administer the selected neuromodulation treatment regimen to a neurotransmitter-releasing component of the nervous system of the mammal. In an embodiment, the neuromodulation device includes a neuromodulation device configured to receive a transmitted signal indicative of the selected neuromodulation treatment regimen via an electrically conductive pathway. In this embodiment, the neuromodulation device is also configured to administer the selected neuromodulation treatment regimen to the nervous system component of the mammal. In an embodiment, the neuromodulation device includes a neuromodulation device configured to receive a wirelessly transmitted signal indicative of the selected neuromodulation treatment regimen. In this embodiment, the neuromodulation device is also configured to administer the selected neuromodulation treatment regimen to the nervous system component of the mammal.

In an embodiment, the system includes an illumination source 1430 operable to illuminate at least a portion of the mammal 1105 with an energy to which the sensor device 1420 is responsive. For example, the energy may include a visible light energy, a radio frequency energy, a microwave frequency energy, or an ultrasonic frequency energy. In an embodiment, the illumination source includes an illumination source operable to illuminate at least a portion of the mammal with an energy to which the sensor device is responsive, and configured for a physical association with an object. An example is described in U.S. Pat. No. 7,272,431, Apparatus and methods for performing remote detection of physiological activity, to W. McGrath. U.S. Pat. No. 7,272,431 describes an aspect involving obtaining information concerning respiration and heart function by using a source containing an oscillator configured to illuminate a subject with electromagnetic signal beam and a receiver configured to observe changes in the amplitude of the electromagnetic signal reflected by the subject.

In an embodiment, the system 1403 includes a patient confirmation device 1480 operable to determine that the sensor signal indicative of a property of the mammal 1105 was originated in response to the mammal. In an embodiment, the patient confirmation device is operable to determine that the sensor signal indicative of a property of the mammal was originated in response to the mammal 1105 and not another mammal, such as for example, the third-party mammal 1101. For example, in an embodiment, the determination that the sensor signal indicative of a property of the mammal 1105 was originated in response to the mammal may be facilitated by an RFIG chip associated with the mammal, a facial recognition of the mammal, or a tendered fingerprint.

FIG. 18 illustrates an example operational flow 1500. After a start operation, the operational flow includes a contactless sensing operation 1510. The contactless sensing operation includes sensing a property of a mammal without physically touching the mammal. In an embodiment, the contactless sensing operation may be implemented using the sensor device 1420 described in conjunction with FIG. 17. A subject information operation 1520 includes generating a signal indicative of the sensed property of the mammal. In an embodiment, the subject information operation may be implemented using the signal generator 1440 described in conjunction with FIG. 17. An evaluation operation 1530 includes generating data indicative of a physiological characteristic of the mammal in response to the signal indicative of the property of the mammal. In an embodiment, the evaluation operation may be implemented using the feature interpretation device 1490 described in conjunction with FIG. 17. A patient treatment plan operation 1540 includes determining in response to the data indicative of a physiological characteristic of the mammal a neuromodulation treatment regimen for administration to a nervous system component of the mammal. In an embodiment, the patient treatment plan operation may be implemented using the treatment decision device 1450 described in conjunction with FIG. 17. A patient records operation 1550 includes storing information corresponding to the determined neuromodulation treatment regimen in a computer-readable medium. In an embodiment, the patient records operation may be implemented using the patient records device 1190 described in conjunction with FIG. 14. A patient resources operation 1560 includes providing electronic access to the stored information. In an embodiment, the patient resources operation may be implemented using the patient records device 1190, which may include use of the communications circuit 1198. The operational flow includes an end operation.

FIG. 19 illustrates an example system 1600. The system includes means 1610 for sensing a property of a mammal without physically touching the mammal. The system also includes means 1620 for generating a signal indicative of the sensed property of the mammal. The system further includes means 1630 for generating data indicative of a physiological characteristic of the mammal in response to the signal indicative of the property of the mammal. The system includes means 1640 for selecting in response to the data indicative of a physiological characteristic of the mammal a neuromodulation treatment regimen for administration to a nervous system component of the mammal. The system also includes means 1650 for storing information corresponding to the determined neuromodulation treatment regimen in a computer-readable medium. The system further includes means 1660 for providing electronic access to the stored information.

Figure 20:
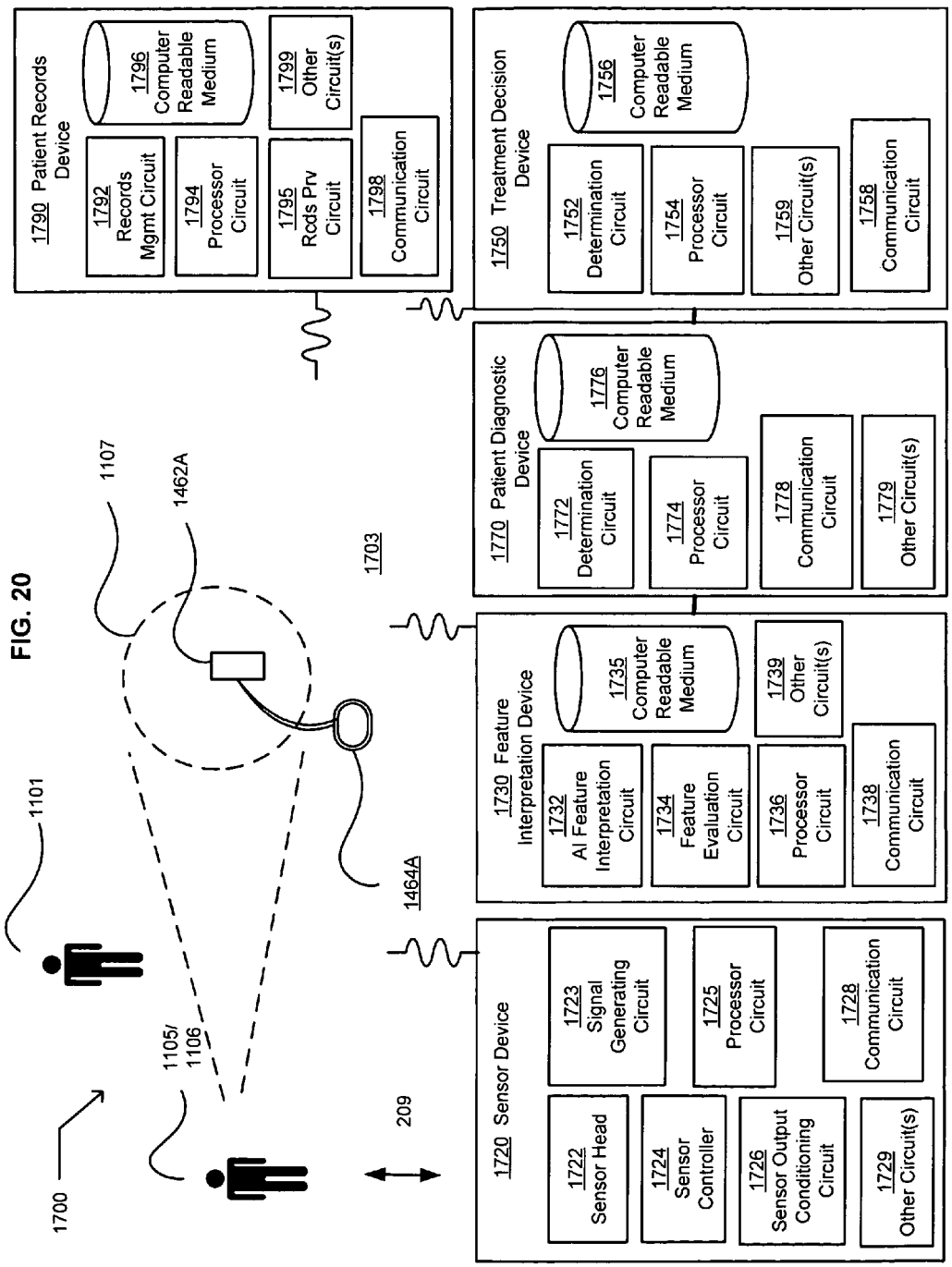
FIG. 20 illustrates an example environment that includes a system in which embodiments may be implemented.

FIG. 20 illustrates an example environment 1700 that includes a system 1703. The system includes a sensor device 1720 operable to generate a sensor signal indicative of the property of the mammal 1105. In an embodiment, the sensor device may include a sensor head 1722, a signal generating circuit 1723, a sensor controller 1724, a processor circuit 1725, a sensor output conditioning circuit 1726, a communications circuit 1728, or other circuit(s) 1729. The system also includes a feature interpretation device 1730 operable to generate data indicative of a physiological characteristic of the mammal in response to the sensor signal indicative of the property of the mammal. In an embodiment, the feature interpretation circuit may include an artificial intelligence based feature interpretation circuit 1732, a feature evaluation circuit 1734, a computer-readable medium 1735, a processor circuit 1736, a communication circuit 1738, or other circuits(s) 1739. The system includes a patient diagnostic device 1770 operable to identify a disease, disorder, or medically treatable condition in response to the data indicative of a physiological characteristic of the mammal. In an embodiment, the patient diagnostic device may include a determination circuit 1772, a processor circuit 1774, a computer-readable medium 1776, a communication circuit 1778, or other circuit(s) 1779. The system also includes a treatment decision device 1750 operable to determine a neuromodulation treatment regimen responsive to the identified disease, disorder, or medically treatable condition. An example is described in U.S. Pat. No. 5,335,657, Therapeutic treatment of sleep disorder by nerve stimulation, to R. Terry, Jr. et al. In an embodiment, the decision device 1750 is operable to determine a neuromodulation treatment regimen responsive to the identified disease, disorder, or medically treatable condition according to a selected outcome. The system includes a patient records device 1790 configured to store information corresponding to the determined neuromodulation treatment regimen in a computer-readable medium and to provide electronic access to the stored information.

In an embodiment, the system 1703 includes a neuromodulation device operable to administer the chosen neuromodulation treatment regimen to a nervous system component 1107 of the mammal 1105. For example, the neuromodulation device may be substantially similar to the neuromodulation device 1460 described in conjunction with FIG. 17.

Another example system 1703 may be illustrated at least in part by the environment 1403 of FIG. 17 and the environment 1700 of FIG. 20. The another system includes the sensor device 1720, which is responsive to a property of the subject mammal 1106 and operable to generate a sensor signal indicative of the property of the subject mammal. The another system includes the feature interpretation device 1730, which is operable to generate data indicative of a physiological characteristic of the subject mammal in response to the sensor signal indicative of the property of the subject mammal. The another system includes the treatment decision device 1750 operable to determine a neuromodulation treatment regimen responsive to the data indicative of a physiological characteristic of the subject mammal according to a selected outcome for a patient mammal.

The another system 1703 also includes a patient confirmation device 1480 an embodiment of which is illustrated as the patient confirmation device described in conjunction with FIG. 17, which is operable to recognize a likeness between the subject mammal 1106 and the patient mammal 1105. For example, in an embodiment, the patient confirmation device is operable to recognize a likeness between the subject mammal and the patient mammal, or is operable to recognize a non-likeness between the third-party mammal 1101 and the patient mammal. This is expected to minimize any likelihood that a neuromodulation treatment regimen would be delivered to the patient mammal in response to sensor data acquired from the third-party mammal. In an embodiment, the patient confirmation device includes a patient confirmation device operable to recognize a likeness between the subject mammal and the patient mammal. In this embodiment, the patient confirmation device is also operable to facilitate an administration of the selected neuromodulation treatment regimen to a nervous system component of the patient mammal if there is a recognized likeness between the subject mammal and the patient mammal. The another system includes the patient records device 1790, which is configured to store information corresponding to the determined neuromodulation treatment regimen and information corresponding to the recognized likeness between the subject mammal and the patient mammal in a computer-readable medium. The patient records device is also configured to provide electronic access to the stored information. In an embodiment, the another system may include the neuromodulation device 1460, which is operable to administer the selected neuromodulation treatment regimen to the nervous system component of the patient mammal. In an embodiment, the neuromodulation device is operable to administer the selected neuromodulation treatment regimen to the nervous system component of the patient mammal if there is a recognized likeness between the subject mammal and the patient mammal.

Figure 21:
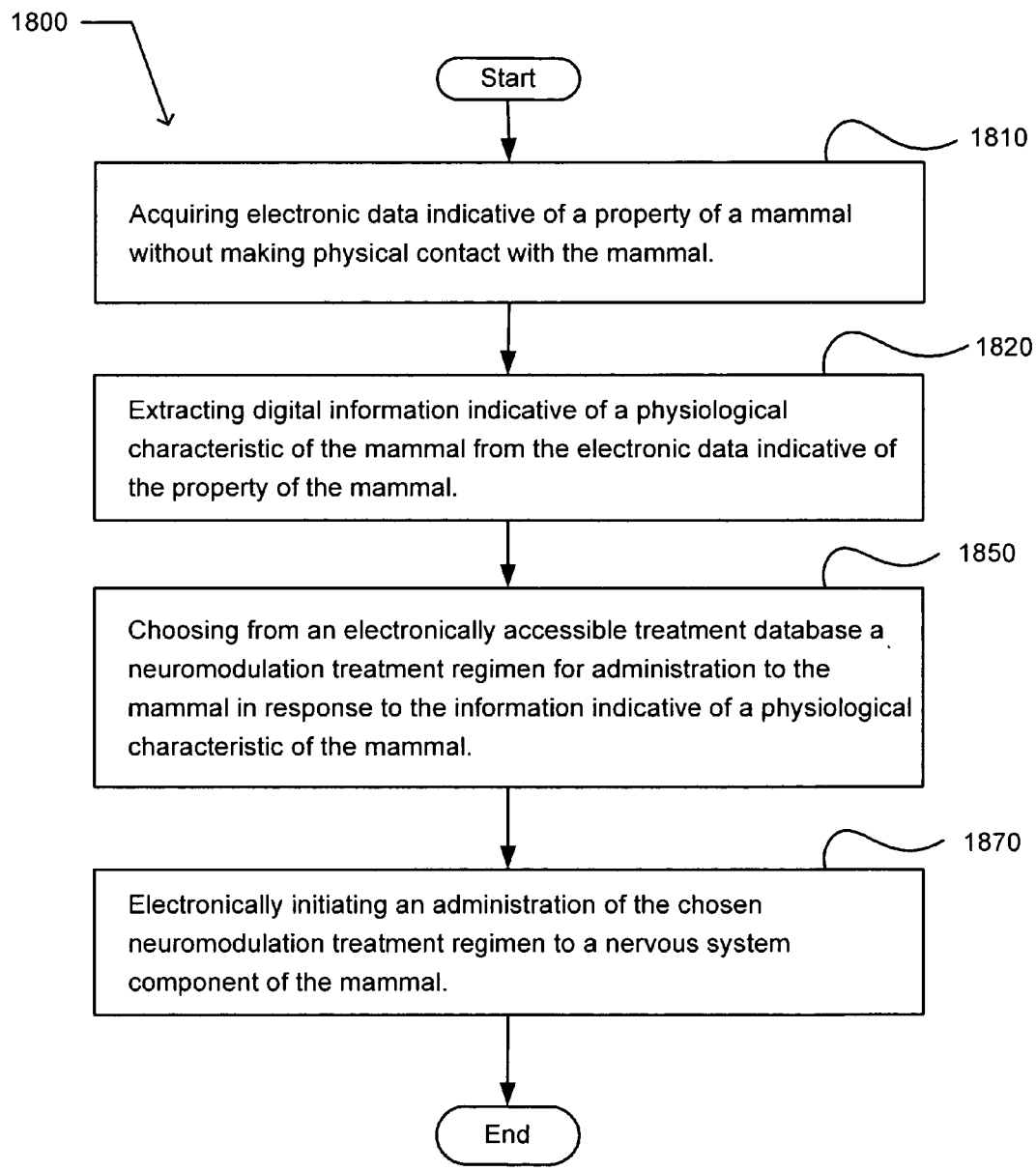
FIG. 21 illustrates an example operational flow in which embodiments may be implemented.

FIG. 21 illustrates an example operational flow 1800. After a start operation, the operational flow includes a contactless sensing operation 1810. The contactless sensing operation includes acquiring electronic data indicative of a property of a mammal without making physical contact with the mammal. In an embodiment, the contactless sensing operation may be implemented using the sensor device 1720 described in conjunction with FIG. 20. A data reduction operation 1820 includes extracting digital information indicative of a physiological characteristic of the mammal from the electronic data indicative of the property of the mammal. In an embodiment, the data reduction operation may be implemented using the feature interpretation device 1730. A treatment plan selection operation 1850 includes choosing from an electronically accessible treatment database a neuromodulation treatment regimen for administration to the mammal in response to the information indicative of a physiological characteristic of the mammal. The treatment plan selection operation may be implemented using the treatment decision device 1750. A treatment operation 1870 includes electronically initiating an administration of the chosen neuromodulation treatment regimen to a nervous system component of the mammal. In an embodiment, the treatment operation may be implemented using the neuromodulation device 1460 described in conjunction with FIG. 17. The operational flow includes an end operation.

FIG. 22 illustrates an alternative embodiment of the example operational flow 1800 described in FIG. 21. The contactless sensing operation 1810 may include at least one additional operation, such as an operation 1812. The operation 1812 includes acquiring electronic data indicative of a property of a mammal present in a space without making physical contact with the mammal. In an embodiment, the data reduction operation 1820 includes in an operation 1822 performed at a location remote from the space. The data reduction operation includes extracting digital information indicative of a physiological characteristic of the mammal from the electronic data indicative of the state of the mammal. For example, in an embodiment, the space may include a bedroom of a house occupiable by the mammal. A location remote from the space may include another room of the house, or may include a networked computing device located, hosted, or maintained at a remote location, such as a physician's office, an original equipment manufacturer of a sensor device, such as the sensor device 1720, or an office location of a third-party.

In an embodiment involving the operation 1812, an operation 1852 includes, in an operation performed at a location remote from the space, choosing from an electronically readable treatment database a neuromodulation treatment regimen for administration to the mammal in response to the information indicative of a physiological characteristic of the mammal. In an embodiment involving the operation 1812 and the operation 1822, an operation 1854 includes, in another operation performed at another location remote from the space, choosing from an electronically readable treatment database a neuromodulation treatment regimen for administration to the mammal in response to the information indicative of a physiological characteristic of the mammal.

FIG. 23 illustrates another alternative embodiment of the example operational flow 1800 described in FIG. 21. The data reduction operation 1820 may include at least one additional embodiment. The at least one additional embodiment may include an operation 1826, an operation 1828, an operation 1832, an operation 1834, an operation 1836, or an operation 1838. The operation 1826 includes distilling digital information indicative of a physiological characteristic of the mammal from the electronic data indicative of the property of the mammal. The operation 1828 includes inferring digital information indicative of a physiological characteristic of the mammal from the electronic data indicative of the property of the mammal. The operation 1832 includes deriving digital information indicative of a physiological characteristic of the mammal from the electronic data indicative of the property of the mammal. The operation 1834 includes extracting using an artificial intelligence tool digital information indicative of a physiological characteristic of the mammal from the electronic data indicative of the property of the mammal. In an embodiment, an artificial intelligence tool or a tool that uses artificial intelligence includes at least one an architecture, language, methodology, program, or algorithm that implement an artificial intelligence concept. The operation 1836 includes employing an artificial intelligence technique to extract digital information indicative of a physiological characteristic of the mammal from the electronic data indicative of the property of the mammal. The operation 1838 includes, in an operation performed in a space, extracting digital information indicative of a physiological characteristic of the mammal from the electronic data indicative of the property of the mammal. In this embodiment involving the operation 1838, the patient treatment plan operation 1850 described in conjunction with FIG. 21 includes an operation 1856. The operation 1856 includes, in another operation performed at a location remote from the space, choosing from an electronically readable treatment database a neuromodulation treatment regimen for administration to the mammal in response to the information indicative of a physiological characteristic of the mammal.

FIG. 24 illustrates a further alternative embodiment of the example operational flow 1800 described in FIG. 21. In an embodiment, the patient treatment plan operation 1850 may include at least one additional embodiment. The at least one additional embodiment may include an operation 1857, 1858, 1862, or 1864. The operation 1857 includes choosing from an electronically readable treatment database a neuromodulation treatment regimen for administration to the mammal in response to a selected outcome and to the information indicative of a physiological characteristic of the mammal. The operation 1858 includes choosing from a digitally maintained treatment decision table a neuromodulation treatment regimen for administration to the mammal in response to the information indicative of a physiological characteristic of the mammal. The operation 1862 includes choosing from a digital library correlating physiological characteristics and neural stimuli a neuromodulation treatment regimen for administration to the mammal in response to the information indicative of a physiological characteristic of the mammal. The operation 1864 includes deciding if treatment is indicated in response to the information indicative of a physiological characteristic of the mammal. If treatment is indicated, the operation 1864 includes choosing from an electronically readable treatment database a neuromodulation treatment regimen for administration to the mammal in response to the information indicative of a physiological characteristic of the mammal.

FIG. 25 illustrates another alternative embodiment of the example operational flow 1800 described in FIG. 21. In an embodiment, the treatment operation 1870 may include at least one additional embodiment. The at least on additional embodiment may include an operation 1874, an operation 1876, an operation 1878, an operation 1882, an operation 1884, or an operation 1886. The operation 1874 includes facilitating a transformation of a physiological characteristic of the mammal to a selected state by electronically initiating an administration of the chosen neuromodulation treatment regimen to a nervous system component of the mammal. In an embodiment, a physiological characteristic may include any physiological characteristic, including any normal or abnormal physical characteristic, such as, for example but not limited to, a normal sinus rhythm or an abnormal sinus rhythm, tachycardia, wakefulness, hypotension, epileptic seizure, drowsiness, sleep, consciousness, unconsciousness, breathing or resting, excited, or seizing, for example in a neuronal or muscular cell or tissue. In an embodiment, a physiological characteristic may be indicative of a disease state or of a disorder. In an embodiment, a physiological characteristic may include a neurological activity, brain wave, blood pressure, or heart rate. The operation 1876 includes substantially transforming a physiological characteristic of the mammal to a selected state by electronically initiating an administration of the chosen neuromodulation treatment regimen to a nervous system component of the mammal. The operation 1878 includes an electronically initiating an administration of a selected outcome-promoting dose of the chosen neuromodulation treatment regimen to a nervous system component of the mammal. In an embodiment, a dose may include a series of doses, which may individually be similar or dissimilar. In an embodiment, a dose is a simple on/off with a refraction time. In an embodiment, a dose may include a series of individual doses over a time. The operation 1882 includes electronically initiating an administration of the chosen neuromodulation treatment regimen to a nervous system component of the mammal and provoking a selected outcome. In an embodiment, provoking includes eliciting or causing a selected outcome. The operation 1884 includes electronically initiating an administration of the chosen neuromodulation treatment regimen to a nervous system component of the mammal and provoking a state of the mammal. For example, a state may include a sleep state, REM state, or a heart rate. The operation 1886 includes administering the chosen neuromodulation treatment regimen to a nervous system component of the mammal and achieving a selected change of a state of the mammal. For example, achieving a selected change of a state of the mammal may include achieving a selected change of a seizure state, or achieving a selected change of a firing state of a nerve causing pain.

FIG. 26 illustrates a further alternative embodiment of the example operational flow 1800 described in FIG. 21. The operational flow may include at least one additional operation. The at least one additional operation may include an operation 1902, an operation 1904, an operation 1906, an operation 1908, an operation 1912, an operation 1914, an operation 1916, an operation 1918, or an operation 1922. The operation 1902 includes physically associating with an object a sensor device operable to generate electronic data indicative of a property of the mammal without making contact with the mammal. The operation 1904 includes illuminating at least a portion of the mammal with an energy. The operation 1906 includes physically associating with an object a sensor device operable to generate electronic data indicative of a property of the mammal without making contact with the mammal. The operation 1906 also includes illuminating at least a portion of the mammal with an energy to which the sensor device is responsive. The operation 1908 includes communicating the electronic data indicative of a property of the mammal via an electrically conductive pathway to a device operable to extract the information indicative of a physiological characteristic of the mammal from the electronic data indicative of a property of the mammal. The operation 1912 includes wirelessly communicating the electronic data indicative of a property of the mammal to a device that extracts the information indicative of a physiological characteristic of the mammal from the electronic data indicative of a property of the mammal. The operation 1914 includes communicating the extracted information indicative of a physiological characteristic of the mammal via an electrically conductive pathway to another device that determines the neuromodulation treatment regimen for administration to the mammal in response to the information indicative of a physiological characteristic of the mammal. The operation 1916 includes wirelessly communicating the extracted information indicative of a physiological characteristic of the mammal to another device that determines the neuromodulation treatment regimen for administration to the mammal in response to the information indicative of a physiological characteristic of the mammal. The operation 1918 includes communicating the chosen neuromodulation treatment regimen via an electrically conductive pathway to a further device that electronically administers the chosen neuromodulation to a nervous system component of the mammal. The operation 1922 includes wirelessly communicating the chosen neuromodulation treatment regimen to a further device that electronically administers the chosen neuromodulation to a nervous system component of the mammal.

FIG. 27 illustrates an example operational flow 2000. After a start operation, the operational flow includes a contactless sensing operation 2010. The contactless sensing operation includes acquiring electronic data indicative of a property of a subject mammal without making physical contact with the subject mammal. In an embodiment, the contactless sensing operation may be implemented using the sensor device 1720 described in conjunction with FIG. 20. A data reduction operation 2020 includes extracting digital information indicative of a physiological characteristic of the subject mammal from the electronic data indicative of the property of the mammal. In an embodiment, the data reduction operation may be implemented using the feature interpretation device 1730. A treatment plan selection operation 2030 includes choosing from an electronically readable treatment database a neuromodulation treatment regimen for administration to a patient mammal in response to the information indicative of a physiological characteristic of the subject mammal. In an embodiment, the treatment plan selection operation may be implemented using the treatment decision device 1750. A confirmation operation 2040 includes recognizing a substantial likeness between the subject mammal and a patient mammal. In an embodiment, the confirmation operation may be implemented using the patient confirmation device 1480 described in conjunction with FIG. 17. A treatment operation 2050 includes automatically initiating an administration of the chosen neuromodulation to a nervous system component of the patient mammal. In an embodiment, "automatically" includes taking or initiating an action without a human intervention, without a human decision, or independent of an external human control. In an embodiment, the treatment operation may be implemented using the neuromodulation device 1460. In an embodiment, the treatment operation includes a treatment operation 2052 electronically administering the chosen neuromodulation to a nervous system component of the patient mammal only if the confirmation operation recognizes a substantial likeness between the subject mammal and a patient mammal. The operational flow 2000 includes an end operation.

Figure 28:
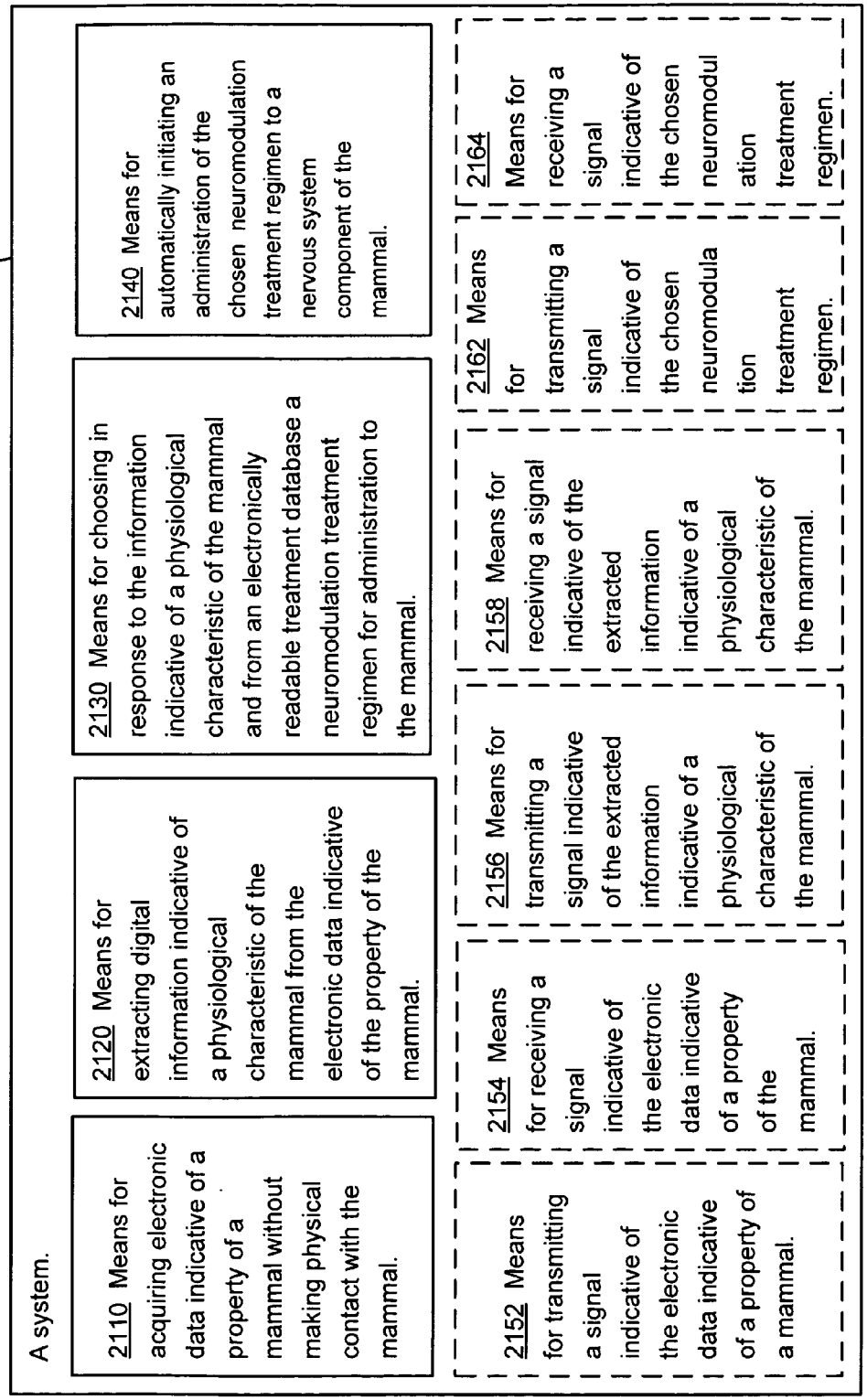
FIG. 28 illustrates an example system in which embodiments may be implemented.

FIG. 28 illustrates an example system 2100. The system includes means 2110 for acquiring electronic data indicative of a property of a mammal without making physical contact with the mammal. The system also includes means 2120 for extracting information indicative of a physiological characteristic of the mammal from the electronic data indicative of the property of the mammal. The system further includes means 2130 for choosing in response to the information indicative of a physiological characteristic of the mammal and from an electronically readable treatment database a neuromodulation treatment regimen for administration to the mammal. The system also includes means 2140 for automatically initiating an administration of the chosen neuromodulation to a nervous system component of the patient mammal.

In an embodiment, the system includes means 2152 for transmitting a signal indicative of the electronic data indicative of a property of the mammal. In an embodiment, the system includes means 2154 for receiving a signal indicative of the electronic data indicative of a property of the mammal. In an embodiment, the system includes means 2156 for transmitting a signal indicative of the extracted information indicative of a physiological characteristic of the mammal. In an embodiment, the system includes means 2158 for receiving a signal indicative of the extracted information indicative of a physiological characteristic of the mammal. In an embodiment, the system includes means 2162 for transmitting a signal indicative of the chosen neuromodulation treatment regimen. In an embodiment, the system includes means 2164 for receiving a signal indicative of the chosen neuromodulation treatment regimen.

FIG. 29 illustrates an example environment 2200 that includes a system 2203. The system includes a sensor device 2220 operable to detect a property of a mammal 2205 without a direct physical contact with the mammal. The system also includes a patient assessment device 2230 operable to evaluate the detected property of the mammal for an indicator of a disease, disorder, or symptom potentially treatable by a neuromodulation treatment regimen (hereafter referred to as "disease"). For example, if the detected property is a brain wave, an evaluation of the detected property may indicate that the brain wave includes a characteristic of an epileptic seizure event. For example, if the detected property is a cardiac waveform, an evaluation of the detected property may indicate that the cardiac waveform includes a characteristic of a heart arrhythmia. In an embodiment, the patient assessment device may include a computing device having a database, a lookup table, or an artificial intelligence tool operable to facilitate the evaluation of the detected property of the mammal for an indicator of a disease, disorder, or symptom potentially treatable by a neuromodulation treatment regimen. For example, the computing device may include the thin computing device 20 described in conjunction with FIG. 1 or the computing device 110 described in conjunction with FIG. 2. The system includes a patient information device 2250 having a computer-readable medium 2255 and that is configured to maintain and provide access to information corresponding to the indication of the disease. In an embodiment, the patient records device may be substantially similar to the patient records device 1790 described in conjunction with FIG. 20. The system also includes a transmitter device, illustrated as a communications circuit 2258, operable to broadcast a signal indicative of the disease. In an embodiment, the broadcast of the signal indicative of the disease may be a pushed broadcast or a pulled broadcast.

The environment 2200 also includes a computing device 2290 having a user interface, illustrated as a display 2292, and operable to communicate with the patient information device 2250 and to receive the signal indicative of the disease broadcast by the communications circuit 2258 of the patient information device. In an embodiment, the computing device is also operable to communicate with the neuromodulation device 1460. In an embodiment, the computing device is operable to display the indication of the disease broadcast by the communications circuit 2258 to a user, such as the mammal or a third-party user (not illustrated). In an embodiment, the computing device having a user interface may include the thin computing device 20 described in conjunction with FIG. 1, or the computing device 110 described in conjunction with FIG. 2. In another embodiment, the computing device may include a specialized user interface (not shown).

In an embodiment, the sensor device 2220 may include a sensor head 2222, a signal generating circuit 2223, a sensor controller 2224, a processor circuit 2225, a sensor output conditioning circuit 2226, a communications circuit 2228, or other circuit(s) 2229. In an embodiment, the patient assessment device 2230 may include an artificial intelligence based assessment circuit 2232, a library based assessment circuit 2234, a computer-readable medium 2235, a processor circuit 2236, a communications circuit 2238, or other circuit(s) 2239. In an embodiment, the patient information device 2250 may include a records management circuit 2252, a processor circuit 2254, a computer-readable medium 2255, a records privacy circuit 2256, a communications circuit 2258, or other circuit(s) 2259.

In an embodiment, the sensor device 2320 includes a sensor device operable to detect a property of a mammal 2205 absent a direct conductive, electrical, or physical contact with the mammal. In an embodiment, the sensor device includes a contactless sensor device operable to at least one of electronically, sonically, acoustically, thermally, radiatively, or chemically detect a property of a mammal without a direct contact with the mammal. In an embodiment, the sensor device includes a contactless sensor device operable to detect a property of a mammal without a direct contact with the mammal, and to transmit a signal indicative of the detected property of a mammal. In an embodiment, the signal may be transmitted wirelessly or via an electrical conductor.

In an embodiment, the patient assessment device 2230 includes a patient assessment device physically distinct and spatially apart from the sensor device 2220. In an embodiment, the patient assessment device includes a patient assessment device operable to evaluate the detected property of the mammal 2205 for an impairment or ailment potentially treatable by a neuromodulation treatment regimen. In an embodiment, the patient assessment device includes a patient assessment device operable to receive a signal indicative of the detected property of a mammal and to evaluate the detected property of the mammal for an indicator of a disease. In an embodiment, the mammal assessment device is operable to receive the signal indicative of the detected property of a mammal wirelessly or via an electrical conductor. In an embodiment, the patient assessment device includes a patient assessment device operable to evaluate the detected property of the mammal for a physiological characteristic of the mammal and to identify a disease of the mammal in response to the evaluated physiological characteristic of the mammal. In an embodiment, the patient assessment device includes a patient assessment device operable to evaluate the detected property of the mammal for an indicator of a disease and to determine a neuromodulation treatment regimen in response to the indicator of the disease of the mammal. In an embodiment, the patient assessment device includes a patient assessment device operable to evaluate the detected property of the mammal for an indicator of a disease and to determine a neuromodulation treatment regimen in response the indicator of a disease according to a selected outcome.

In an embodiment, the patient assessment device 2230 includes a patient assessment device operable to evaluate the detected property of the mammal 2205 for an indicator of a disease and to determine a therapeutic neuromodulation treatment regimen in response to the indicator of a disease. In an embodiment, a therapeutic neuromodulation treatment regimen includes a neuromodulation treatment regimen that is efficacious, or indicated as effective to at least one of change, alter, control, or stabilize a state of the mammal. In an embodiment, the patient assessment device includes a patient assessment device operable to evaluate the detected property of the mammal for an indicator of a disease and to transmit a signal responsive to the indicator of a disease. In an embodiment, the signal may be transmitted wirelessly or via an electrical conductor. In an embodiment, the patient assessment device includes an electronically implemented patient assessment device operable to evaluate the detected property of the mammal for an indicator of a disease. In an embodiment, the patient assessment device includes a patient assessment device operable to evaluate using an artificial intelligence technique the detected property of the mammal for an indicator of a disease. In an embodiment, the patient assessment device includes a patient assessment device operable to evaluate the detected property of the mammal for an indicator of a disease using digitally maintained table indicating a possible correlation between the indicator of a disease and the detected property. In an embodiment, the patient assessment device and the mammal information device 2250 share at least a portion of a common chassis.

In an embodiment, the patient records device 2250 is configured to maintain and provide access to information corresponding to the indication of the disease and information corresponding to the neuromodulation treatment regimen responsive to the characteristic of a symptom of the mammal 2205.

In an embodiment, the system 2203 includes a user interface operable to electronically output a human-perceivable indication of the disease in response to the broadcast signal indicative of the disease. In an embodiment, the user interface may be provided by the display 2292 of the computing device 2290. For example, the display may electronically output a human-perceivable indication of a seizure, or arrhythmia characteristic. In an embodiment, the patient information device 2250 and the user interface share at least a portion of a common chassis. In an embodiment, the user interface includes a user interface operable to electronically output a visual or audible indication of the disease in response to the broadcast signal indicative of the disease. In an embodiment, the user interface includes a user interface operable to electronically output a human-perceivable indication of the disease in response to the broadcast signal indicative of the disease. The user interface is also operable to output a proffered neuromodulation treatment regimen responsive to the disease. For example, the proffered neuromodulation treatment regimen may include a mild heart pacing intervention, significant heart pacing intervention, or neuromodulation treatment regimen to a vagus nerve. In an embodiment, the user interface includes a user interface operable to electronically display a human-perceivable indication of the disease in response to the broadcast signal indicative of the disease. In an embodiment, the user interface includes a user interface operable to electronically display a human-perceivable visual, audible, or tactile indication of the disease in response to the broadcast signal indicative of the disease. In an embodiment, the user interface includes a user interface operable to electronically output a human-perceivable indication of the disease in response to the broadcast signal indicative of the disease and receive a human-originated input responsive to the indication of the disease. In an embodiment, the user interface includes a user interface operable to electronically output (i) a human-perceivable indication of the disease in response to the broadcast signal indicative of the disease and (ii) a proffered neuromodulation treatment regimen responsive to the disease. The user interface is also operable to receive a human-originated input responsive to the proffered neuromodulation treatment regimen. In an embodiment, the user interface includes a user interface operable to electronically output a human-perceivable indication of the disease to the mammal or to a person other than the mammal in response to the broadcast signal indicative of the disease.

In an embodiment, the system 2203 includes a treatment controller operable to control an administration of a neuromodulation treatment regimen to a nervous system component 2207 of the mammal 2205. In an embodiment, the treatment controller is illustrated as treatment controller circuit 1464 of the neuromodulation device 1460. In another embodiment, the treatment controller may be a stand-alone device (not illustrated). In an embodiment, patient information device 2250 and the treatment controller device share at least a portion of a common chassis. In an embodiment, the treatment controller includes a treatment controller operable to control an administration of a neuromodulation treatment regimen to a nervous system component of the mammal in response to a human-originated input responsive to a proffered neuromodulation treatment regimen. In an embodiment, the treatment controller includes a treatment controller operable to control an administration of a neuromodulation treatment regimen to a nervous system component of the mammal and to communicate with a neuromodulation device physically associated with the mammal. In an embodiment, the treatment controller is operable to communicate with the neuromodulation device using a wireless connection or an electrical conductor. In an embodiment, the treatment controller is operable to communicate with the neuromodulation device physically associated with the mammal using a network, such as the Internet, a global computer network, a private network, a LAN, or a cellular network.

In an embodiment, the system 2203 includes the neuromodulation device 1460, which is operable to administer a neuromodulation treatment regimen to a nervous system component 2207 of the mammal 2205. In an embodiment, the neuromodulation device is operable to administer a neuromodulation treatment regimen to a nervous system component 2207 of the mammal in response to a command received from the treatment controller in response to an input initiated by the mammal, or in response to an input initiated by a health care provider. In an embodiment, the system includes an illumination source 1430 operable to illuminate at least a portion of the mammal with an energy to which the contactless sensor device 2220 is responsive.

FIG. 29 also illustrates another example of the system 2203. The system includes the sensor device 2220 operable to detect a property of the mammal 2205 without a direct contact with the mammal. The system includes the patient assessment device 2230 operable to evaluate the detected property of the mammal for an indicator of a disease, disorder, or symptom potentially treatable by a neuromodulation treatment regimen (hereafter referred to as "disease"). The system includes the user interface device, illustrated as the user interface 2292 of the computing device 2290, operable to electronically output a human-perceivable information responsive to the disease. The system includes the patient information device 2250 having the computer-readable medium 2255, and configured to maintain information corresponding to the indicator of a disease, to maintain information corresponding to the indication of a human-initiated authorization to initiate a neuromodulation treatment regimen to a nervous system component of the mammal, and to provide access to the maintained information.

In an embodiment of the another example of the system 2203, the user interface 2292 of the computing device 2290 includes a user interface device operable to electronically output a human-perceivable information responsive to the indicator of a disease to the mammal or to a third person, and to electronically receive an indication of a human-initiated authorization to initiate a neuromodulation treatment regimen to a nervous system component of the mammal. In an embodiment of the another example of the system 2203, the patient information device having a computer-readable medium. The patient information device is configured to maintain information corresponding to the indicator of a disease, to maintain information corresponding to the indication of a human-initiated authorization to initiate a neuromodulation treatment regimen to a nervous system component of the mammal, and to provide access to the maintained information. In an embodiment of the another example of the system 2203, the system includes the neuromodulation device 1460 operable to deliver a neuromodulation treatment regimen to a nervous system component of the mammal.

Figure 30:
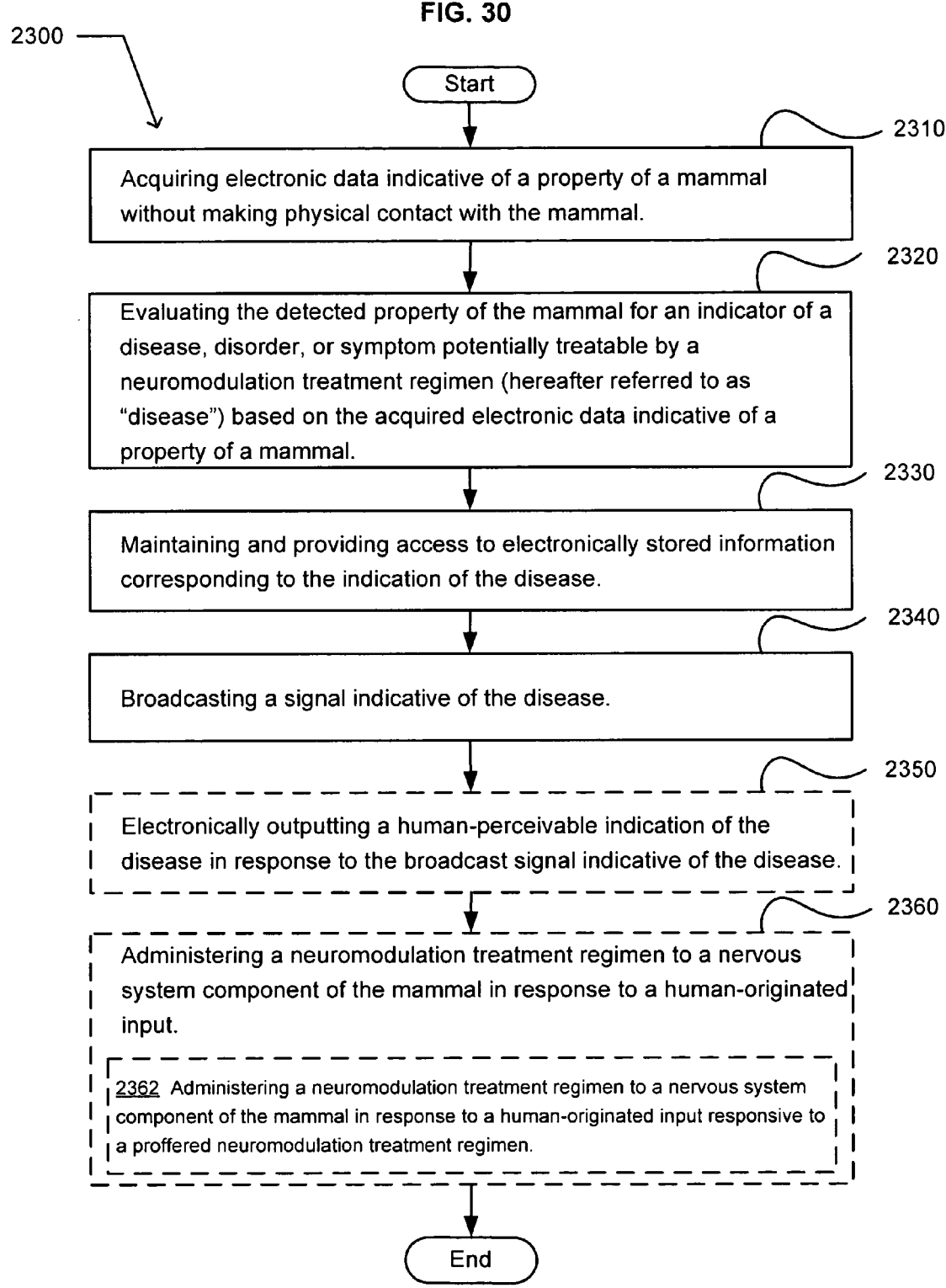
FIG. 30 illustrates an example operational flow in which embodiments may be implemented.

FIG. 30 illustrates an example operational flow 2300. After a start operation, the operational flow includes a sensing operation 2310. The sensing operation includes acquiring electronic data indicative of a property of a mammal without making physical contact with the mammal. In an embodiment, the sensing operation may be implemented using the sensor device 2220 described in conjunction with FIG. 29. A diagnosis operation 2320 includes evaluating the detected property of the mammal for an indicator of a disease, disorder, or symptom potentially treatable by a neuromodulation treatment regimen (hereafter referred to as "disease") based on the acquired electronic data indicative of a property of a mammal. In an embodiment, the diagnosis operation may be implemented using the patient assessment device 2230. A records operation 2330 includes maintaining and providing access to electronically stored information corresponding to the indication of the disease. In an embodiment, the records operation may be implemented using the patient information device 2250. A distribution operation 2340 includes broadcasting a signal indicative of the disease. The distribution operation may be implemented using the communications module 2258 described in conjunction with FIG. 29. The operational flow includes an end operation.

In an embodiment, the operational flow 2300 may include a dissemination operation 2350. The dissemination operation includes electronically outputting a human-perceivable indication of the disease in response to the broadcast signal indicative of the disease. In an embodiment, the dissemination operation may be implemented using the computing device 2290 having a user interface, illustrated as a display 2292. In an embodiment, the operational flow may include a treatment operation 2360. The treatment operation includes administering a neuromodulation treatment regimen to a nervous system component of the mammal in response to a human-originated input. In an embodiment, the treatment operation includes substantially transforming a physiological aspect of the mammal by administering a neuromodulation treatment regimen to a nervous system component of the mammal in response to a human-originated input responsive to a proffered neuromodulation treatment regimen. In an embodiment, the treatment operation may be implemented using the neuromodulation device 1460. In an embodiment, the treatment operation may include at least one additional operation, such as the operation 2362. The operation 2362 includes administering a neuromodulation treatment regimen to a nervous system component of the mammal in response to a human user-originated input that is responsive to a proffered neuromodulation treatment regimen.

Figure 31:
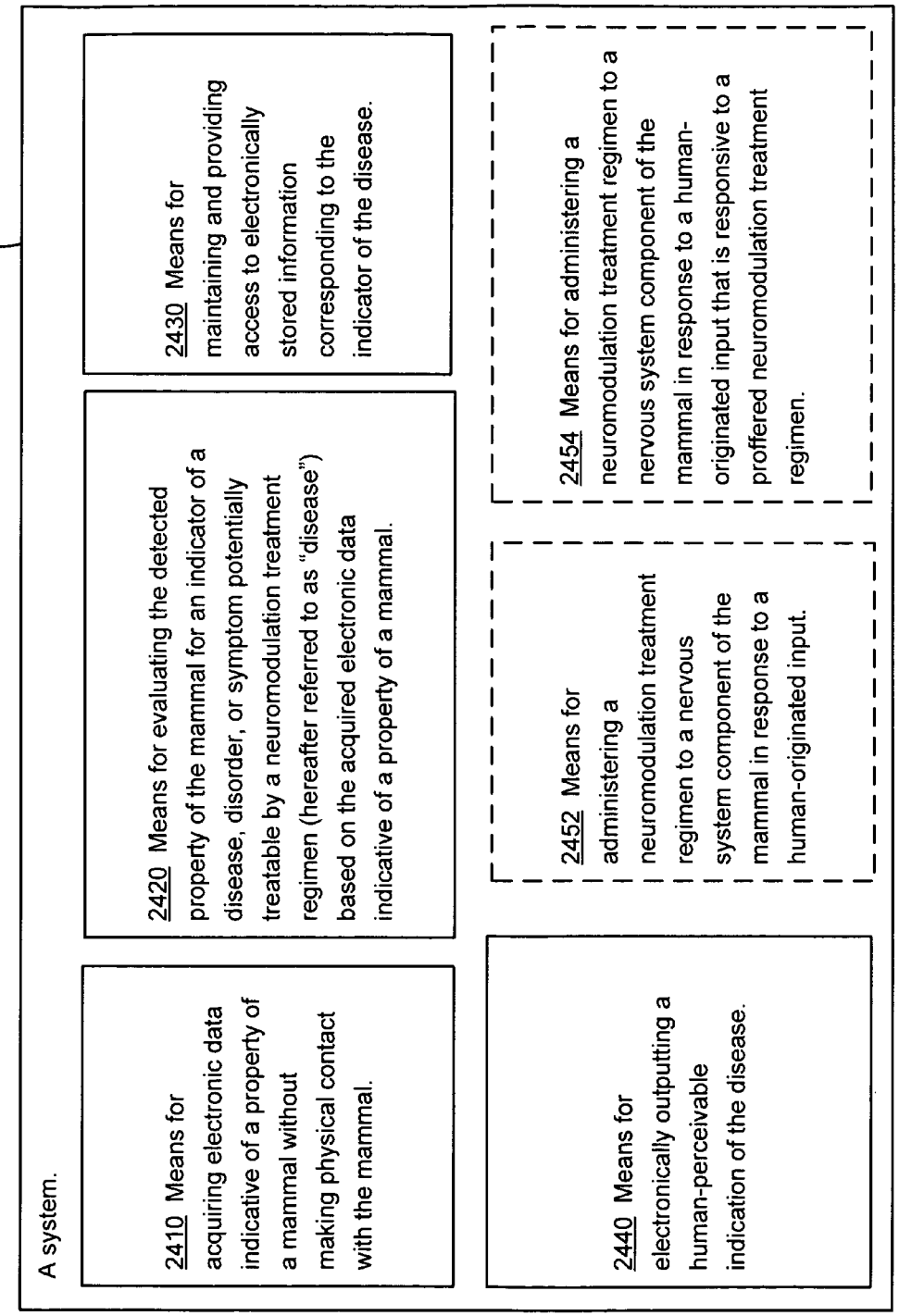
FIG. 31 illustrates an example system in which embodiments may be implemented.

FIG. 31 illustrates an example system 2400. The system includes means 2410 for acquiring electronic data indicative of a property of a mammal without making physical contact with the mammal. The system also includes means 2420 for evaluating the detected property of the mammal for an indicator of a disease based on the acquired electronic data indicative of a property of a mammal. The system further includes means 2430 for maintaining and providing access to electronically stored information corresponding to the indicator of the disease. The system also includes means 2440 for electronically outputting a human-perceivable indication of the disease.

In an embodiment, the system 2400 includes means 2452 for administering a neuromodulation treatment regimen to a nervous system component of the mammal in response to a human-originated input. In an embodiment, the system includes means 2454 for administering a neuromodulation treatment regimen to a nervous system component of the mammal in response to a human-originated input. In an embodiment, the system includes means 2456 for administering a neuromodulation treatment regimen to a nervous system component of the mammal in response to a human-originated input that is responsive to a proffered neuromodulation treatment regimen.

In certain embodiments, communications between disclosed elements may be subject to security measures, such as encryption.

EXAMPLES

Example 1

System and Method for Treating a Health Condition Including Sensor Devices Associated with an Object and Able to Remotely Detecting Cardiac Function A system described herein, or a method, can be used to identify and treat a health condition affecting the heart of a human patient, for instance an abnormal heart rhythm such as atrial fibrillation (AF). Atrial fibrillation is the most common long-term arrhythmia and the most common arrhythmia-related cause of hospital admission, with greater than 2 million Americans and greater than 150,000 new cases treated each year. This number is expected to rise with an aging population since incidence is associated with advanced age. Atrial fibrillation involves chaotic and rapid (tachy) contractions of the atria that overload the atrial-ventricular (AV) node causing irregular, often fast, ventricular contractions. Such arrhythmia can be identified by measuring the heartbeat intervals and electrical activity of the heart, as through an electrocardiogram (ECG). For identifying and treating atrial fibrillation, the system would include one or more sensor devices able to remotely sense heartbeat intervals and ECG readings by measuring small electrical potentials using a high input impedance electrometer. Examples of such sensor devices can be found in U.S. Patent Application Pub. No. 20060058694, supra; WO 2003/048789, supra; Harland, Meas. Sci. Technol., supra; Prance et al., 2007 Journal of Physics: Conference Series, supra. Such a sensor device would provide noninvasive and remote monitoring, and could be worn by the patient, for instance in or on clothing or jewelry, such as in a wrist band in non-conductive contact with the body, for example as described by U.S. Patent Application Pub. No. 20060058694, supra; WO 2003/048789, supra; and C. J. Harland et al., *High resolution ambulatory electrocardiographic monitoring using wrist-mounted electric potential sensors*, 14 Meas. Sci. Technol. 923-928 (2003). Instead or in addition, the one or more sensor devices could be included in or associated with a piece of furniture, or with electronics such as a personal computer, or with some other item within, e.g., one meter from the patient. For example, the one or more sensor devices able to measure electric potentials could be embedded in an object, such as a desk, bed or chair, in direct but non-conductive contact with the patient, as described by U.S. Pat. No. 7,245,956, supra. The patient would be monitored by the one or more sensor devices, while at rest, while working at a desk or a computer, for example at a place of employment, or while engaged in activities, for example outside of the home.

Information gathered by the one or more sensor device would be communicated to a computing device of the system, either via direct connection, for example when the sensor device is embedded in a computer, or wirelessly, for example using radiowaves or ultrasound waves, or Bluetooth technology. The computing device could be a computer, such as a hand-held computer or a personal computer, and could be part of a network and able to access a central database. The computer could include a treatment regimen circuit or treatment decision circuit. The computer and its associated circuitry would process the information to determine, for example, whether the heart is beating within normal limits for the patient or if the ECG readings are outside set parameters. Such processing would include application of a computer program and could include input from a user, for example the patient or a health care provider. If observed abnormalities are determined by the computer or the user to constitute a pathology, e.g. atrial fibrillation, the system and/or user can would signal the neuromodulation device to initiate a neuromodulation treatment.

Treatment for atrial fibrillation can include affecting a portion of the autonomic nervous system, especially one or more vagal nerve or efferent thereof. Control of heart rate and rhythm is mediated by the autonomic nervous system via opposite/complementary signals through sympathetic and parasympathetic (vagal) nerve fibers to promote respectively excitation or at rest signaling. The parasympathetic fibers originate at the medulla oblongata, and the cervical vagus nerves run parallel to the carotid arteries. Atrial (and to a lesser degree ventricular) myocardium is also innervated by vagal efferent nerves. The right vagus nerve primarily innervates the sinoatrial (SA) node (which initiates the beat at the right atrium) and upon stimulation slows nodal firing; the left vagus innervates the AV node (which receives and imparts the impulse) and moderates ventricular conduction of the beat. During atrial fibrillation, the atria discharge at a high rate. The ventricular rate at this time is rapid and irregular and is dependent on the conducting ability of the AV node, which is often blocked. Thus, influencing (e.g. stimulating or blocking) the vagus nerves can affect the electrophysiology of the heart and be used in the treatment of pathologies such as atrial fibrillation.

Once signaled by the computer, the neuromodulation device would initiate one or more neuromodulating stimulus, for example by providing a current to nervous system component that is a vagus nerve or related fiber. In some forms such a neuromodulating stimulus would initiate a stimulating action potential; in some forms such a neuromodulating stimulus would block an action potential. A number of devices and systems are known in the art that can provide a stimulating or blocking neuromodulation to a vagal nerve. In one example, the system and method used to treat a heart condition, such as atrial fibrillation, would include one or more partially or completely implanted neuromodulation device responsive to instructions transmitted from the computer or network. Treatment would include, for example, the computer or network, as part of its programming, circuitry, or in response to commands from the user, communicating instructions wirelessly to the one or more partially or completely implanted neuromodulation devices, which would then provide neuromodulation stimulus to one or more vagal nerves. For instance, the computer, having processed the information from the remote sensor device, determines the need for treatment, and, as part of its programming or instructed to do so by a user, the computer sends out a wireless signal to a receiver and controller associated with the partially or completely implanted neuromodulation source. Such wireless signaling is described in U.S. Pat. No. 7,321,793, Vagal stimulation for atrial fibrillation therapy to O. Ben-Ezra et al. In some cases, the neuromodulation device would include a portion, such as one or more electrodes with leads, in direct contact with tissue and controlled by a pulse generator, which may also be implanted, perhaps at a site distant from the electrodes, or it may be external and provide the pulse wirelessly. Examples of implanted and external pulse generators are described in U.S. Pat. No. 7,496,404 to Meadows et al., supra and U.S. Pat. No. 7,146,217 to Firlik et al., supra, and in U.S. Patent Application Pub. No 20050143787, Method and system for providing electrical pulses for neuromodulation of vagus nerve(s), using rechargeable implanted pulse generator, by B. Boveja. Additional examples of implanted generators include those used in Northstar's Renova System or in St. Jude's SCS systems, including examples powered by a long-life battery, a rechargeable system, or an external power source. In some cases, the neuromodulation device would include a portion, such as a controller, external to the body of the patient and coupled with the computer or network. Such an external controller would be programmed to accept information or instructions from the computer, network, or remote sensor device and, in response to the received information, to transmit a wireless signal to one or more implanted portion of the neuromodulation device, for example a pulse generator, which would then initiate neuromodulation such as stimulating or blocking a vagus nerve or fiber. Examples of external controllers able to receive information and communicate wirelessly with pulse generators, which may be implanted separately from the electrodes, or may be wholly integrated or wholly external to the electrodes, are described in U.S. Pat. No. 7,146,217 to Firlik et al., supra. Examples of an external controller able to communicate with an implanted pulse generator are described in U.S. Pat. No. 7,496,404 to Meadows et al., supra and U.S. Pat. No. 7,127,297 Multiprogrammable tissue stimulator and method to Law, et al. Examples of external components and vagal stimulation devices are described in U.S. Patent Application Pub. No 20050143787 to B. Boveja, supra.

In some cases, as an alternative or in addition to wireless communication between the computer and the neuromodulation device, the computer would provide an indicator, such as an audio or visual indicator or report, to the user instructing the user to interface the computer with the neuromodulation device. For example, the user would interface the computer with portions of the neuromodulation device. For example a magnetic transcutaneous external controller or a radiofrequency controller, which in turn would communicate with the implanted portion of the neuromodulation device. Examples of such external components are described in U.S. Patent Application Pub. No. 20050131467, Method and apparatus for electrical stimulation therapy for at least one of atrial fibrillation, congestive heart failure, inappropriate sinus tachycardia, and refractory hypertension, by B. Boveja and U.S. Pat. No. 7,127,297 to Law, et al., supra. In some cases, wireless transmission would also serve as a means to power the implanted portion of the neuromodulation device, as described in U.S. Patent Application Pub. No 20050143787, Method and system for providing electrical pulses for neuromodulation of vagus nerve(s), using rechargeable implanted pulse generator, by B. Boveja and U.S. Pat. No. 7,146,217 to Firlik et al., supra. Alternatively or in addition, a portable energy source may provide energy transcutaneously, for example to recharge an implanted device as described in U.S. Pat. No. 7,496,404 to Meadows et al., supra. In some cases, the power source will be entirely external and energy transmitted to the implanted device, for example by radiofrequency. An example of such an external energy source is the St. Jude's Renew Radiofrequency SCS System.

In an alternative to a neuromodulation device implanted in contact with a vagus nerve, at least a portion of the implanted neuromodulation device would be adjacent to the nerve, for example within a nearby blood vessel through which it could provide the neuromodulation stimulus to the nerve. Such a device, for example, is described in U.S. Patent Application Pub. No. 20050187584, Vagal nerve stimulation using vascular implanted devices for treatment of atrial fibrillation, by S. Denker et al. or in U.S. Patent Application Pub. No. 20060259085, Neural stimulation system with pulmonary artery lead, by Y. Zhang.

In some cases, the computer and its circuitry and programming would determine that the optimum treatment for the identified atrial fibrillation would include, for example, the system or method and its neuromodulation device restoring a normal sinus rhythm (NSR). In other situations the optimum treatment would include continuing atrial fibrillation under controlled circumstances, for example as a means of avoiding formation of blood clots that can occur during repeated episodes of AF/NSR. In some cases, treatment for the atrial fibrillation provided by the system or method would include providing at least two forms of neuromodulation, for example inducing an action potential and inhibiting an action potential, which could be the induced potential subsequently inhibited, or a second action potential, for example in a separate nerve. In some cases, treatment for atrial fibrillation provided by the system or method would include providing neuromodulation having a particular set of parameters, such as, for example, providing a current of a particular amplitude such as between about 2 and about 10 milliamps, or frequency, or providing pulses of current, for example of a duration lasting between about 0.1 and about 4 milliseconds, or for example repeated in intervals of between about 2 and about 10 milliseconds in, for instance, intermittent, repetitive, or random bursts. In some cases, treatment for atrial fibrillation provided by the system or method would include providing neuromodulation only under particular circumstances, for example during sleep or wakefulness, during a point in the circadian rhythm, or during a point in the cardiac cycle; in this case the system or method could use additional information from the one or more sensors or from a component of the computer, such as a clock. Examples of devices and methods which could be used to provide forms of neuromodulation for treatment of atrial fibrillation are described in U.S. Patent Application Pub. No. 20080091241, Vagal stimulation for cardioversion of atrial fibrillation, by O. Ben-Ezra et al; U.S. Patent Application Pub. No. 20080125825, Therapeutic maintenance of atrial fibrillation by electrical stimulation, by T. David; U.S. Patent Application Pub. No. 20040193231, Selective nerve fiber stimulation for treating heart conditions, by T. David; U.S. Patent Application Pub. No. 20080125827, Selective nerve fiber stimulation for treating heart conditions, by T. David; U.S. Patent Application Pub. No. 20060271115, Vagal stimulation for anti-embolic therapy, by O. Ben-Ezra et al; or U.S. Pat. No. 7,321,793, Vagal stimulation for atrial fibrillation therapy, to O. Ben-Ezra et al. Additional neuromodulation devices may be used to affect additional nerves, such as efferent or afferent to the vagus nerves, sympathetic nerves, or myocardial tissue. Such devices are described, for example, in U.S. Patent Application Pub. No. 20080091245, Combined parasympathetic stimulation and cardiac pacing, by O. Ben-Ezra et al.

During and following treatment, monitoring the patient via the sensor device can continue and the treatment can be adjusted accordingly as determined by the computer of the system, via its programming or user input. In addition, the neuromodulation device, perhaps as part of the controller, would store information or report information, for example to a separate computer system or a network, regarding the neuromodulation treatment provided, such as the type and duration of stimulation applied to a vagus nerve.

Example 2

System and Method for Treating a Health Condition Including Sensor Devices for Remotely Detecting Cardiac Function in a Human Occupying a Space A system described herein, or a method, can be used to identify and treat a health condition affecting the heart of a human patient, for instance an abnormal heart rhythm such as atrial fibrillation. Arrhythmia associated with atrial fibrillation can be identified by measuring the heartbeat intervals and electrical activity of the heart, as through an ECG. For identifying and treating atrial fibrillation, the system would include one or more sensor devices able to remotely sense heartbeat intervals and ECG readings by providing and receiving an electromagnetic signal directed at and reflected from the patient. Such sensor devices using illuminating, reflected, electromagnetic, including radiofrequency (RF), or microwave signals are described in U.S. Pat. No. 7,272,431, Remote-sensing method and device to W. McGrath, U.S. Patent Application Pub. No. 20040123667, Remote-sensing method and device, by W. McGrath; and U.S. Patent Application Pub. No. 20080045832, Remote-sensing method and device, by W. McGrath. One or more of such sensor devices, which could include or be arranged as a sensor array, would be deployed, for example, throughout a room, perhaps as part of a smart room network. The patient would be monitored continuously while occupying the space, for example while at sleep or while performing normal daily activities within a room or home.

The system or method for treating a heart condition such as atrial fibrillation would include a computing device and its related software and circuitry. Information gathered by the one or more sensor devices would be wirelessly communicated to the computing device. The computing device could be a computer, such as a hand-held computer or a personal computer, and able to access a central database. The computer could include a treatment regimen circuit or treatment decision circuit. The computer system would receive information from the one or more sensor devices regarding the heart rate and ECG readings. The computer would process the received information utilizing stored information such as a medical history database of the patient or treatment modalities. The computer would then determine the appropriate treatment, at least partly based on the stored information such as a table or database of treatments recommended in response to the identified condition, such as normal sinus rhythm or atrial fibrillation. The appropriate treatment in some cases would include no neuromodulation. As a further example, if the received information includes a heart rate and heart rhythm indicative of rapid atrial fibrillation, the computer and its treatment regimen circuit and treatment decision circuit determines the optimum treatment to be stimulation of the vagus nerve, which would slow the heart, allowing the heart to more completely relax and the ventricles to experience increased filling. With larger diastolic volumes, the heart beats more efficiently. The computer signals the neuromodulation device to initiate treatment. Alternatively, the computer provides information on the sensed property or condition, the identified rapid atrial fibrillation, and the recommended neuromodulation to the user, for example through a screen or hardcopy printout. The user, for example the patient or health care provider, makes the final decision for treatment and enters the decision into the computer system via an interface, such as a keyboard, touch screen, mouse, or stylus, and the resultant signal is sent to the neuromodulation device.

Once signaled by the computer, the neuromodulation device would initiate a neuromodulating stimulus, for example by providing a current to the vagus nerve or related fiber. In one example, the system and method used to treat a heart condition, such as atrial fibrillation, would include one or more partially or completely implanted neuromodulation device responsive to instructions transmitted from the computer. Treatment would include, for example, the computer or network, as part of its programming, circuitry, or in response to commands from the user, communicating instructions wirelessly to the one or more partially or completely implanted neuromodulation devices, which would then provide neuromodulation stimulus to the one or more vagal nerves. For instance, having processed the information from the remote sensor device and determined that the best treatment is stimulation of the vagal nerve to slow the heart rate, the computer sends out a wireless signal to a receiver and controller associated with the partially or completely implanted neuromodulation source. Such wireless signaling is described, for example, in U.S. Pat. No. 7,321,793, to O. Ben-Ezra et al., supra. In some cases, the neuromodulation device would include a portion, such as one or more electrodes with leads, in direct contact with tissue and controlled by a pulse generator, which may also be implanted, perhaps at a site distant from the electrodes, or it may be external and provide the pulse wirelessly. Examples of implanted and external pulse generators are described in U.S. Pat. No. 7,496, 404 to Meadows et al., supra and U.S. Pat. No. 7,146,217 to Firlik et al., supra, and in U.S. Patent Application Pub. No 20050143787, Method and system for providing electrical pulses for neuromodulation of vagus nerve(s), using rechargeable implanted pulse generator, by B. Boveja. Additional examples of implanted generators include those used in Northstar's Renova System or in St. Jude's SCS systems, including examples powered by a long-life battery, a rechargeable system, or an external power source. In some cases, the neuromodulation device would include a portion, such as a controller, external to the body of the patient and coupled with the computer or network. Such an external controller would be programmed to accept information or instructions from the computer, network, or remote sensor device and, in response to the received information, to transmit a wireless signal to one or more implanted portion of the neuromodulation device, for example a pulse generator, which would then provide neuromodulation such as stimulating or blocking a vagus nerve or fiber. Examples of external controllers able to receive information and communicate wirelessly with pulse generators, which may be implanted separately from the electrodes, or may be wholly integrated or wholly external to the electrodes, are described in U.S. Pat. No. 7,146,217 to Firlik et al., supra. Examples of an external controller able to communicate with an implanted pulse generator are described in U.S. Pat. No. 7,496,404 to Meadows et al., supra and U.S. Pat. No. 7,127,297 to Law, et al, supra. Examples of external components and vagal stimulation devices are described in U.S. Patent Application Pub. No 20050143787 to B. Boveja, supra.

In some cases, the computer and its circuitry and programming would determine that the optimum treatment for the atrial identified fibrillation would include, for example, the system or method and its neuromodulation device restoring a normal sinus rhythm (NSR). In other situations the optimum treatment would include continuing atrial fibrillation under controlled circumstances, for example as a means of avoiding formation of blood clots that can occur with during repeated episodes of AF/NSR. In some cases, treatment for atrial fibrillation provided by the system or method would include providing at least two forms of neuromodulation, for example inducing an action potential and inhibiting an action potential, which could be the induced potential subsequently inhibited, or a second action potential, for example in a separate nerve. In some cases, treatment for atrial fibrillation provided by the system or method would include providing neuromodulation having a particular set of parameters, such as, for example, providing a current of a particular amplitude such as between about 2 and about 10 milliamps, or frequency, or providing pulses of current, for example of a duration lasting between about 0.1 and about 4 milliseconds, or for example repeated in intervals of interval of between about 2 and about 10 milliseconds in, for instance, intermittent, repetitive, or random bursts. In some cases, treatment for atrial fibrillation provided by the system or method would include providing neuromodulation only under particular circumstances, for example during sleep or wakefulness, during a point in the circadian rhythm, or during a point in the cardiac cycle; in this case the system or method could use additional information from the one or more sensors or from the computer, such as a clock. Examples of devices and methods which could be used to provide such forms of neuromodulation for treatment of atrial fibrillation are described in U.S. Patent Application Pub. No. 20080091241, Vagal stimulation for cardioversion of atrial fibrillation, by O. Ben-Ezra et al; U.S. Patent Application Pub. No. 20080125825, Therapeutic maintenance of atrial fibrillation by electrical stimulation, by T. David; U.S. Patent Application Pub. No. 20040193231, Selective nerve fiber stimulation for treating heart conditions, by T. David; U.S. Patent Application Pub. No. 20080125827, Selective nerve fiber stimulation for treating heart conditions, by T. David; U.S. Patent Application Pub. No. 20060271115, Vagal stimulation for anti-embolic therapy, by O. Ben-Ezra et al; or U.S. Pat. No. 7,321,793, Vagal stimulation for atrial fibrillation therapy, by O. Ben-Ezra et al. Additional neuromodulation devices may be used to affect additional nerves, such as efferent or afferent to the vagus nerves, sympathetic nerves, or myocardial tissue. Such devices are described, for example, in U.S. Patent Application Pub. No. 20080091245, Combined parasympathetic stimulation and cardiac pacing, by O. Ben-Ezra et al.

In some cases, the computer of the system would be programmed to continue monitoring via the remote sensor devices and the signal generator, which would send instructions, for example different or additional instructions, to the neuromodulation device. During and following treatment, monitoring the patient via the sensor device can continue and the treatment can be adjusted accordingly as determined by the computer of the system, via its programming or user input. In addition, the neuromodulation device, perhaps as part of the controller, would store information or report information, for example to a separate computer system or a network, regarding the neuromodulation treatment provided, such as the type and duration of stimulation applied to a vagus nerve.

Example 3

System and Method for Remotely Detecting Effects of a Sleep Disorder in an Active Person and Providing Treatment The system or a method described herein can be used to treat a sleep disorder or an effect thereof in an adult human person performing an activity. Hypersomnia, which can be described as an excessive need for sleep, excessive daytime sleepiness (EDS), and episodes of involuntary sleep ("sleep attacks") is known to be associated with a number of sleep-related disorders. In some persons these symptoms are characteristic sequelae of primary somnolence disorders, such as narcolepsy, idiopathic hypersomnia, recurrent hypersomnia like Kleine-Levin Syndrome, and nervous system disorders such as encephalitis. In other cases these symptoms present as secondary to a pathology, for example a sleep-related breathing disorder like sleep apnea, or are observed with certain diseases, such as nervous system disorders like Parkinson's Disease or epilepsy, or in patients taking certain medications, e.g. dopamine agonists. For additional description of sleep disorders see e.g., J. Black et al., *Narcolepsy and Syndromes of Primary Excessive Daytime Somnolence*, 24(3) Semin Neurol 271-282 (2004); J. Black et al., *Narcolepsy and Syndromes of Central Nervous System-Mediated Sleepiness*, 3(4) Focus 585-597 (2005); or American Academy of Sleep Medicine, *International Classification of Sleep Disorders: Diagnostic and Coding Manual* ($2^{nd}$ ed., 2005).

EDS and similar effects can present problems in daily living, for example occurring at inappropriate times, interrupting normal activities and even compromising safety; they can also be indicative of a problem requiring attention. A sleep-related disorder or an effect thereof, such as drowsiness or involuntary sleep, can be evaluated in a person performing an activity by determining a state of alertness, for example by measuring the characteristics of the pupil of an eye, such as pupil oscillation or miosis. In the system or method for treating a sleep-related disorder or effect thereof, such measurements would be obtained remotely by using a sensor device that includes a pupillometer. An example of a pupillometer sensor device using a camera or infrared optics is described in U.S. Pat. No. 6,097,295, Apparatus for determining the alertness of a driver, to M. Griesinger et al., or in U.S. Pat. No. 7,226,164, Method and apparatus for testing sleepiness, to M. Griesinger et al. A sensor device including a pupillometer could, for example, be incorporated into a computer camera, e.g. mounted in or on a computer monitor or the dashboard or interior of a vehicle, and would be configured to scan the pupils of an individual facing the camera. The sensor would monitor the person continuously or at programmed intervals.

Hypersomnia, narcolepsy, or other sleep-related disorders, or a related effect such as drowsiness can be evaluated through electroencephalography (EEG), for example by identifying one or more alterations in the distribution of energy in the person's EEG signal, or through electrooculogram (EOG) readings, as by identification of eye movements. Additional description of such evaluation using EEG, with or without EOG, is provided in U.S. Pat. No. 6,167,298, Devices and methods for maintaining an alert state of consciousness through brain wave monitoring, to R. Levin; and in C. Papadelis et al., *Monitoring sleepiness with on-board electrophysiological recordings for preventing sleep-deprived traffic accidents*, 118 Clinical Neurophysiology:1906-1922 (2007); *Indicators of Sleepiness in an ambulatory EEG study of night driving*, Proceedings of the 28th IEEE EMBS Annual International Conference (2006), and C. Marzano et al., *Slow eye movements and subjective estimates of sleepiness predict EEG power changes during sleep deprivation*, 30(5) Sleep 610-6 (2007). In some cases of detecting and treating a sleep-related disorder or an effect thereof, the system or method would remotely obtain EEG readings, with or without obtaining concurrent EOG readings. For example, the system or method would include one or more sensor devices having a high input impedance electrometer and configured to measure small electrical potentials, and could include additional devices for obtaining EOG readings. Examples of such sensor devices and technologies are described in U.S. Patent Application Pub. No. 20060058694, supra; WO 2003/048789, supra; C. J. Harland et al., *Remote detection of human electroencephalograms using ultrahigh input impedance electric potential sensors*, 81(17) Appl. Phys. Letters, 3284-3286 (2002); and R. J. Prance et al., *Adaptive Electric Potential Sensors for smart signal acquisition and processing*, 76 Journal of Physics: Conference Series 012025 (2007).

Sleep-related disorders such as narcolepsy, and related conditions such as fatigue or a transition from a state of wakefulness to drowsiness, can be assessed by examining a person's cardiac activity including the variability and patterns, such as in an ECG. In some cases, detecting and treating a sleep-related disorder or effect thereof, the system or method would obtain cardiac activity readings remotely, for example using one or more sensor devices. In one example, the system would include one or more sensor devices able to remotely sense heartbeat intervals and ECG readings by measuring small electrical potentials using a high input impedance electrometer. Examples of such sensor devices can be found in U.S. Patent Application Pub. No. 20060058694, supra; WO 2003/048789, supra; Harland, Meas. Sci. Technol. supra; Prance 2007 Journal of Physics: Conference Series, supra. In addition, the sensor devices could include an electromagnetic inductance device able to measure cardiac activity variability, as described in U.S. Pat. No. 7,254,439, Method and system for contactless evaluation of fatigue of an operator to D. Misczynski. As an alternative or in addition, the one or more sensor devices would include a device responsive to an electromagnetic signal directed at, illuminating, and reflected from the person to measure heartbeat intervals and ECG information. An example of such a device is described in U.S. Pat. No. 7,272,431, supra; U.S. Patent Application Pub. No. 20040123667, supra; or U.S. Patent Application Pub. No. 20080045832, supra.

In some cases, the one or more sensor devices would be worn by the person in a non-conductive contact with the body, for example a high input impedance electrometer worn in or on clothing or jewelry, such as in a wrist band. An example of such a sensor device is described in U.S. Patent Application Pub. No. 20060058694, supra; WO 2003/048789, supra; and C. J. Harland, 14 Meas. Sci. Technol. 923-928, supra. Alternatively or in addition, the sensor devices would be embedded in or associated with a piece of furniture, such as a chair or desk, or in the headrest of a car seat, or in an accessory such as a seat belt, or in a freestanding or tabletop appliance, or in electronics such as a personal computer, car computer, or related accessories. The sensor devices could be arranged as an array, for example embedded in a number of items or associated within a defined area, such as a vehicle or room. In some cases, the sensor device would acquire information regarding additional physiologic conditions. For example, respiration or temperature could also be obtained remotely using a sensor device as described in U.S. Pat. No. 7,272,431 supra; U.S. Patent Application Pub. No. 20040123667, supra; or U.S. Patent Application Pub. No. 20080045832, supra.

The system or method for detecting and treating a sleep-related disorder or an effect thereof would include monitoring of the alertness of an adult human person performing an activity such as driving a car or working at a computer work station. As described herein, the one or more sensor devices, which could be arranged in one or more arrays, would detect and accumulate information regarding the eye (e.g. pupillometry or EOG readings), brain waves (e.g. EEG readings), or heart activity (e.g. heart rate and ECG readings), or combinations thereof. For monitoring a person at a workstation, the sensors as described would be associated with, for example, the desk, chair, or computer of the workstation, and would be, e.g., within one meter of the person. Alternatively or in addition, the sensor devices would be associated with an area encompassing the workstation, for example placed on or near a wall of a room or work cubicle. For monitoring a person in a vehicle, the sensor devices would be embedded in the seat, e.g. in the headrest, belt, or seatback, e.g. within one meter of the person. Alternatively or in addition, the sensor devices would be associated with the interior space of the vehicle. The sensor devices of the system would communicate with the computer of the system and, directly or indirectly as through the computer, with the neuromodulation device of the system.

In some cases the system or method system or method for detecting and treating a sleep-related disorder or an effect thereof would include a patient confirmation device able to confirm that the person being monitored by the one or more sensor devices is the person requiring assessment and possible treatment. For example, when a person sitting in a car or at a workstation is being monitored by the sensor devices for alertness and evidence of drowsiness, the sensor devices would include a camera able to capture the image of the person's face. Information from the sensor devices, including the image, would be transmitted to the computer of the system, and programming within the computer would compare the acquired image information to stored image information. If the image matches the person to be treated, monitoring and treatment would continue. If the image does not match that of the person to be treated, monitoring ceases, in addition, a signal could be sent to the neuromodulation device blocking its activation. Additional sensor devices would be included in the system as needed, including, for example, a sensor for receiving radiofrequency identification signal such as those provided by a chip in a bracelet and carrying information regarding the wearer. Hardware and software able to distinguish between individuals is known in the art.

In the system or method for detecting and treating a sleep-related disorder or an effect thereof, information gathered by the one or more sensor devices would be communicated to a computing device of the system, either via a direct connection, e.g. when the sensor device is associated with the computer, or wirelessly. The computing device could be a computer, such as a hand-held computer or personal computer and could be part of a network. The computing device could include circuitry, for example a treatment regimen circuit or the treatment decision circuit. The computer and its associated circuitry would store or process the information, for example to determine the level of alertness of the person, using stored parameters. Processing would include application of a computer program and could include input from a user, for example the person or a health care provider. If measured parameters are determined by the computer or user to represent a decrease in alertness or onset of drowsiness, the system or user would signal the neuromodulation device to initiate a neuromodulation treatment.

Vagal nerve fibers have a wide distribution throughout the central nervous system (CNS), and vagal stimulation produces evoked potentials from the cerebral cortex, the hippocampus, the thalamus, and the cerebellum. Vagal afferent stimulation has been shown to elicit EEG synchronization or desynchronization and to affect sleep states. For detecting and treating a sleep disorder or an effect thereof, the system or method can provide stimulus or blocking neuromodulation signals to a vagal nerve using a neuromodulation device. In some cases, the neuromodulation device would include a partially or completely implanted device responsive to instructions transmitted from, for example, the computer of the system, possibly through a controller. For example, the computer of the system, as part of its programming or in response to commands from the user, would communicate instructions wirelessly to the one or more partially or completely implanted neuromodulation devices able to stimulate one or more vagal nerves. For example, the computer of the system, having processed the information from the sensor devices and as part of its programming or if instructed to do so by a user, would send out a radio signal to a receiver associated with at least a portion of an implanted neuromodulation device, such as a controller. Such wireless signaling is described, for example, in U.S. Pat. No. 7,321,793, Vagal stimulation for atrial fibrillation therapy to O. Ben-Ezra et al. Alternatively, the system or method would include a neuromodulation device in which a portion, such as a controller, is external to the body of the person. Such an external controller of the neuromodulation device would be programmed to accept information or instructions from the computer, network, or remote sensor device and, in response to the received information, to transmit a wireless signal to one or more implanted receiving portions of the neuromodulation device, which would then stimulate or block a vagus nerve or fiber. An example of such an external controller is described in U.S. Patent Application Pub. No. 20050131467 Method and apparatus for electrical stimulation therapy for at least one of atrial fibrillation, congestive heart failure, inappropriate sinus tachycardia, and refractory hypertension, 20050131467 by B. Boveja, supra. In some cases, wireless transmission to the receiver would also serve as a means to power the implanted portion of the neuromodulation device. An example of a neuromodulation device having an external controller and implanted portions is described in U.S. Patent No. U.S. Patent Application 20050143787 Method and system for providing electrical pulses for neuromodulation of vagus nerve(s), using rechargeable implanted pulse generator, by B. Boveja, supra. In some cases, instead of a neuromodulation device implanted in contact with a vagus nerve, the neuromodulation device would have at least a portion that is near the nerve, for example within a nearby blood vessel, through which it can stimulate the nerve. An example of such an intravascular neuromodulation device is described in U.S. Patent Application Pub. No. 20050187584, by S. Denker et al., supra. In some cases, for example as an alternative to wireless communication between the computer and neuromodulation device, the computer of the system would provide an indicator, such as an audio or visual indicator or report, to the person or health care provider instructing them to interface the computer with a portion of the neuromodulation device, such as a controller. For example, the computer would provide visual instructions on a computer screen indicating to the person to place an external controller, near the subcutaneous receiver of the neuromodulation device. The controller, when placed within range of the receiver, provides instructions to the neuromodulation device, for example to turn the device on or off. An example of a controller for use by a person or a health care provider is the Access programmer of the Activa Therapy System by Medtronic. Examples of neuromodulation devices and their control, for example using magnetic controllers are described in U.S. Pat. No. 6,760,626, Apparatus and method for treatment of neurological and neuropsychiatric disorders using programmerless implantable pulse generator system, to B. Boveja. Examples of neuromodulation devices and their control, for example using radiofrequency communication, are described in U.S. Pat. No. 7,127,297 to Law, et al., supra.

Treatment for a sleep-related disorder such as narcolepsy or a related condition such as excessive sleepiness, can be provided by the system or method in response to a detection of drowsiness. For example, when the drowsiness occurs during an activity such as driving or working at a computer, the one or more sensor devices of the system would detect the drowsiness by remote pupillography identifying a pattern of oscillations in the pupil, or by remote EEG recognizing bursts of alpha activity with increased synchrony, or both. The sensor devices would then communicate with the signal generator, or a computer of the system, which would in turn signal the neuromodulation device to initiate treatment. The neuromodulation device would respond to provide treatment, for example, by inducing an electrical stimulus to modulate the electrical activity of the vagus nerve and thereby alter the electrophysiology of the brain and desynchronize the EEG activity, by stimulation of the vagus nerve at a frequency in the range from 20 to 75 Hz and greater than 0.1 volt. An example of such treatment is described in U.S. Pat. No. 5,335,657, Therapeutic treatment of sleep disorder by nerve stimulation to T. Reese et al.

EDS and similar effects can be indicative of a problem requiring attention, such as sleep deprivation due to a sleeping-related disorder like apnea. Repeated periods of hypersomnolence or EDS can indicate onset, ongoing, or worsening of a disorder. In some cases, the sensor devices, the signal generator, or the computer would accumulate information regarding the number and duration of episodes of drowsiness, for example during daytime waking hours, and use this information to initiate treatment during sleep, with or without further sensing, perhaps remotely, of physiologic parameters, such as respiratory patterns that may be indicative of sleep apnea. Multiple or long-term readings would be obtained by the remote sensor devices and the information stored or processed for use in treatment. For example, as readings from the one or more sensor devices are obtained, stored, and processed, if certain predetermined parameters are met, e.g. a certain number of episodes of drowsiness occurring over a period of time, such as 12 hours or 24 hours, additional sensing by the sensor devices may be initiated at a later time, through programming or manually. In one example, the computer of the system processes information received from the sensor devices and determines that additional sensing is indicated during nocturnal sleep time, and the computer of the system signals the sensor devices to provide additional readings for heart rate or respiratory rate and assess them for variability indicative of the presence of apnea. If signaled by the sensor devices or computer, the neuromodulation device would provide treatment, for example providing an electrical stimulus to modulate the electrical activity of the vagus nerve to alter the electrophysiology and so synchronize the patient's EEG activity to promote sleep as a treatment to lessen occurrences of EDS.

In some cases, the computer of the system would be programmed to continue monitoring via the remote sensor devices and the signal generator, which would send instructions, for example different or additional instructions, to the neuromodulation device. During and following treatment, monitoring the person via the sensor device can continue and the treatment can be adjusted accordingly as determined by the computer of the system, via its programming or user input. In addition, the neuromodulation device, perhaps as part of the controller, would store information or report information, for example to a separate computer system or a network, regarding the neuromodulation treatment provided, such as the type and duration of stimulation applied to a vagus nerve.

Example 4

System and Method for Remotely Detecting Effects of a Sleep Disorder in a Person at or Near Sleep and Providing Treatment The system or a method described herein can be used to treat a sleep disorder or an effect thereof in an adult human person transitioning to or from, or being in a state of sleep. Hypersomnia is known to be associated with a number of sleep-related disorders. In some persons these symptoms are characteristic sequelae of primary somnolence disorders, such as narcolepsy, idiopathic hypersomnia, recurrent hypersomnia, and nervous system disorders. In other cases, however, these symptoms present as secondary to a pathology, for example a sleep-related breathing disorder like sleep apnea, or are observed with certain diseases, such as nervous system disorders like Parkinson's Disease or epilepsy, or in patients taking certain medications, e.g. dopamine agonists. For additional description of sleep disorders see e.g., J. Black et al., *Narcolepsy and Syndromes of Primary Excessive Daytime Somnolence*, 24(3) Semin Neurol 271-282 (2004); J. Black et al., *Narcolepsy and Syndromes of Central Nervous System-Mediated Sleepiness*, 3(4) Focus 585-597 (2005); or American Academy of Sleep Medicine, *International Classification of Sleep Disorders Diagnostic and Coding Manual* ($2^{nd}$ ed., 2005); P. Rizzo et al., *Chronic Vagus Nerve Stimulation Improves Alertness and Reduces Rapid Eye Movement Sleep in Patients Affected by Refractory Epilepsy*, 26(5) SLEEP 607-611 (2003).

In humans, there are two types of sleep, rapid eye movement (REM) and non-REM (NREM), which can be identified by electroencephalography (EEG) and electrooculogram (EOG) readings. EEG frequencies are characterized as beta (>13 cycles/sec), alpha (8-13), theta (4-7), and delta (<4 cycles/sec). REM sleep is characterized by mixed high-frequency, low-amplitude 'desynchronized' activity on EEG with theta waves, and by REMs identified on EOG. NREM sleep can be further divided into four stages corresponding to increasing depth of sleep, indicated by progressive dominance in the EEG of high-voltage, low-frequency, and rhythmic, slow 'synchronized' wave activity. Mixed frequency theta waves and slow rolling eye movements characterize stage 1 sleep. An increasing percentage of delta waves is associated with stages 2-4. Throughout the sleep interval, normal sleep architecture is characterized by cycles of light sleep (stages 1 and 2), deeper slow-wave sleep (stages 3 and 4), and REM sleep. Initiation and maintenance of sleep involves a complicated network of neurological and endocrine signaling deep in the brain within and between the hypothalamus, thalamus and brainstem, and recent studies in animals and patients have provided insight into the various roles, including those of the vagus nerve and related pathways, sympathetic and autonomic nervous systems, and hormonal control. Disturbances in the system, due to extrinsic or intrinsic factors, can lead to insufficient sleep and fragmented sleep. Fragmented sleep, (predominantly microfragmentation), has been associated with such conditions as sleep-related breathing disorders like apnea and nervous disorders including epilepsy. Additional description is provided in the articles above and in E. Pace-Schott et al., *The Neurobiology of Sleep: Genetics, cellular physiology and subcortical networks*, 3 Nat. Rev. Neurosci, 591-605 (August 2002); T. Buckley et al., 2005 *REVIEW: On the Interactions of the Hypothalamic-Pituitary-Adrenal (HPA) Axis and Sleep: Normal HPA Axis Activity and Circadian Rhythm, Exemplary Sleep Disorders*, 90 J Clin Endocrinol Metab 3106-3114 (2005); T. Kuo et al., *Asymmetry in sympathetic and vagal activities during sleep-wake transitions*, 31(3) SLEEP 311-320 (2008); and P. Rizzo et al., *Chronic Vagus Nerve Stimulation Improves Alertness and Reduces Rapid Eye Movement Sleep in Patients Affected by Refractory Epilepsy*, 26(5) SLEEP 607-611 (2003).

Hypersomnia, fragmented sleep, sleep apnea, or other sleep-related disorders, or a related effect such as an abnormal sleep state or sleep pattern can be evaluated through EEG, for example by identifying one or more alterations in the distribution of energy in the mammal's EEG signal, or through EOG readings, for example by identification of eye movements as during the REM sleep state. In some cases, for detecting and treating a sleep-related disorder or an effect thereof, the system or method would remotely obtain EEG readings, with or without obtaining concurrent EOG readings. For example, the system or method would include one or more sensor devices having a high input impedance electrometer and configured to measure small electrical potentials, and could include additional devices for obtaining EOG readings. Examples of such sensor devices and technologies are described in U.S. Patent Application Pub. No. 20060058694, supra; WO 2003/048789, supra; C. J. Harland et al., *Remote detection of human electroencephalograms using ultrahigh input impedance electric potential sensors* 81(17) Appl. Phys. Letters, 3284-3286 (2002); and R. J. Prance et al., *Adaptive Electric Potential Sensors for smart signal acquisition and processing*, 76 Journal of Physics: Conference Series 012025 (2007).

Sleep-related disorders such as hypersomnia, fragmented sleep, or sleep apnea, and related conditions such as sleep state, or a transition from a state of wakefulness to sleep, can be assessed by examining a person's cardiac activity including the variability and patterns, such as in an ECG. In some cases, for detecting and treating a sleep-related disorder or effect thereof, the system or method would obtain cardiac activity readings remotely, for example using one or more sensor devices. In one example, the system would include one or more sensor devices able to remotely sense heartbeat intervals and ECG readings by measuring small electrical potentials using a high input impedance electrometer. Examples of such sensor devices can be found in U.S. Patent Application Pub. No. 20060058694, supra; WO 2003/048789, supra; Harland, Meas. Sci. Technol., supra; Prance, 2007 Journal of Physics: Conference Series, supra. As an alternative or in addition, the one or more sensor devices would include a device responsive to an electromagnetic signal directed at, illuminating, and reflected from the person to measure heartbeat intervals and ECG information. An example of such a device is described in U.S. Pat. No. 7,272,431, supra; and US Applications 20040123667 and 20080045832, supra U.S. Patent Application Pub. No. 20040123667, supra; or U.S. Patent Application Pub. No. 20080045832, supra. In some cases, the one or more sensor devices would be worn by the person in a non-conductive contact with the body, for example in or on clothing or jewelry, such as in a wrist band.

An example of such a sensor device is described in U.S. Patent Application Pub. No. 20060058694, supra; WO 2003/048789, supra; and C. J. Harland, 14 Meas. Sci. Technol. 923-928, supra. Alternatively or in addition, the sensor devices would be embedded in or associated with a piece of furniture, such as a bed or pillow, or in a freestanding or tabletop appliance, for example placed on a nightstand, or in electronics such as a personal computing device. The sensor devices could include or be arranged as an array, for example embedded in a number of items or perhaps within a defined area, such as a bedroom. In some cases, the sensor device would acquire information regarding additional physiologic conditions. For example, respiration or temperature could also be obtained remotely using a sensor device as described in U.S. Pat. No. 7,272,431 supra; U.S. Patent Application Pub. No. 20040123667, supra; or U.S. Patent Application Pub. No. 20080045832, supra.

In the system or method for detecting and treating a sleep-related disorder or an effect thereof, information gathered by the one or more sensor devices would be communicated, for example as a signal, to a computer of the system, either via a direct connection or wirelessly. The computer could be part of a network and could include circuitry, for example a treatment regimen circuit or the treatment decision circuit. The computer of the system and its associated circuitry would store or process the information, for example to determine the level of alertness or stage of sleep of the person, using preset parameters. Processing would include application of a computer program and could include input from a user, for example the person or a health care provider. If measured parameters are determined by the computer or user to represent a specific state, the system or user would initiate treatment.

Vagal nerve fibers have a wide distribution throughout the central nervous system (CNS), and vagal stimulation produces evoked potentials from the cerebral cortex, the hippocampus, the thalamus, and the cerebellum. Vagal afferent stimulation has been shown to elicit EEG synchronization or desynchronization and to affect sleep states. For detecting and treating a sleep disorder or an effect thereof, the system or method can provide stimulus or blocking neuromodulation signals to a vagal nerve using a neuromodulation device. In some cases, the neuromodulation device would include a partially or completely implanted device responsive to instructions transmitted from, for example, the computer of the system. For example, the computer of the system, as part of its programming or in response to commands from the user, would communicate instructions wirelessly to the one or more partially or completely implanted neuromodulation devices able to stimulate one or more vagal nerves. For example, the computer of the system, having processed the information from the sensor devices as part of its programming or if instructed to do so by a user, would send out a radio signal to a receiver, associated with an implanted neuromodulation device. Such wireless signaling is described, for example, in U.S. Pat. No. 7,321,793, supra. Alternatively, the system or method would include a neuromodulation device in which a portion, such as a controller, is external to the body of the person and associated with the computer of the system. Such an external controller of the neuromodulation device would be programmed to accept information or instructions from the computer, network, or remote sensor device and, in response to the received information, to transmit a wireless signal to one or more implanted receiving portions of the neuromodulation device, which would then stimulate or block a vagus nerve or fiber. An example of such an external controller is described in U.S. Patent Application Pub. No. 20050131467 by B. Boveja, supra. In some cases, wireless transmission to the receiver would also serve as a means to power the implanted portion of the neuromodulation device. An example of neuromodulation devices with such external controllers with implanted portions are described in U.S. Patent Application Pub. No. 20050143787, by B. Boveja, supra. In some cases, instead of a neuromodulation device implanted in contact with a vagus nerve, the neuromodulation device would have at least a portion that is near the nerve, for example within a nearby blood vessel, through which it can stimulate the nerve. An example of such an intravascular neuromodulation device is described in U.S. Patent Application Pub. No. 20050187584, by S. Denker et al., supra. In some cases, for example as an alternative to wireless communication between the computer and neuromodulation device, the computer of the system would provide an indicator, such as an audio or visual indicator or report, to the person or health care provider instructing them to interface the computer with a portion of the neuromodulation device, such as a controller. For example, the computer would provide visual instructions on a computer screen indicating to the person to place an external controller such as a magnetic controller, near the subcutaneous receiver of the neuromodulation device. The magnetic controller, when placed within range of the receiver, provides instructions to the neuromodulation device, for example to turn the device on or off Examples of such neuromodulation devices and their control are described in U.S. Pat. No. 6,760,626, Apparatus and method for treatment of neurological and neuropsychiatric disorders using programmerless implantable pulse generator system, to B. Boveja.

Treatment for a sleep-related disorder, such as sleep apnea or fragmented sleep, can be provided by the system or method in response to a detection of a sleep state. For example, as a person exits a deep sleep state and enters REM sleep, the one or more sensor devices of the system would detect increased desynchronized activity in the brain by remote EEG, and REMs by EOG. In some cases, the one or more sensors or the computer would accumulate information regarding the length of time the person remained in REM sleep and/or the number of times the person enters REM sleep or other sleep states. The sensor devices would communicate to the computer of the system, which would in turn signal the neuromodulation device to initiate treatment. Treatment, for example, would include inducing an electrical stimulus to modulate the electrical activity of the vagus nerve and thereby alter the electrophysiology of the brain and synchronize the EEG activity, e.g. using the neuromodulating device to provide a stimulus at a frequency at or above 75 Hz and below 3 volts. An example of such treatment is described in U.S. Pat. No. 5,335,657, Therapeutic treatment of sleep disorder by nerve stimulation to T. S. Reese and J. F. Wernicke. In some cases, the sensor devices would detect cardioelectric or respiratory patterns that may be indicative of sleep apnea. If sleep apnea were detected and identified, computer would signal the neuromodulation device to provide treatment, for example to reduce the effects of sleep apnea and encourage sleep. The neuromodulation device would induce an electrical stimulus to modulate the electrical activity of the vagus nerve to alter the electrophysiology and so synchronize the patient's EEG activity. In some cases, treatment would include the neuromodulation device providing stimulation of a nerve branch, for example the trigeminal or glossopharyngeal nerve. In some cases, for example to stimulate multiple nerves or branches, treatment would include the neuromodulation device having multiple electrodes, for example as part of an implant, which could be quite small. Such devices are described in U.S. Pat. No. 5,540,734, Cranial nerve stimulation treatments using neurocybernetic prosthesis, to J. Zabara; or U.S. Pat. No. 7,167,751, Method of using a fully implantable miniature neurostimulator for vagus nerve stimulation, to T. Whitehurst et al. In some cases, the system would include a neuromodulation device that is miniaturized and subcutaneously injectable with an external controller able to interface with the computer of the system. Examples of such subcutaneous injectable neuromodulation devices are described in U.S. Patent Application Pub. No. 20090157147, Implantable Transponder Systems and Methods by L. Cauller and R. Weine.

In some cases using the system or method to treat a sleeping disorder or related condition, such as sleep apnea, would include modulating the autonomic nervous system. In some cases, the remote sensor devices would provide accumulated or real time information to the computer of the system, which would signal the neurmodulation device. The neuromodulation device would provide treatment including stimulating or inhibiting the autonomic nervous system via a nerve pathway. An example of such treatment is described in U.S. Pat. No. 7,149,574, Treatment of conditions through electrical modulation of the autonomic nervous system, to A. Yun et al., In addition or instead, the neuromodulation device would stimulate the spinal cord via an implanted or transcutaneous device. An example of such a device and its use is described in U.S. Pat. No. 7,155,278, Neurostimulation to treat effects of sleep apnea, to G. King et al. Alternatively or in addition, the neuromodulation device would stimulate a targeted nerve such as the phrenic nerve, which would directly affect a physiologic system such as respiration, thereby providing treatment for the sleeping disorder or its effects.

All references cited herein are hereby incorporated by reference in their entirety or to the extent their subject matter is not otherwise inconsistent herewith.

In some embodiments, "configured" includes at least one of designed, set up, shaped, implemented, constructed, or adapted for at least one of a particular purpose, application, or function.

It will be understood that, in general, terms used herein, and especially in the appended claims, are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims may contain usage of introductory phrases such as "at least one" or "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a receiver" should typically be interpreted to mean "at least one receiver"); the same holds true for the use of definite articles used to introduce claim recitations. In addition, even if a specific number of an introduced claim recitation is explicitly recited, it will be recognized that such recitation should typically be interpreted to mean at least the recited number (e.g., the bare recitation of "at least two chambers," or "a plurality of chambers," without other modifiers, typically means at least two chambers).

In those instances where a phrase such as "at least one of A, B, and C," "at least one of A, B, or C," or "an [item] selected from the group consisting of A, B, and C," is used, in general such a construction is intended to be disjunctive (e.g., any of these phrases would include but not be limited to systems that have A alone, B alone, C alone, A and B together, A and C together, B and C together, or A, B, and C together, and may further include more than one of A, B, or C, such as $A_1$, $A_2$, and C together, A, $B_1$, $B_2$, $C_1$, and $C_2$ together, or $B_1$ and $B_2$ together). It will be further understood that virtually any disjunctive word or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The herein described aspects depict different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality. Any two components capable of being so associated can also be viewed as being "operably couplable" to each other to achieve the desired functionality. Specific examples of operably couplable include but are not limited to physically mateable or physically interacting components or wirelessly interactable or wirelessly interacting components.

With respect to the appended claims the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Use of "Start," "End," "Stop," or the like blocks in the block diagrams is not intended to indicate a limitation on the beginning or end of any operations or functions in the diagram. Such flowcharts or diagrams may be incorporated into other flowcharts or diagrams where additional functions are performed before or after the functions shown in the diagrams of this application. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   a sensor device operable to detect a property of a mammal without a direct physical contact with the mammal;
   a patient assessment device operable to evaluate the detected property of the mammal for an indicator of a disease, disorder, or symptom potentially treatable by a neuromodulation treatment regimen;
   a patient information device including a computer-readable medium and configured to maintain and to provide access to information corresponding to the indicator of the disease, disorder, or symptom potentially treatable by the neuromodulation treatment regimen;
   a transmitter device operable to broadcast a signal indicative of the disease, disorder, or symptom potentially treatable by the neuromodulation treatment regimen; and
   a neuromodulation device programmed to administer the neuromodulation treatment regimen to the mammal in response to the signal from the transmitter device.

2. The system of claim 1, wherein the sensor device operable to detect a property of a mammal without a direct contact with the mammal includes:
   a sensor device operable to detect a property of a mammal absent a direct conductive, electrical, or physical contact with the mammal.

3. The system of claim 1, wherein the sensor device operable to detect a property of a mammal without a direct contact with the mammal includes:
   a sensor device operable to at least one of electronically, sonically, acoustically, thermally, radiatively, or chemically detect a property of a mammal without a direct contact with the mammal.

4. The system of claim 1, wherein the patient assessment device includes:
   a patient assessment device physically distinct and spatially apart from the sensor device.

5. The system of claim 1, wherein the disease, disorder, or symptom includes at least one of a neurological disease, nervous system disorder, heart rhythm, or heart disease.

6. The system of claim 1, wherein the patient assessment device operable to evaluate the detected property of the mammal for the indicator of the disease, disorder, or symptom potentially treatable by the neuromodulation treatment regimen includes:
   a patient assessment device operable to receive a signal indicative of the detected property of the mammal, and to evaluate the detected property of the mammal for the indicator of the disease, disorder, or symptom potentially treatable by the neuromodulation treatment regimen.

7. The system of claim 1, wherein the patient assessment device operable to evaluate the detected property of the mammal for the indicator of a disease, disorder, or symptom potentially treatable by the neuromodulation treatment regimen includes:
   a patient assessment device operable to evaluate the detected property of the mammal for a physiological characteristic of the mammal, and to identify the disease, disorder, or symptom potentially treatable by the neuromodulation treatment regimen in response to the evaluated physiological characteristic of the mammal.

8. The system of claim 1, wherein the patient assessment device is operable to determine the neuromodulation treatment regimen in response to the indicator of the disease, disorder, or symptom potentially treatable by the neuromodulation treatment regimen.

9. The system of claim 1, wherein the patient assessment device is programmed to determine the neuromodulation treatment regimen in response to the indicator of the disease, disorder, or symptom potentially treatable by the neuromodulation treatment regimen according to a selected outcome.

10. The system of claim 1, wherein the patient assessment device is programmed to determine a therapeutic neuromodulation treatment regimen in response to the indicator of the disease, disorder, or symptom potentially treatable by the neuromodulation treatment regimen.

11. The system of claim 1, wherein the patient assessment device is further operable to transmit a second signal responsive to the indicator of a disease.

12. The system of claim 1, wherein the patient assessment device operable to evaluate the detected property of the mammal for the indicator of the disease, disorder, or symptom potentially treatable by the neuromodulation treatment regimen includes:
an electronically implemented patient assessment device operable to evaluate the detected property of the mammal for an indicator of the disease, disorder, or symptom potentially treatable by the neuromodulation treatment regimen.

13. The system of claim 1, wherein the patient assessment device operable to evaluate the detected property of the mammal for the indicator of the disease, disorder, or symptom potentially treatable by the neuromodulation treatment regimen includes:
a patient assessment device operable to evaluate using an artificial intelligence technique the detected property of the mammal for an indicator of the disease, disorder, or symptom potentially treatable by the neuromodulation treatment regimen.

14. The system of claim 1, wherein the patient assessment device operable to evaluate the detected property of the mammal for the indicator of the disease, disorder, or symptom potentially treatable by the neuromodulation treatment regimen includes:
a patient assessment device operable to evaluate the detected property of the mammal for an indicator of a disease using a digitally maintained table indicating a possible correlation between the detected property and the indicator of the disease, disorder, or symptom potentially treatable by the neuromodulation treatment regimen.

15. The system of claim 1, further comprising a mammal information device that shares at least a portion of a common chassis with the patient assessment device.

16. The system of claim 1, further comprising:
a user interface operable to electronically output a human-perceivable indication of the disease in response to the broadcast signal indicative of the disease, disorder, or symptom potentially treatable by the neuromodulation treatment regimen.

17. The system of claim 16, wherein the patient information device and the user interface share at least a portion of a common chassis.

18. The system of claim 16, wherein the user interface operable to electronically output a human-perceivable indication of the disease in response to the broadcast signal indicative of the disease, disorder, or symptom potentially treatable by the neuromodulation treatment regimen includes:
a user interface operable to electronically output a visual or audible indication of the disease in response to the broadcast signal indicative of the disease.

19. The system of claim 16, wherein the user interface is operable to electronically output a proffered neuromodulation treatment regimen responsive to the disease.

20. The system of claim 16, wherein the user interface operable to electronically output a human-perceivable indication of the disease, disorder, or symptom potentially treatable by the neuromodulation treatment regimen in response to the broadcast signal indicative of the disease includes:
a user interface operable to electronically display a tactile indication of the disease, disorder, or symptom potentially treatable by the neuromodulation treatment regimen in response to the broadcast signal indicative of the disease.

21. The system of claim 16, wherein the user interface operable to electronically output a human-perceivable indication of the disease in response to the broadcast signal indicative of the disease, disorder, or symptom potentially treatable by the neuromodulation treatment regimen includes:
a user interface operable to electronically display a visual, audible, or tactile indication of the disease in response to the broadcast signal indicative of the disease, disorder, or symptom potentially treatable by the neuromodulation treatment regimen.

22. The system of claim 16, wherein the user interface is operable to receive a human-originated input responsive to the indication of the disease, disorder, or symptom potentially treatable by the neuromodulation treatment regimen.

23. The system of claim 16, wherein the user interface is further operable to (a) electronically output
(i) a proffered neuromodulation treatment regimen responsive to the disease, disorder, or symptom potentially treatable by the neuromodulation treatment regimen; and
(b) receive a human-originated input responsive to the proffered neuromodulation treatment regimen.

24. The system of claim 16, wherein the user interface operable to electronically output a human-perceivable indication of the disease in response to the broadcast signal indicative of the disease, disorder, or symptom potentially treatable by the neuromodulation treatment regimen includes:
a user interface operable to electronically output a human-perceivable indication of the disease to a person other than the mammal in response to the broadcast signal indicative of the disease, disorder, or symptom potentially treatable by the neuromodulation treatment regimen.

25. The system of claim 1, further comprising:
a treatment controller operable to control an administration of the neuromodulation treatment regimen to a nervous system component of the mammal.

26. The system of claim 25, wherein the patient information device and the treatment controller device share at least a portion of a common chassis.

27. The system of claim 25, wherein the treatment controller operable to control an administration of a neuromodulation treatment regimen to a nervous system component of the mammal includes:
a treatment controller operable to control an administration of a neuromodulation treatment regimen to a nervous system component of the mammal in response to a human-originated input responsive to a proffered neuromodulation treatment regimen.

28. The system of claim 25, wherein the treatment controller is operable to communicate with the neuromodulation device.

29. The system of claim 1, wherein the neuromodulation device is operable to administer the neuromodulation treatment regimen to a nervous system component of the mammal.

30. The system of claim 1, further comprising:
an illumination source operable to illuminate at least a portion of the mammal with an energy to which the sensor device is responsive.

31. A system comprising:
a sensor device operable to detect a property of a mammal without a direct contact with the mammal;
a patient assessment device operable to evaluate the detected property of the mammal for an indicator of a disease, disorder, or symptom potentially treatable by a neuromodulation treatment regimen;
a user interface device operable to electronically output a human-perceivable information responsive to the disease;
a patient information device having a computer-readable medium, and configured to maintain information corresponding to the indicator of the disease, disorder, or symptom potentially treatable by the neuromodulation treatment regimen and to provide access to the maintained information; and
a transmitter device programmed to broadcast a signal indicative of the disease, disorder, or symptom potentially treatable by the neuromodulation treatment regimen to a neuromodulation device.

32. The system of claim 31, wherein the user interface device is operable to electronically receive an indication of a human-initiated authorization to initiate a neuromodulation treatment regimen to a nervous system component of the mammal.

33. The system of claim 32, wherein the patient information device is configured to maintain information corresponding to the indication of a human-initiated authorization and to provide access to the maintained information.

34. The system of claim 31, further comprising:
a neuromodulation device operable to deliver the neuromodulation treatment regimen to a nervous system component of the mammal.

35. A method comprising:
acquiring electronic data indicative of a property of a mammal without making physical contact with the mammal;
evaluating the detected property of the mammal for an indicator of a disease, disorder, or symptom potentially treatable by a neuromodulation treatment regimen based on the acquired electronic data indicative of the property of the mammal;
identifying the disease in response to the indicator of the disease, disorder, or symptom potentially treatable by the neuromodulation treatment regimen;
maintaining and providing access to electronically stored information corresponding to the indicator of the disease, disorder, or symptom potentially treatable by the neuromodulation treatment regimen;
broadcasting a signal indicative of the disease; and
administering the neuromodulation treatment regimen in response to the signal indicative of the disease.

36. The method of claim 35, further comprising:
electronically outputting a human-perceivable indication of the disease in response to the broadcast signal indicative of the disease, disorder, or symptom potentially treatable by the neuromodulation treatment regimen.

37. The method of claim 35, further comprising:
administering a neuromodulation treatment regimen to a nervous system component of the mammal in response to a human-originated input.

38. The method of claim 37, wherein the administering a neuromodulation treatment regimen to a nervous system component of the mammal in response to a human-originated input includes:
administering a neuromodulation treatment regimen to a nervous system component of the mammal in response to a human-originated input responsive to a proffered neuromodulation treatment regimen.

39. A system comprising:
means for acquiring electronic data indicative of a property of a mammal without making physical contact with the mammal;
means for evaluating the detected property of the mammal for an indicator of a disease, disorder, or symptom potentially treatable by a neuromodulation treatment regimen based on the acquired electronic data indicative of a property of a mammal;
means for maintaining and providing access to electronically stored information corresponding to the indicator of the disease, disorder, or symptom potentially treatable by the neuromodulation treatment regimen;
means for electronically outputting a human-perceivable indication of the disease, disorder, or symptom potentially treatable by the neuromodulation treatment regimen; and
means for administering the neuromodulation treatment regimen to a nervous system component of the mammal in response to a human-originated input and the electronically stored information corresponding to the indicator of the disease, disorder, or symptom.

40. The system of claim 39, wherein the means for administering a neuromodulation treatment regimen to a nervous system component of the mammal in response to a human-originated input includes:
means for administering a neuromodulation treatment regimen to a nervous system component of the mammal in response to a human-originated input that is responsive to a proffered neuromodulation treatment regimen.

* * * * *